(12) United States Patent
Diamond et al.

(10) Patent No.: US 9,453,227 B2
(45) Date of Patent: Sep. 27, 2016

(54) TUMOR ASSOCIATED VACCINES AND COMPOSITIONS FOR DISRUPTING TUMOR-DERIVED IMMUNOSUPPRESSION FOR USE IN COMBINATION CANCER IMMUNOTHERAPY

(71) Applicant: CITY OF HOPE, Duarte, CA (US)

(72) Inventors: Don J. Diamond, Glendora, CA (US); Edwin Manuel, San Diego, CA (US); Fernanda V. V. Castro, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/065,284

(22) Filed: Oct. 28, 2013

(65) Prior Publication Data

US 2014/0186401 A1 Jul. 3, 2014

Related U.S. Application Data

(63) Continuation of application No. PCT/US2012/035512, filed on Apr. 27, 2012.

(60) Provisional application No. 61/480,316, filed on Apr. 28, 2011, provisional application No. 61/615,167, filed on Mar. 23, 2012.

(51) Int. Cl.
| | |
|---|---|
| *A01N 63/00* | (2006.01) |
| *A61K 48/00* | (2006.01) |
| *C12N 15/113* | (2010.01) |
| *A61K 39/00* | (2006.01) |
| *A61K 39/39* | (2006.01) |

(52) U.S. Cl.
CPC ....... *C12N 15/1138* (2013.01); *A61K 39/0011* (2013.01); *A61K 39/39* (2013.01); *C12N 15/1136* (2013.01); *C12N 15/1137* (2013.01); *C12Y 113/11052* (2013.01); *C12Y 305/03001* (2013.01); *C12N 2310/14* (2013.01); *C12N 2310/531* (2013.01); *C12N 2320/32* (2013.01); *C12N 2330/50* (2013.01)

(58) Field of Classification Search
CPC .................................................. C12N 15/1138
See application file for complete search history.

(56) References Cited

U.S. PATENT DOCUMENTS

| | | | |
|---|---|---|---|
| 2008/0113351 A1 | 5/2008 | Naito | |
| 2009/0158451 A1* | 6/2009 | Prendergast et al. | 800/18 |
| 2009/0208534 A1 | 8/2009 | Xu | |
| 2009/0220582 A1 | 9/2009 | Min | |
| 2010/0239546 A1 | 9/2010 | Fruehauf | |

FOREIGN PATENT DOCUMENTS

WO WO 2012149364 A1 11/2012

OTHER PUBLICATIONS

Altieri, D. C. and Marchisio, P. C. Survivin apoptosis: an interloper between cell death and cell proliferation in cancer. Lab Invest. 79: 1327-1333, 1999.
Altieri, D. C. Validating survivin as a cancer therapeutic target. Nat Rev Cancer, 3: 46-54, 2003.
Anderson, M. J., Shafer-Weaver, K., Greenberg, N. M., and Hurwitz, A. A. Tolerization of tumor-specific T cells despite efficient initial priming in a primary murine model of prostate cancer. J Immunol. 176: 1268-1276, 2007.
Angelakopoulos H, Hohmann EL. Pilot study of phoP/phoQ-deleted *Salmonella enterica* serovar typhimurium expressing *Helicobacter pylori* urease in adult volunteers. Infect Immun. 2000;68:2135-2141.
Aoki, Y., Feldman, G. M., and Tosato, G. Inhibition of STAT3 signaling induces apoptosis and decreases survivin expression in primary effusion lymphoma. Blood, 101: 1535-1542, 2003.
Arrach N, Zhao M, Porwollik S, Hoffman RM, McClelland M. *Salmonella* promoters preferentially activated inside tumors. Cancer Res. 2008;68:4827-4832.
Aulak, K.S., et al. Proteomic method identifies proteins nitrated in vivo during inflammatory challenge. Proc. Natl Acad Sci U S A 98, 12056-12061 (2001).
Avogadri F, Martinoli C, Petrovska L et al. Cancer immunotherapy based on killing of *Salmonella*-infected tumor cells. Cancer Res. 2005;65:3920-3927.
Baban B, Chandler PR, Sharma MD et al. IDO activates regulatory T cells and blocks their conversion into Th17-like T cells. J. Immunol. 2009;183:2475-2483.
Banerjee T, DuHadaway JB, Gaspari P et al. A key in vivo antitumor mechanism of action of natural product-based brassinins is inhibition of indoleamine 2,3-dioxygenase. Oncogene. 2008;27:2851-2857.
Basu GD, Tinder TL, Bradley JM et al. Cyclooxygenase-2 inhibitor enhances the efficacy of a breast cancer vaccine: role of IDO. J Immunol. 2006;177:2391-2402.
Baud, D., Ponci, F., Bobst, M., De Grandi, P., and Nardelli-Haefliger, D. Improved efficiency of a *Salmonella*-based vaccine against human papillomavirus type 16 viruslike particles achieved by using a codon-optimized version of L1. J Virol. 78: 12901-12909, 2004.
Beauvillain C, Delneste Y, Scotel M et al. Neutrophils efficiently cross-prime naive T cells in vivo. Blood. 2007;110:2965-2973.
Belladonna ML, Volpi C, Bianchi R et al. Cutting edge: Autocrine TGF-beta sustains default tolerogenesis by IDO-competent dendritic cells, J Immunol. 2008;181:5194-5198.

(Continued)

*Primary Examiner* — Albert Navarro
(74) *Attorney, Agent, or Firm* — Perkins Coie LLP; Lara Dueppen

(57) ABSTRACT

In one embodiment, a single modality cancer immunotherapy regimen that includes a therapeutic composition is provided. Such a therapeutic composition may include a *Salmonella* strain comprising a plasmid that expresses an shRNA molecule that suppresses the expression of an immunosuppressive target and suppresses tumor growth. In some aspects, the *Salmonella* strain is an attenuated *Salmonella typhimurium* strain. In other aspects, the immunosuppressive target is STAT3, IDO1, IDO2, Arginase 1, iNOS, CTLA-4, TGF-β, IL-10, pGE2 or VEGF. In one embodiment, the immunosuppressive target is IDO1 or Arg1 and the shRNA molecule is any one of SEQ ID NO:5-14.

9 Claims, 51 Drawing Sheets

(56) References Cited

OTHER PUBLICATIONS

Bellavance EC, Kohlhapp FJ, Zloza A et al. Development of Tumor-Infiltrating CD8+ T Cell Memory Precursor Effector Cells and Antimelanoma Memory Responses Are the Result of Vaccination and TGF-(beta) Blockade during the Perioperative Period of Tumor Resection. J Immunol. 2011; 186:3309-3316.

Bennouna S, Bliss SK, Curiel TJ, Denkers EY. Cross-talk in the innate immune system: neutrophils instruct recruitment and activation of dendritic cells during microbial infection. J Immunol. 2003;171:6052-6058.

Bereta M, Hayhurst A, Gajda M et al. Improving tumor targeting and therapeutic potential of *Salmonella* VNP20009 by displaying cell surface CEA-specific antibodies. Vaccine. 2007;25:4183-4192.

Berghella, A. M., Pellegrini, P., Del Beato, T., Adorno, D., and Casciani, C. U. IL-10 and sIL-2R serum levels as possible peripheral blood prognostic markers in the passage from adenoma to colorectal cancer. Cancer Biother Radiopharm, 12: 265-272, 1997.

Bermudes D, Zheng LM, King IC, Live bacteria as anticancer agents and tumorselective protein delivery vectors. Curr Opin Drug Discov Devel. 2002;5:194-199.

Brandau, S., et al. Myeloid-derived suppressor cells in the peripheral blood of cancer patients contain a subset of immature neutrophils with impaired migratory properties. J Leukoc Biol 89, 311-317 (2011).

Breitbach CJ, Paterson JM, Lemay CG et al. Targeted inflammation during oncolytic virus therapy severely compromises tumor blood flow. Mol Ther. 2007;15:1686-1693.

Brito, C., et al. Peroxynitrite inhibits T lymphocyte activation and proliferation by promoting impairment of tyrosine phosphorylation and peroxynitrite-driven apoptotic death. J Immunol 162, 3356-3366 (1999).

Bronte, V., Serafini, P., De Santo, C., Marigo, I., Tosello, V., Mazzoni, A., Segal, D., Staib, C., Lowel, M., Sutter, G., Colombo, M., & Zanovello, P. IL-4-induced arginase 1 suppresses alloreactive T cells in tumor-bearing mice. J Immunol 170, 270-278 (2003).

Bronte, V., Serafini, P., Mazzoni, A., Segal, D.M. & Zanovello, P. L-arginine metabolism in myeloid cells controls T-lymphocyte functions. Trends Immunol 24, 302-306 (2003).

Bronte, V. & Zanovello, P. Regulation of immune responses by L-arginine metabolism. Nat Rev Immunol 5, 641-654 (2005).

Bunt, S.K., Clements, V.K., Hanson, E.M., Sinha, P. & Ostrand-Rosenberg, S. Inflammation enhances myeloid-derived suppressor cell cross-talk by signaling throuh Toll-like receptor 4. J Leukoc Biol 85, 896-1004 (2009).

Buonocore S, Haddou NO, Moore F et al. Neutrophil-dependent tumor rejection and priming of tumoricidal CD8+ T cell response induced by dendritic cells overexpressing CD95L. J Leukoc Biol. 2008;84:713-720.

Byrne, S. N. and Halliday, G. M. High levels of Fas ligand and MHC class II in the absence of CD80 or CD86 expression and a decreased CD4+ T cell infiltration, enables murine skin tumours to progress. Cancer Immunol Immunother, 52: 396-402, 2003.

Cady SG, Sono M. 1-Methyl-DL-tryptophan, beta-(3-benzofuranyl)-DL-alanine (the oxygen analog of tryptophan), and beta-[3-benzo(b)thienyl]-DL-alanine (the sulfur analog of tryptophan) are competitive inhibitors for indoleamine 2,3-dioxygenase. Arch Biochem Biophys. 1991;291:326-333.

Cassatella MA. Neutrophil-derived proteins: selling cytokines by the pound. Adv Immunol. 1999;73:369-509.

Catic, A., Dietrich, G., Gentschev, I., Goebel, W., Kaufmann, S. H., and Hess, J. Introduction of protein or DNA delivered via recombinant *Salmonella typhimurium* into the major histocompatibility complex class I presentation pathway of microphages. Microbes Infect. 1: 113-121, 1999.

Challacombe JM, Suhrbier A, Parsons PG et al. Neutrophils are a key component of the antitumor efficacy of topical chemotherapy with ingenol-3-angelate. J. Immunol. 2006;177:8123-8132.

Chen, G., Wei, D. P., Jia, L. J. Tang, B., Shu, L., Zhang, K., Xu, Y., Gao, J., Huang, X. F., Jiang, W. H., Hu, Q. G., Huang, Y., Wu, Q., Sun, Z. H., Zhang, J. F., and Hua, Z. C. Oral delivery of tumor-targeting *Salmonella* exhibits promising therapeutic efficacy and low toxicity. Cancer Sci. 100: 2437-2443, 2009.

Chen, Y.L., Chen, S.H., Wang, J.Y. & Yang, B.C. Fas ligand on tumor cells mediates inactivation of neutrophils. J Immunol 171, 1183-1191 (2003).

Cho D, Song H, Kim YM et al. Endogenous interleukin-18 modulates immune escape of murine melanoma cells by regulating the expression of Fas ligand and reactive oxygen intermediates. Cancer Res. 2000;60:2703-2709.

Ciorba MA, Bettonville EE, McDonald KG et al. Induction of IDO-1 by Immunostimulatory DNA Limits Severity of Experimental Colitis. J Immunol. 2010;184:3907-3916.

Clairmont, C., Lee, K. C., Pike, J., Ittensohn, M., Low, K. B., Pawelek, J., Bermudes, D., Brecher, S. M., Margitich, D., Turnier, J., Li, Z., Luo, X., King, I., and Zheng, L. M. Biodistribution and genetic stability of the novel antitumor agent VNP20009, a genetically modified strain of *Salmonella typhimurium*. J Infect Dis, 181: 1996-2002, 2000.

Cote AL, Zhang P, O'Sulllivan JA et al. Stimulation of the glucocorticoid-induced TNF receptor family-related receptor on CD8 T cells induces protective and high-avidity T cell responses to tumor-specific antigens. J Immunol. 2011;186:275-283.

Dai, S. and Zhou, D. Secretion and function of *Salmonella* SPI-2 effector SseF require its chaperone, SscB. J Bacteriol, 186: 5078-5086, 2004.

Daley JM, Thomay AA, Connolly MD, Reichner JS, Albina JE. Use of Ly6G-specific monoclonal antibody to deplete neutrophils in mice. J Leukoc Biol. 2008;83:64-70.

Dallegri, F. & Ottonello, L. Neutrophil-mediated cytotoxicity against tumour cells: state of art, Arch Immunol Ther Exp (Warsz) 40, 39-42 (1992).

De Vita, F., Orditura, M., Galizia, G., Romano, C., Roscigno, A., Lieto, E., and Catalano, G. Serum interleukin-10 levels as a prognostic factor in advanced non-small cell lung cancer patients. Chest. 117: 365-373, 2000.

Deepak, P. and Acharya, A. Anti-tumor immunity and mechanism of immunosuppression mediated by tumor cells: role of tumor-derived soluble factors and cytokines. Int Rev Immunol, 29: 421-458, 2010.

Deiwick, J., Nikolaus, T., Erdogan, S., and Hensel, M. Environmental regulation of *Salmonella* pathogenicity island 2 gene expression. Mol Microbiol, 31: 1759-1773, 1999.

Di Carlo, E. et al. Neutrophils in anti-cancer immunological strategies: old players in new games. J. Hematother Stem Cell Res 10, 739-748 (2001b).

Di Carlo, E. et al. The intriguing role of polymorphonuclear neutrophils in antitumor reactions. Blood 97, 339-345 (2001a).

Dolcetti, L., et al. Hierarchy of immunosuppressive strength among myeloid-derived suppressor cell subsets is determined by GM-CSF. Eur J Immunol 40, 22-35 (2010).

Drake CG, Jaffee E, Pardoll DM. Mechanisms of immune evasion by tumors. Adv Immunol. 2006;90:51-81.

Echchannaoui H, Bianchi M, Baud D et al. Intravaginal immunization of mice with recombinant *Salmonella enterica* serovar Typhimurium expressing human papillomavirus type 16 antigens as a potential route of vaccination against cervical cancer. Infect Immun. 2008;76:1940-1951.

Evans, D. T., Chen, L. M., Gillis, J., Lin, K. C., Harty, B., Mazzara, G. P., Donis, R. O., Mansfield, K. G., Lifson, J. D., Desrosiers, R. C., Galan, J. E., and Johnson, R. P. Mucosal priming of simian immunodeficiency virus-specific cytotoxic T-lymphocyte responses in rhesus macaques by the *Salmonella* type III secretion antigen deliverysystem. J. Virol, 77:2400-2409, 2003.

Fallarino F, Grohmann U, Hwang KW et al. Modulation of tryptophan catabolism by regulatory T cells. Nat Immunol. 2003; 4:1206-1212.

Fleming, T.J., Fleming, M.L. & Malek, T.R. Selective expression of Ly-6G on myeloid lineage cells in mouse bone marrow. RB6-8C5 mAb to granulocyte differentiation antigen (Gr-1) detects members of the Ly-6 family. J Immunol 151, 2399-2408 (1993).

Fligger, J., Blum, J. & Jungi, T.W. Induction of intracellular arginase activity does not diminish the capacity of macrophages to produce nitric oxide in vitro. Immunobiology 200, 169-186 (1999).

(56) References Cited

OTHER PUBLICATIONS

Forbes NS, Munn LL, Fukumura D, Jain RK. Sparse initial entrapment of systemically injected *Salmonella typhimurium* leads to heterogenous accumulation within tumors. Cancer Res. 2003;63:5188-5193.

Friberg M, Jennings R, Alsarraj M et al. Indoleamine 2,3-dioxygenase contributes to tumor cell evasion of T cell-mediated rejection. Int J Cancer. 2002;101:151-155.

Fridlender ZG, Sun J, Kim S et al. Polarization of tumor-associated neutrophil phenotype by TGF-beta: "N1" versus "N2" TAN. Cancer Cell. 2009;16:183-194.

Frumento, G., Rotondo, R., Tonetti, M., Damonte, G., Benatti, U., and Ferrara, G. B. Tryptophan-derived catabolites are responsible for inhibition of T and natural killer cell proliferation induced by indoleamine 2,3-dioxygenase. J Exp Med, 196: 459-468, 2002.

Gajewski, T. F., Meng, Y., and Harlin, H. Immune suppression in the tumor microenvironment. J Immunother, 29: 233-240, 2006.

Gaspari P, Banerjee T, Malachowski WP et al. Structure-activity study of brassinin derivatives as indoleamine 2,3-dioxygenase inhibitors. J Med Chem. 2006;49:684-692.

Grohmann U, Orabona C, Fallarino F et al. CTLA-4-Ig regulates tryptophan catabolism in vivo. Nat Immunol. 2002;3:1097-1101.

Gunn BM, Wanda SY, Burshell D, Wang C, Curtiss R, III. Construction of Recombinant Attenuated *Salmonella enterica* Serovar Typhimurium Vaccine Vector Strains for Safety in Newborn and Infant Mice. Clin Vaccine Immunol. 2010;17:354-362.

Haraga, A., Ohlson, M. B., and Miller, S. I. *Salmonellae* interplay with host cells. Nat Rev Microbiol, 6: 53-66, 2006.

Harding HP, Zhang Y, Zeng H et al. An integrated stress response regulates amino acid metabolism and resistance to oxidative stress. Mol Cell. 2003;11:619-633.

Heimann DM, Rosenberg SA. Continuous intravenous administration of live genetically modified *Salmonella typhimurium* in patients with metastatic melanoma. J Immunother. 2003;26:179-180.

Hernandez-Ilizaliturri, F.J. et al. Neutrophils contribute to the biological antitumor activity of rituximab in a non-Hodgkin's lymphoma severe combined immunodeficiency mouse model. Clin Cancer Res 9, 5866-5873 (2003).

Hodi FS, O'Day SJ, McDermott DF et al. Improved Survival with Ipilimumab in Patients with Metastatic Melanoma. N Engl J Med. 2010; 363;711-723.

Hoshi M, Saito K, Hara A et al. The absence of IDO upregulates type I IFN production, resulting in suppression of viral replication in the retrovirus-infected mouse. J Immunol. 2010;185:3305-3312.

Hou DY, Muller AJ, Sharma MD et al. Inhibition of indoleamine 2,3-dioxygenase in dendritic cells by stereoisomers of 1-methyl-tryptophan correlates with antitumor responses. Cancer Res. 2007;67:792-801.

Hu, C.E., Gan, J., Zhang, R.D., Cheng, Y.R. & Huang, G.J. Up-regulated myeloidderived suppresor cell contributes to hepatocellular carcinoma development by impairing dendritic cell function. Scand J Gastroenterol 46, 156-164 (2011).

Huang, B., et al. Gr-1+CD115+ immature myeloid suppressor cells mediate the develoment of tumor-induced T regulatory cells and T-cell anergy in tumor-bearing host. Cancer Res 66, 1123-1131 (2006).

Husseiny MI, Wartha F, Hensel M. Recombinant vaccines based on translocated effector proteins of *Salmonella* Pathogenicity Island 2. Vaccine. 2007;25:185-193.

Hwu, P., Du, M. X., Lapointe, R., Do, M., Taylor, M. W., and Young, H. A. Indoleamine 2,3-dioxygenase production by human dendritic cells results in the inhibition of T cell proliferation. J Immunol, 164: 3596-3599, 2000.

Igney, F.H. & Krammer, P.H. Immune escape of tumors: apoptosis resistance and tumor counterattack. J Leukoc Biol 71, 907-920 (2002).

Ishizaki, H., Manuel, E. R., Song, G. Y., Srivastava, T., Sun, S., Diamond, D. J., and Ellenhorn, J. D. Modified vaccinia Ankara expressing survivin combined with gemcitabine generates specific antitumor effects in a murine pancreatic carcinoma model. Cancer Immunol Immunother. 2010 DOI: 10. 1007/s00262-010-0923-0; 60:99-109.

Kallberg E, Wikstrom P, Bergh A, Ivars F, Leanderson T. Indoleamine 2,3-dioxygenase (IDO) activity influence tumor growth in the TRAMP prostate cancer model. Prostate. 2010;70:1461-1470.

Katz JB, Muller AJ, Prendergast GC. Indoleamine 2,3-dioxygenase in T-cell tolerance and tumoral immune escape. Immunol Rev. 2008;222-206-221.

Kemp TJ, Ludwig AT, Earel JK et al. Neutrophil stimulation with *Mycobacterium bovis* bacillus Calmette-Guerin (BCG) results in the release of functional soluble TRAIL/Apo-2L. Blood. 2005;106:3474-3482.

King, I., Itterson, M., and Bermudes, D. Tumor-targeted *Salmonella typhimurium* overexpressing cytosine deaminase: a novel, tumor-selective therapy. Methods Mol Biol, 542: 649-659, 2009.

Kirby, A.C., Yrlid, U. & Wick, M.J. The innate immune response differs in primary and secondary *Salmonella* infection. J Immunol 169, 4450-4459 (2002).

Klebanoff CA, Acquavella N, Yu Z, Restifo NP. Therapeutic cancer vaccines: are we there yet? Immunol Rev. 2011;239:27-44.

Koblish HK, Hansbury MJ, Bowman KJ et al. Hydroxyamidine inhibitors of indoleamine-2,3-dioxygenase potently suppress systemic tryptophan catabolism and the growth of IDOexpressing tumors. Mol Cancer Ther. 2010;9:489-498.

Kortylewski, M., Kujawski, M., Wang, T., Wei, S., Zhang, S., Pilon-Thomas, S., Niu, G., Kay, H., Mule, J., Kerr, W. G., Jove, R., Pardoll, D., and Yu, H. Inhibiting Stat3 signaling in the hematopoietic system elicits multicomponent antitumor immunity. Nat Med. 11:1314-1321, 2005.

Kortylewski, M., Swiderski, P., Herrmann, A., Wang, L., Kowolik, C., Kujawski, M., Lee, H., Scuto, A., Liu, Y., Yang, C., Deng, J., Soifer, H. S., Raubitschek, A., Forman, S., Rossi, J. J., Pardoll, D. M., Jove, R., and Yu, H. In vivo delivery of siRNA to immune cells by conjugation to a TLR9 agonist enhances antitumor immune responses. Nat Biotechnol, 27:925-932, 2009a.

Kortylewski, M., Xin, H., Kujawski, M., Lee, H., Liu, Y., Harris, T., Drake, C., Pardoll, D., and Yu, H. Regulation of the IL-23 and IL-12 balance by Stat3 signaling in the tumor microenvironment. Cancer Cell, 15: 114-123, 2009b.

Kortylewski, M. and Yu, H. Role of Stat3 in suppressing anti-tumor immunity. Curr Opin Immunol, 20: 228-233, 2008.

Kousis PC, Henderson BW, Maier PG, Gollnick, SO. Photodynamic therapy enhancement of antitumor immunity is regulated by neutrophils. Cancer Res. 2007;67:10501-10510.

Kraman, M., Bambrough, P. J., Arnold, J. N., Roberts, E. W., Magiera, L., Jones, J. O., Gopinathan, A., Tuveson, D. A., and Fearon, D. T. Suppression of antitumor immunity by stromal cells expressing fibroblast activation protein-alpha. Science. 330: 827-830, 2010.

Kumar, S. et al. Indoleamine 2,3-dioxygenase is the anticancer target for a novel series of potent naphthoquinone-based inhibitors. J Med Chem 51, 1706-1718 (2008).

Lazennec G, Richmond A. Chemokines and chemokine receptors: new insights into cancerrelated inflammation. Trends Mol Med. 2010;16:133-144.

Lechner et al. Inducible nitric oxide synthase (iNOS) in tumor biology: The two sides of the same coin. Semin Cancer Biol. 15(4):277-89 (2005).

Lee CH, Hsieh JL, Wu CL, Hsu PY, Shiau AL. T cell augments the antitumor activity of tumortargeting *Salmonella*. Appl Microbiol Biotechnol. 2011;90:1381-1388.

Lee, H., Pal, S. K., Reckamp, K., Figlin, R. A., and Yu, H. STAT3: A Target to Enhance Antitumor Immune Response. Curr Top Microbiol Immunol., 2011; 344:41-59.

Liu X, Shin N, Koblish HK et al. Selective inhibition of IDO1 effectively regulates mediators of antitumor immunity. Blood. 2010;115:3520-3530.

Lob, S., Konigsrainer, A., Rammensee, H.G., Opelz, G. & Terness, P. Inhibitors of indoleamine-2,3-dioxygenase for cancer therapy: can we see the wood for the trees? Nat Rev Cancer 9, 445-452 (2009).

(56) References Cited

OTHER PUBLICATIONS

Low K.B., Ittensohn M, Le T et al. Lipid A mutant *Salmonella* with suppressed virulence and TNFalpha induction retain tumor-targeting in vivo. Nat Biotechnol. 1999;17:37-41.

Low, K.B. et al. Construction of VNP20009: a novel, genetically stable antibioticsensitive strain of tumor-targeting *Salmonella* for parenteral administration in humans. Methods Mol Med 90, 47-60 (2004).

Lu, T., et al. Tumor-infiltrating myeloid cells induce tumor cell resistance to cytotoxic T cells in mice. J Clin Invest 121, 4015-4029 (2011).

Luo Y, Markowitz D, Xiang R, Zhou H, Reisfeld RA. FLK-1-based minigene vaccines induce T cell-mediated suppression of angiogenesis and tumor protective immunity in syngeneic BALB/c mice. Vaccine. 2007;25:1409-1415.

Luo Y, Zhou H, Mizutani M et al. A DNA vaccine targeting Fos-related antigen 1 enhanced by IL-18 induces long-lived T-cell memory against tumor recurrence. Cancer Res. 2005;65:3419-3427.

Luo, X., Li, Z., Lin, S., Le, T., Ittensohn, M., Bermudes, D., Runyab, J. D., Shen, S. Y., Chen, J., King, I. C., and Zheng, L. M. Antitumor effect of VNP20009, an attentuated *Salmonella,* in murine tumor models. Oncol Res. 12: 501-508, 2001.

Macchiarulo A, Camaioni E, Nuti R, Pellicciari R. Highlights at the gate of tryptophan catabolism: a review on the mechanisms of activation and regulation of indoleamine 2,3-dioxygenase (IDO), a novel target in cancer disease. Amino Acids. 2009;37:219-229.

Maeurer, M.J. et al. Tumor escape from immune recognition; lethal recurrent melanoma in a patient associated with downregulation of the peptide transporter protein TAP-1 and loss of expression of the immunodominant MART-1/Melan-A antigen. J Clin Invest 98, 1633-1641 (1996).

Mandruzzato, S., et al. IL4Ralpha+ myeloid-derived suppressor cell expansion in cancer patients. J Immunol 182, 6562-6568 (2009).

Mantovani A, Savino B, Locati M et al. The chemokine system in cancer biology and therapy. Cytokine Growth Factor Rev. 2010;21:27-39.

Manuel ER, Blache CA, Paquette R et al. Enhancement of Cancer Vaccine Therapy by Systemic Delivery of a Tumor Targeting *Salmonella*-based STAT3 shRNA Suppresses the Growth of Established Melanoma Tumors. Cancer Res. 2011;71:4183-4191.

Marigo I, Dolcetti L, Serafini P, Zanovello P, Bronte V. Tumor-induced tolerance and immune suppression by myeloid derived suppressor cells. Immunol Rev. 2008; 222:162-179.

Mazzoni, A., et al. Myeloid suppressor lines inhibit T cell responses by an NO-dependent mechanism, J Immunol 168, 689-695 (2002).

Medina-Echeverz J, Fioravanti J, Zabala M et al. Successful colon cancer eradication after chemoimmunotherapy is associated with profound phenotypic change of intratumoral myeloid cells. J Immunol. 2011;186:807-815.

Mellor A.L.& Munn D.H. Creating immune privilege: active local suppression that benefits friends, but protects foes. Nature Reviews Immunology 8, 74-80 (2008).

Mellor AL, Baban B, Chandler PR et al. Cutting edge: CpG oligonucleotides induce splenic CD19+ dendritic cells to acquire potent indoleamine 2,3-dioxygenase-dependent T cell regulatory functions via IFN Type 1 signaling. J Immunol. 2005;175:5601-5605.

Mellor AL, Munn DH, IDO expression by dendritic cells: tolerance and tryptophan catabolism. Nat Rev Immunol. 2004;4:762-774.

Mellor AL, Sivakumar J, Chandler P et al. Prevention of T cell-driven complement activation and inflammation by tryptophan catabolism during pregnancy. Nat Immunol. 2001;2:64-68.

Metz R, DuHadaway JB, Kamasani U et al. Novel tryptophan catabolic enzyme IDO2 is the preferred biochemical target of the antitumor indoleamine 2,3-dioxygenase inhibitory compound D-1-methyl-tryptophan. Cancer Res. 2007;67:7082-7087.

Molon, B., et al. Chemokine nitration prevents intratumoral infiltration of antigen-specific T cells. J Exp Med 208, 1949-1962 (2011).

Movahedi, K., et al. Identification of discrete tumor-induced myeloid-derived suppressor cell subpopulations with distinct T cell-suppressive activity. Blood 111, 4233-4244 (2008).

Muller AJ, DuHadaway JB, Donover PS, Sutanto-Ward E, Prendergast GC. Inhibition of indoleamine 2,3-dioxygenase, an immunoregulatory target of the cancer suppression gene Bin1, potentiates cancer chemotherapy. Nat Med. 2005;11:312-319.

Muller AJ, DuHadaway JB, Jaller D et al. Immunotherapeutic suppression of indoleamine 2,3-dioxygenase and tumor growth with ethyl pyruvate. Cancer Res. 2010;70:1845-1853.

Muller AJ, Sharma MD, Chandler PR et al. Chronic inflammation that facilitates tumor progression creates local immune suppression by inducing indoleamine 2,3 dioxygenase. Proc Natl Acad Sci U S A. 2008;105:17073-17078.

Munder, M., et al. Th1/Th2-regulated expression of arginase isoforms in murine macrophages and dendritic cells. J Immunol 163, 3771-3777 (1999).

Munn D.H. & Mellor A.L., Indoleamine 2,3-dioxygenase and tumor-induced tolerance. J Clin Invest 117:1147-1154 (2007).

Munn DH, Sharma MD, Baban B et al. GCN2 kinase in T cells mediates proliferative arrest and anergy induction in response to indoleamine 2,3-dioxygenase. Immunity. 2005; 22:633-642.

Munn DH, Sharma MD, Hou D et al. Expression of indoleamine 2,3-dioxygenase by plasmacytoid dendritic cells in tumor-draining lymph nodes. J Clin Invest. 2004;114:280-290.

Munn DH, Zhou M, Attwood JT et al. Prevention of allogeneic fetal rejection by tryptophan catabolism. Science. 1998; 281:1191-1193.

Nagaraj, S., et al. Altered recognition of antigen is a mechanism of CD8+ T cell tolerance in cancer. Nat Med 13, 828-835 (2007).

Nemunaitis J, Cunningham C, Senzer N et al. Pilot trial of genetically modified attenuated *Salmonella* expressing the *E. coli* cytosine deaminase gene in refractory cancer patients. Cancer Gene Ther. 2003; 10:737-744.

Nishikawa H, Sato E, Briones G et al. In vivo antigen delivery by a *Salmonella typhimurium* type III secretion system for therapeutic cancer vaccines. J Clin Invest. 2006;116:1946-1954.

Norian, L. A., Rodriguez, P. C., O'Mara, L. A., Zabaleta, J., Ochoa, A. C., Cella, M., and Allen, P. M. Tumor-infiltrating regulatory dendritic cells inhibit CD8+ T cell function via Larginine metabolism. Cancer Res, 69: 3086-3094, 2009.

Ostrand-Rosenberg, S. & Sinha, P. Myeloid-derived suppressor cells: linking inflammation and cancer. J Immunol 182, 4499-4506 (2009).

Pan, P.Y., et al. Immune stimulatory receptor CD40 is required for T-cell suppression and T regulatory cell activation mediated by myeloid-derived suppressor cells in cancer. Cancer Res 70, 99-108 (2010).

Paschen, A. et al. Complete loss of HLA class I antigen expression on melanoma cells: a result of successive mutational events. Int J Cancer 103, 759-767 (2003).

Pascolo, S., Bervas, N., Ure, J. M., Smith, A. G., Lemonnier, F. A., and Perarnau, B. HLA-A2.1-restricted education and cytolytic activity of CD8(+) T lymphocytes from beta2 microglobulin (beta2m) HLA-A2.1 monochain transgenic H-2Db beta2m double knockout mice. J Exp Med, 185: 2043-2051, 1997.

Pawelek, J.M., Low, K.B. & Bermudes, D. Bacteria as tumour-targeting vectors. Lancet Oncol 4, 548-556 (2003).

Pawelek, J.M., Low, K.B. & Bermudes, D. Tumor-targeted *Salmonella* as a novel anticancer vector. Cancer Res 57, 4537-4544 (1997).

Pensa, S. et al., STAT1 and STAT3 in Tumorigenesis: Two Sides of the Same Coin? In JAK-STAT Pathway in Disease 100-121 (Anastasis Stephanou, ed., Landes Bioscience 2009).

Polak, M. E., Borthwick, N. J., Jager, M. J., and Cree, I. A. Melanoma vaccinees: The problems of local immunosuppression. Hum Immunol. 70: 331-339, 2009.

Prendergast GC. Immune escape as a fundamental trait of cancer: focus on IDO. Oncogene. 2008;27:3889-3900.

Rodriguez PC, Ernstoff MS, Hernandez C et al. Arginase I-producing myeloid-derived suppressor cells in renal cell carcinoma are a subpopulation of activated granulocytes. Cancer Res. 2009;69:1553-1560.

(56) References Cited

OTHER PUBLICATIONS

Rodriguez, P.C., Quiceno, D.G., Zabeleta, J., Arginase I production in the tumor microenvironment by mature myeloid cells inhibits T-cell receptor expression and antigen-specific T-cell responses. Cancer Res 64, 5839-5849 (2004).

Rodriguez, P. C., Zea, A. H., and Ochoa, A. C. Mechanisms of tumor evasion from the immune response. Cancer Chemother Biol Response Modif, 21: 351-364, 2003.

Rosenberg SA, Restifo NP, Yang JC, Morgan RA, Dudley ME. Adoptive cell transfer: a clinical path to effective cancer immunotherapy. Nat Rev Cancer. 2008; 8:299-308.

Rosenberg, S. A., Spiess, P. J., and Kleiner, D. E. Antitumor effects in mice of the intravenous injection of attenuated *Salmonella typhimurium*. J Immunother, 25: 218-225, 2002.

Rothe, G. Valet, G. Flow cytometric analysis of respiratory burst activity in phagocytes with hydroethidine and 2',7'-dichlorofluorescin. J Leukoc Biol 47, 440-448 (1990).

Russmann H, Shams H, Poblete F et al. Delivery of epitopes by the *Salmonella* type III secretion system for vaccine development. Science. 1998;281:565-568.

Ryan, B. M., O'Donovan, N., and Duffy, M. J. Survivin: a new target for anti-cancer therapy. Cancer Treat Rev, 35: 553-562, 2009.

Sakaguchi S, Wing K, Onishi Y, Prieto-Martin P, Yamaguchi T. Regulatory T cells: how do they suppress immune responses? International Immunology, 21(10):1105-1111, 2009.

Scheel-Toellner D, Wang K, Assi LK et al. Clustering of death receptors in lipid rafts initiates neutrophil spontaneous apoptosis. Biochem Soc Trans. 2004;32:679-681.

Schmielau, J. & Finn, O.J. Activated granulocytes and granulocyte-derived hydrogen peroxide are the underlying mechanism of suppression of t-cell function in advanced cancer patients. Cancer Res 61, 4756-4760 (2001).

Serafini, P., Mgebroff, S., Noonan, K. & Borrello, I. Myeloid-derived suppressor cells promote cross-tolerance in B-cell lymphoma by expanding regulatory T cells. Cancer Res 68, 5439-5449 (2008).

Sharma MD, Baban B, Chandler P et al. Plasmacytoid dendritic cells from mouse tumor-draining lymph nodes directly activate mature Tregs via indoleamine 2,3-dioxygenase. J Clin Invest. 2007;117:2570-2582.

Sharma MD, Hou DY, Liu Y et al. Indoleamine 2,3-dioxygenase controls conversion of Foxp3+ Tregs to TH17-like cells in tumor-draining lymph nodes. Blood. 2009;113:6102-6111.

Simons MP, Nauseef WM, Griffith TS. Neutrophils and TRAIL: insights into BCG immunotherapy for bladder cancer. Immunol Res. 2007;39:79-93.

Simons MP, O'Donnell MA, Griffith TS. Role of neutrophils in BCG immunotherapy for bladder cancer. Urol Oncol. 2008;26:341-345.

Sinha, P., Clements, V.K., Bunt, S.K., Albelda, S.M. & Ostrand-Rosenberg, S. Crosstalk betwen myeloid-derived suppressor cells and macrophages subverts tumor immunity toward a type 2 response. J Immunol 179, 977-983 (2007).

Soliman H, Mediavilla-Varela M, Antonia S. Indoleamine 2,3-dioxygenase: is it an immune suppressor? Cancer J. 2010;16:354-359.

Sorenson RB, Berge-Hansen L, Junker N et al. The immune system strikes back: cellular immune responses against indoleamine 2,3-dioxygenase. PLoS ONE. 2009;4:e6910.

Sorenson RB, Harup SR, Svane IM et al. Indoleamine 2,3-dioxygenase specific, cytotoxic T cells as immune regulators. Blood. 2011;117:2200-2210.

Sorensen RB, Kollgaard T, Andersen RS et al. Spontaneous Cytotoxic T-Cell Reactivity against Indoleamine 2,3-Dioxygenase-2. Cancer Res. 2011;71:2038-2044.

Srikanth CV, Wall DM, Maldonado-Contreras A et al. *Salmonella* pathogenesis and processing of secreted effectors by caspase-3. Science. 2010;330:390-393.

Stockmeyer, B. et al. Polymorphonuclear granulocytes induce antibodydependent apoptosis in human breast cancer cells. J Immunol 171, 5124-5129 (2003).

Suttmann H, Riemensberger J, Bentien G et al. Neutrophil granulocytes are required for effective Bacillus Calmette-Guerin immunotherapy of bladder cancer and orchestrate local immune responses. Cancer Res. 2006;66:8250-8257.

Tepper RI, Coffman RL, Leder P. An eosinophil-dependent mechanism for the antitumor effect of interleukin-4, Science. 1992;257:548-551.

Terabe, M. & Berzofsky, J.A. NKT cells in immunoregulation of tumor immunity: a new immunoregulatory axis. Trends Immunol 28, 491-496 (2007).

Theys, J., Barbe, S., Landuyt, W., Nuyts, S., Van Mellaert, L., Wouters, B., Anne, J., and Lambin, P. Tumor-specific gene delivery using genetically engineered bacteria. Curr Gene Ther, 3: 207-221, 2003.

Tomihara K, Guo M, Shin T et al. Antigen-specific immunity and cross-priming by epithelial ovarian carcinoma-induced CD11b(+)Gr-1(+) cells. J Immunol. 2010; 184:6151-6160.

Toso, J.F. et al. Phase I study of the intravenous administration of attenuated *Salmonella typhimurium* to patients with metastatic melanoma. J Clin Oncol 20, 142-152 (2002).

Tran, J., Rak, J., Sheehan, C., Saibil, S. D., LaCasse, E., Korneluk, R. G., and Kerbel, R. S. Marked induction of the IAP family antiapoptotic proteins survivin and XIAP by VEGF in vascular endothelial cells. Biochem Biophys Res Commun, 264:781-788, 1999.

Tsunetsugu-Yokota, Y., Ishige, M., and Murakami, M. Oral attenuated *Salmonella enterica* serovar Typhimurium vaccine expressing codon-optimized HIV type 1 Gag enhanced intestinal immunity in mice. AIDS Res Hum Retroviruses, 23: 278-286, 2007.

Uyttenhove, C., Pilotte, L., Theate, I., Stroobant, V., Colau, D., Parmentier, N., Boon, T., and Van den Eynde, B. J. Evidence for a tumoral immune resistance mechanism based on tryptophan degradation by indoleamine 2,3-dioxygenase. Nat Med, 9:1269-1274, 2003.

Van der Sluijs, K., Singh, R., Dijkhuis, A., Snoek, M., and Lutter, R. Indoleamine 2,3-dioxygenase activity induces neutrophil apoptosis. Critical Care 15, 208 (2011).

Vitiello A, Marchesini D, Furze J, Sherman LA, Chesnut RW. Analysis of the HLA-restricted influenza-specific cytotoxic T lymphocyte response in transgenic mice carrying a chimeric human-mouse class I major histocompatibility complex. J Exp Med. 1991;173:1007-1015.

Wang LC, Thomsen L, Sutherland R et al. Neutrophil influx and chemokine production during the early phases of the antitumor response to the vascular disrupting agent DMXAA (ASA404). Neoplasia. 2009;11:793-803.

Wang, J. & Yi, J. Cancer cell killing via ROS: to increase or decrease, that is the question. Cancer Biol Ther 7, 1875-1884 (2008).

Wang, T., Niu, G., Kortylewski, M., Burdelya, L., Shain, K., Zhang, S., Bhattacharya, R., Gabrilovich, D., Heller, R., Coppola, D., Dalton, W., Jove, R., Pardoll, D., and Yu, H. Regulation of the innate and adaptive immune responses by Stat-3 signaling in tumor cells. Nat Med, 10:48-54, 2004.

Westphal K, Leschner S, Jablonska J, Loessner H, Weiss S. Containment of tumorcolonizing bacteria by host neutrophils. Cancer Res. 2008;68:2952-2960.

Whiteside, T. L. The tumor microenvironment and its role in promoting tumor growth. Oncogene, 27: 5904-5912, 2008.

Wick MJ. Living in the danger zone: innate immunity to *Salmonella*. Curr Opin Microbiol. 2004;7:51-57.

Witkiewicz AK, Costantino CL, Metz R et al. Genotyping and expression analysis of IDO2 in human pancreatic cancer: a novel, active target. J Am Coll Surg. 2009;208:781-787.

Wright HL, Moots RJ, Bucknall RC, Edwards SW. Neutrophil function in inflammation and inflammatory diseases. Rheumatology (Oxford). 2010;49:1618-1631.

Xia, Y., Roman, L.J. Masters, B.S. & Zweier, J.L. Inducible nitric-oxide synthase generates superoxide from the reductase domain. J Biol Chem 273, 22635-22639 (1998).

(56) References Cited

OTHER PUBLICATIONS

Xia, Y. & Zweier, J.L. Superoxide and peroxynitrite generation from inducible nitric oxide synthase in macrophages. Proc Natl Acad Sci U S A 94, 6954-6958 (1997).

Xiang R, Primus FJ. Ruehlmann JM et al. A dual-function DNA vaccine encoding carcinoembryonic antigen and CD40 ligand trimer inducers T cell-mediated protective immunity against colon cancer in carcinoembryonic antigen-transgenic mice. J Immunol. 2001;167:4560-4565.

Xiang, R., Luo, Y., Niethammer, A. G., and Reisfeld, R. A. Oral DNA vaccines target the tumor vasculature and microenvironment and suppress tumor growth and metastasis. Immunol Rev, 222: 117-128, 2008.

Xiang, R., Mizutani, N., Luo, Y., Chiodoni, C., Zhou, H., Mizutani, M., Ba, Y., Becker, J.C., and Reisfeld, R. A. A DNA vaccine targeting survivin combines apoptosis with suppression of angiogenesis in lung tumor eradication. Cancer Res, 65: 553-561, 2005.

Xiong, G., Husseiny, M. I., Song, L., Erdreich-Epstein, A., Shackleford, G. M., Seeger, R.C. Jackel, D., Hensel, M., and Metelitsa, L. S. Novel cancer vaccine based on genes of *Salmonella* pathogenicity island 2. Int J Cancer, 126: 2622-2634, 2009.

Xu, D. Q., Zhang, L., Kopecko, D. J., Gao, L., Shao, Y., Guo, B., and Zhao, L. Bacterial delivery of siRNAs: a new approach to solid tumor therapy. Methods Mol Biol, 487: 161-187, 2009.

Yamashiro S, Kamohara H, Wang JM et al. Phenotypic and functional change of cytokineactivated neutrophils: inflammatory neutrophils are heterogeneous and enhance adaptive immune responses. J Leukoc Biol. 2001;69:698-704.

Yang L, Pang Y, Moses HL, TGF-beta and immune cells: an important regulatory axis in the tumor microenvironment and progression. Trends Immunol. 2010;31:220-227.

Yen MC, Lin CC, Chen YL et al. A Novel cancer therapy by skin delivery of indoleamine 2,3-dioxygenase siRNA. Clin Cancer Res. 2009;15:641-649.

Yin, K., Liu, Q., Zhu, S., and Yan, G. Adenovirus-mediated siRNA inhibited survivin gene expression induces tumor cell apoptosis in nude mice. Biosci Trends, 2: 231-234, 2008.

Youn, J.I., Collazo, M., Shalova, I.N., Biswas, S.K. & Gabrilovich, D.I. Characterization of the nature of granulocytic myeloid-derived suppressor cells in tumor-bearing mice. J Leukoc Biol 91, 167-181 (2012).

Youn, J.I., Nagaraj, S., Collazo, M. & Gabrilovich, D.I. Subsets of myeloid-derived suppressor cells in tumor-bearing mice. J Immunol 181, 5791-5802 (2008).

Yu, H., Kortylewski, M., and Pardoll, D. Crosstalk between cancer and immune cells: role of STAT3 in the tumour microenvironment. Nat Rev Immunol, 7: 41-51, 2007.

Zhang, L., Gao, L., Zhao, L., Guo, B., Ji, K., Tian, Y., Wang, J., Yu, H., Hu, J., Kalvakolanu, D. V. Kopecko, D. J., Zhao, X., and Xu, D. Q. Intratumoral delivery and suppression of prostate tumor growth by attenuated *Salmonella enterica* serovar typhimurium carrying plasmid-based small interfering RNAs. Cancer Res, 67:5859-5864, 2007.

Zhang, Y., Chen, Z. D., Du, C. J., Xu, G., and Luo, W. siRNA targeting survivin inhibits growth and induces apoptosis in human renal clear cell carcinoma 786-O cells. Pathol Res Pract, 205: 823-827, 2009.

Zhao M, Yang M, Li XM et al. Tumor-targeting bacterial therapy with amino acid auxotrophs of GFP-expressing *Salmonella typhimurium*. Proc Natl Acad Sci U S A. 2005;102:755-760.

Zhao M, Yang M, Ma H et al. Targeted therapy with a *Salmonella typhimurium* leucinearginine auxotroph cures orthotopic human breast tumors in nude mice. Cancer Res. 2006;66:7647-7652.

Zheng, X., Koropatnick, J., Li, M., Zhang, X., Ling, F., Ren, X., Hao, X., Sun, H., Vladau, C., Franek, J. A., Feng, B., Urquhart, B. L. Zhong, R., Freeman, D. J., Garcia, B., and Min, W. P. Reinstalling antitumor immunity by inhibiting tumor-derived immunosuppressive molecule IDO and through RNA interference. J Immunol, 177: 5639-5656, 2006.

Zhou, H., Luo, Y., Kaplan, C. D., Kruger, J. A., Lee, S. H., Xiang, R., and Reisfeld, R. A. A DNA-based cancer vaccine enhances lymphocyte cross talk by engaging the NKG2D receptor. Blood, 107: 3251-3257, 2006.

Zhu G, Augustine MM, Azuma T et al. B7-H4-deficient mice display augmented neutrophilmediated innate immunity. Blood. 2009;113:1759-1767.

Zivkovic, M. et al. Oxidative burst and anticancer activities of rat neutrophils. Biofactors 24, 305-312 (2005).

\* cited by examiner

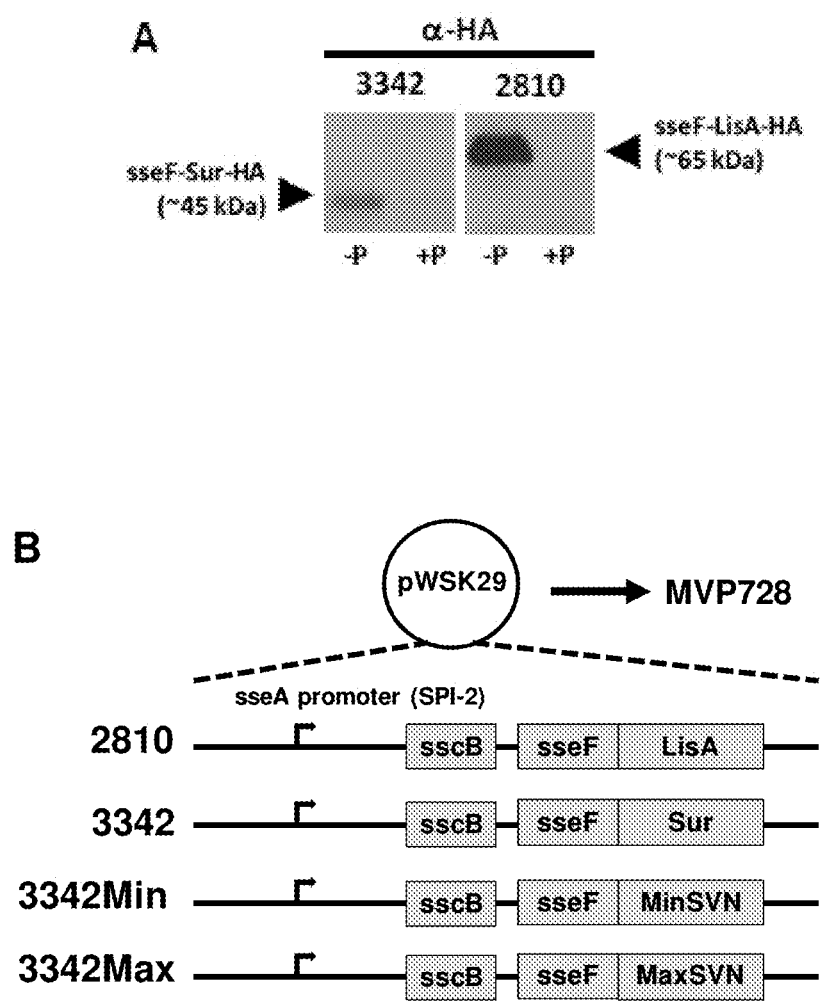
Figure 6A-B

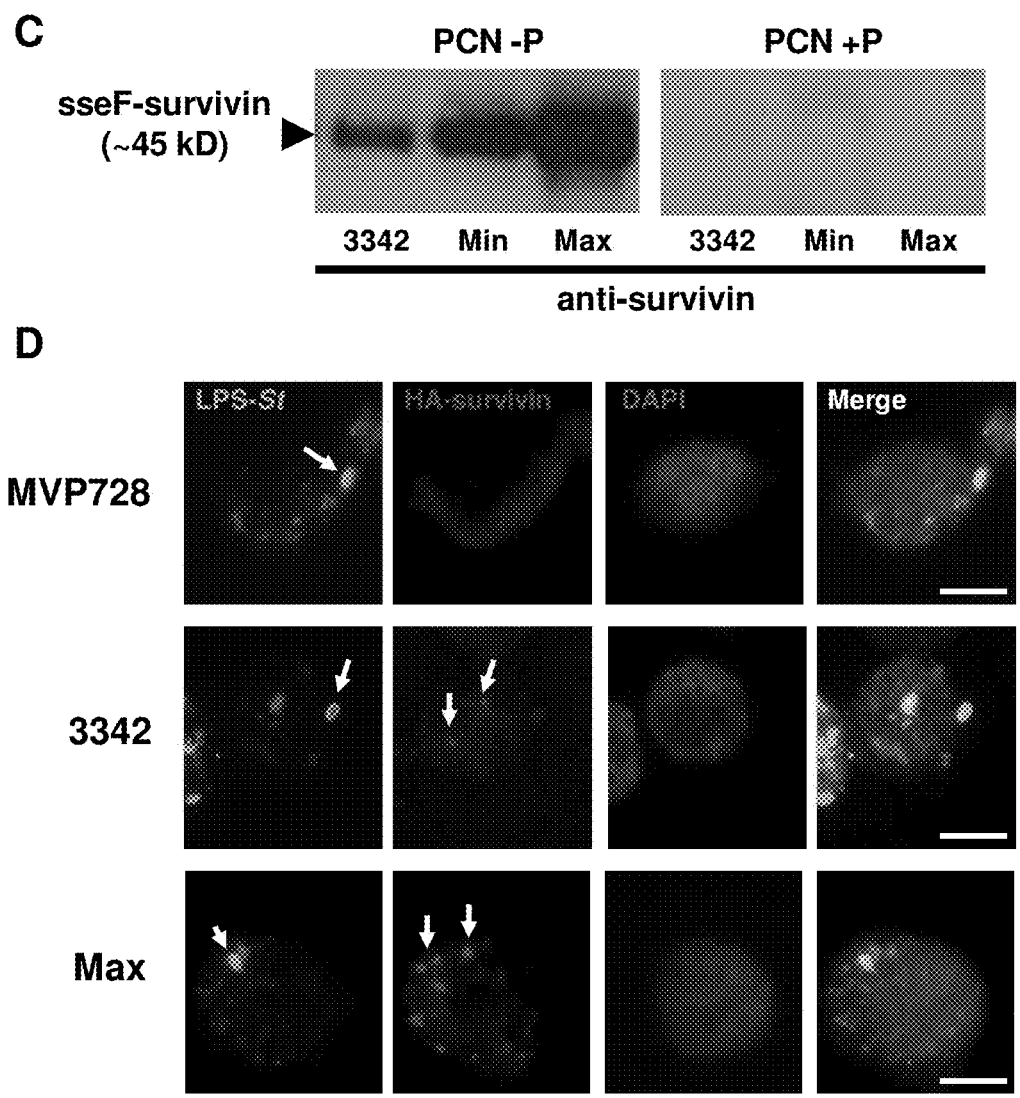
Figure 6C-D

**3342Max: Maximally *S.typhimurium* codon optimized (CO)-hSur sequence for insertion into pWSK29 backbone plasmid, with maximally codon optimized HA-tag:**

EcoRV gat atc ggc gcg ccg acc ctg ccg ccg gcg tgg cag ccg ttc ctg aaa gac cac
cgt atc tct acc ttc aaa aac tgg ccg ttc ctg gaa ggc tgc gcg tgc acc ccg
gaa cgt atg gcg gaa gcg ggc ttc atc cac tgc ccg acc gaa aac gaa ccg gac
ctg gcg cag tgc ttc ttc tgc ttc aaa gaa ctg gaa ggc tgg gaa ccg gac gac
gac ccg atc gaa gaa cac aaa aaa cac tct tct ggc tgc gcg ttc ctg tct gtt
aaa aaa cag ttc gaa gaa ctg acc ctg ggc gaa ttc ctg aaa ctg gac cgt gaa
cgt gcg aaa aac aaa atc gcg aaa gaa acc aac aac aaa aaa aaa gaa ttc gaa
gaa acc gcg aaa aaa gtt cgt cgt gcg atc gaa cag ctg gcg gcg atg gac tac
ccg tac gac gtt ccg gac tac gcg taa tct aga codon optimized HA-tag (highlighted) stop XbaI

Amino acid translation:

Maximally codon optimized:

GAPTLPPAWQPFLKDHRISTFKNWPFLEGCACTPERMAEAGFIHCPTENEPDLAQCFFCFKELEGWEPD
DDPIEEHKKHSSGCAFLSVKKQFEELTLGEFLKLDRERAKNKIAKETNNKKKEFEETAKKVRRAIEQLA
AMDYPYDVPDYAstop

Figure 18

**3342MinL Minimally *S.typhimurium* codon optimized hSur sequence for insertion into pWSK29 plasmid, with maximally codon optimized HA-tag:**

EcoRV
gat atc ggt gcc ccg acg ttg CCG cct gcc tgg cag CCG ttt ctc aag gac cac
cgc atc tct aca ttc aag aac tgg CCG ttc ttg gag ggc tgc gcc tgc acc ccg
gag cgg atg gcc gag gct ggc ttc atc cac tgc CCG act gag aac gag cca gac
ttg gcc cag tgt ttc ttc tgc ttc aag gag ctg gaa ggc tgg gag cca gat gac
gac CCG ATC gag gaa cat aaa aag cat tcg tcc ggt tgc gct ttc ctt tct gtc
aag aag cag ttt gaa gaa tta acc ctt ggt gaa ttt ttg aaa ctg gac CGT gaa
CGT gcc aag aac aaa att gca aag gaa acc aac aat aag aag aaa gaa ttt gag
gaa act gcg aag aaa gtg cgc cgt gcc atc gag cag ctg gct gct atg gat tac
ccg tac gac gtt ccg gac tac gcg taa tct aga codon optimized HA-tag (highlighted)   stop   XbaI

Amino acid translation:

Minimally codon optimized:

GAPTLPPAWQPFLKDHRISTFKNWPFLEGCACTPERMAEAGFIHCPTENEPDLAQCFFCFKELEGWEPD
DDPIEEHKKHSSGCAFLSVKKQFEELTLGEFLKLDRERAKNKIAKETNNKKKEFEETAKKVRRAIEQLA
AMDYPYDVPDYAstop

Figure 19

3342: Non-codon optimized sequence (start and stop codon deleted from hSur):

EcoRV gat atc ggt gcc ccg acg ttg ccc cct gcc tgg cag ccc ttt ctc aag gac cac cgc atc tct aca ttc aag aac tgg ccc ttc ttg gag ggc tgc gcc tgc acc ccg gag cgg atg gcc gag gct ggc ttc atc cac tgc ccc act gag aac gag cca gac ttg gcc cag tgt ttc ttc tgc ttc aag gag ctg gaa ggc tgg gag cca gat gac gac ccc ata gag gaa cat aaa aag cat tcg tcc ggt tgc gct ttc ctt tct gtc aag aag cag ttt gaa gaa tta acc ctt ggt gaa ttt ttg aaa ctg gac aga gaa aga gcc aag aac aaa att gca aag gaa acc aac aat aag aag aaa gaa ttt gag gaa act gcg aag aaa gtg cgc cgt gcc atc gag cag ctg gct gct atg gat ==tac cca tac gac gtc cca gac tac gct== taa tct aga

HA-tag (highlighted)      stop      XbaI

AMINO ACID TRANSLATION:

<u>Non-codon optimized:</u>

GAPTLPPAWQPFLKDHRISTFKNWPFLEGCACTPERMAEAGFIHCPTENEPDLAQCFFCFKELEGWEPD
DDPIEEHKKHSSGCAFLSVKKQFEELTLGEFLKLDRERAKNKIAKETNNKKKEFEETAKKVRRAIEQLA
AMDYPYDVPDYAstop

Figure 20 shIDO#8
CCTCGCAATAGTAGATACTTA C T C
GGAGCGTTATCATCTATGAAT G A G shIDO#9
CGTCTCTCTATTGGTGGAAAT C T C
GCAGAGAGATAACCACCTTTA G A G shIDO#10
GCAAAGAATCTCCTGCAGAAT C T C
CGTTTCTTAGAGGACGTCTTA G A G shIDO#11
GCCCATGACATACGAGAACAT C T C
CGGGTACTGTATGCTCTTGTA G A G shIDO#12
CCAGTCCGTGAGTTTGTCATT C T C
GGTCAGGCACTCAAACAGTAA G A G scrambled shRNA
CGTGATCTTCACCGACAAGAT C T C
GCACTAGAAGTGGCTGTTCTA G A G

Figure 21

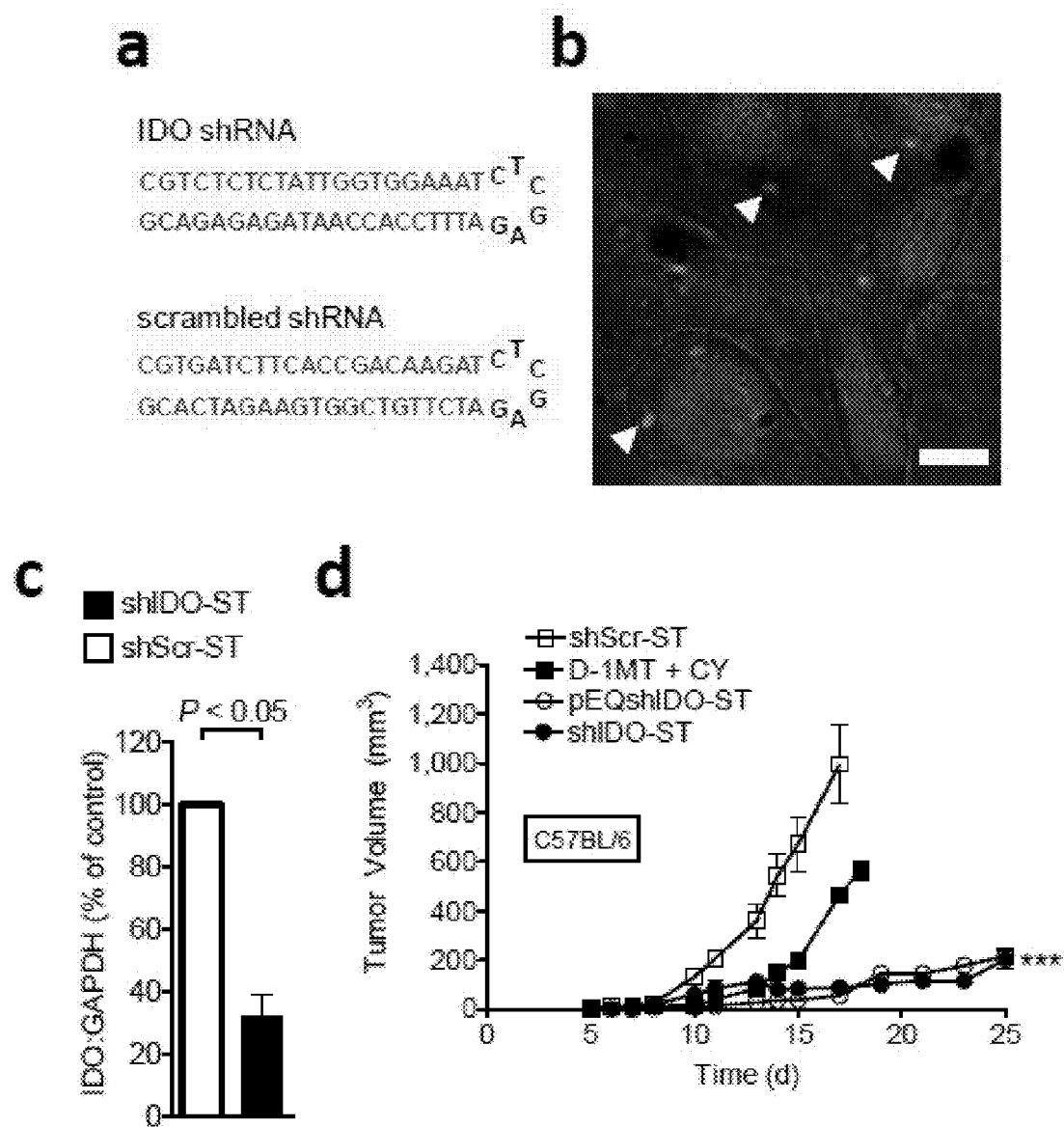
Figure 23A-D

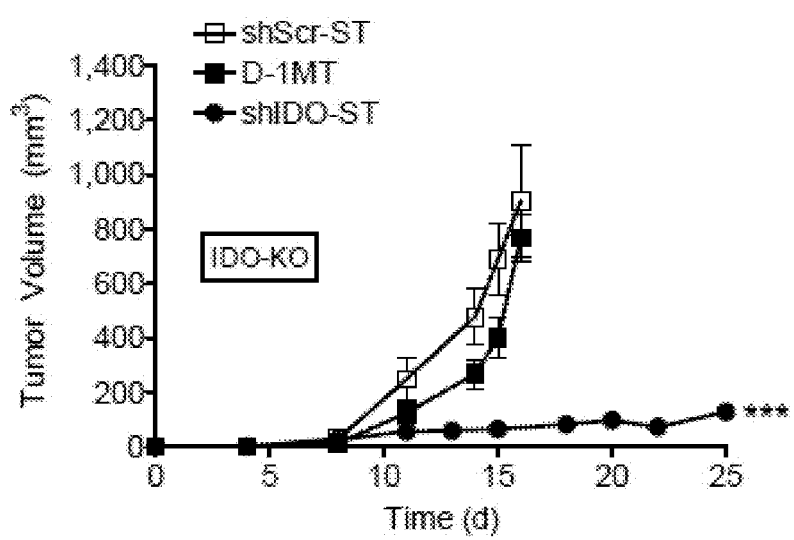
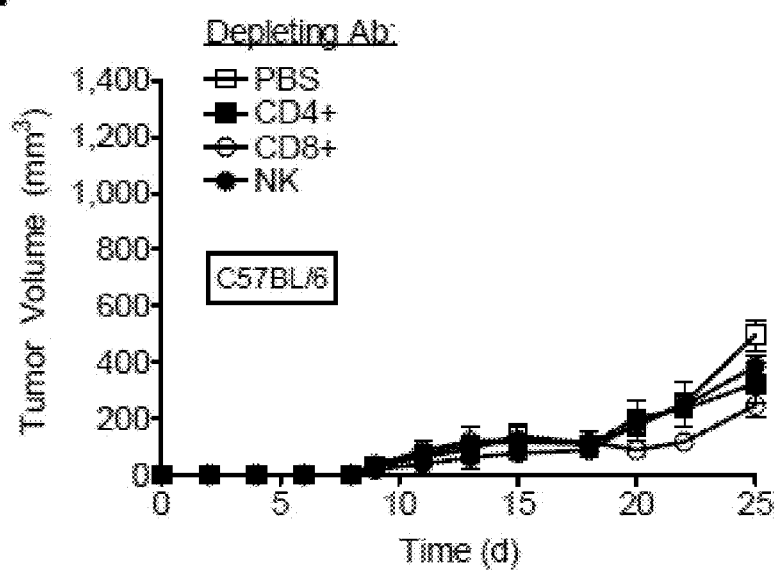
Figure 23E-F

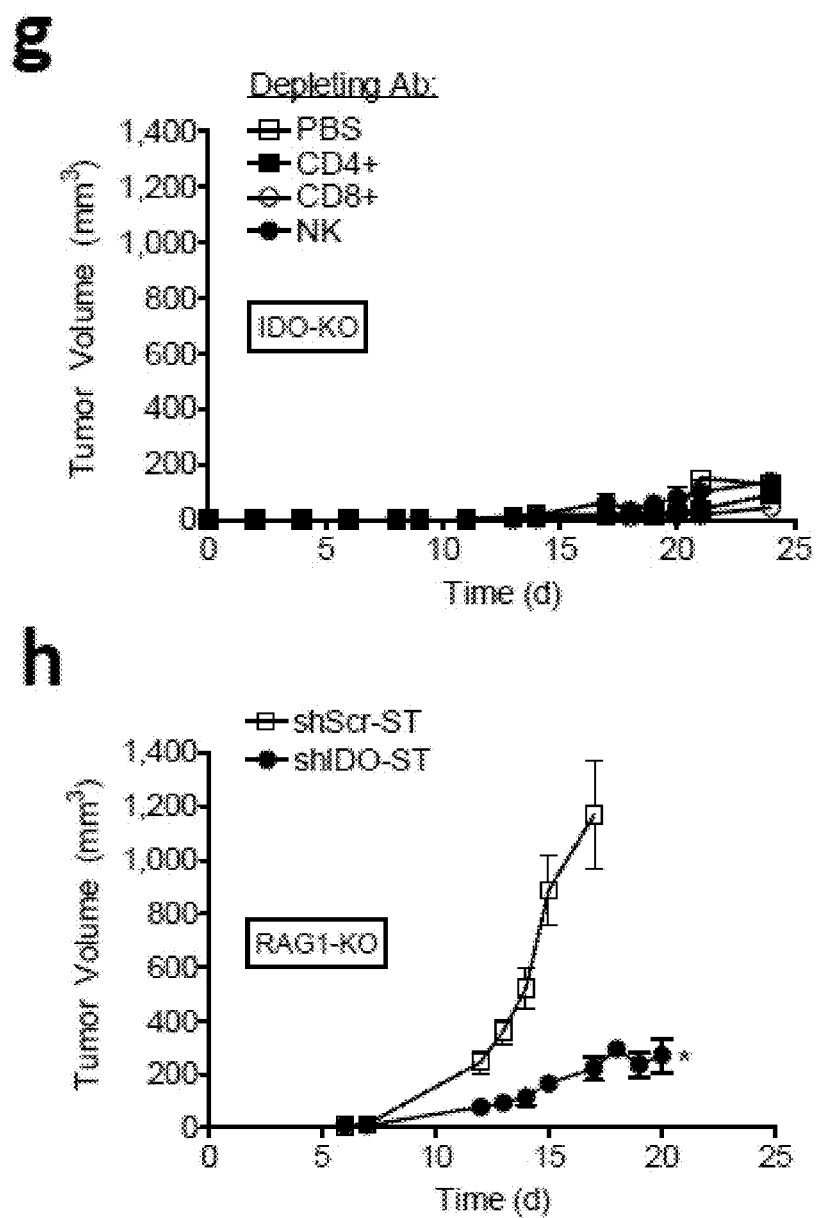
Figure 23G-H

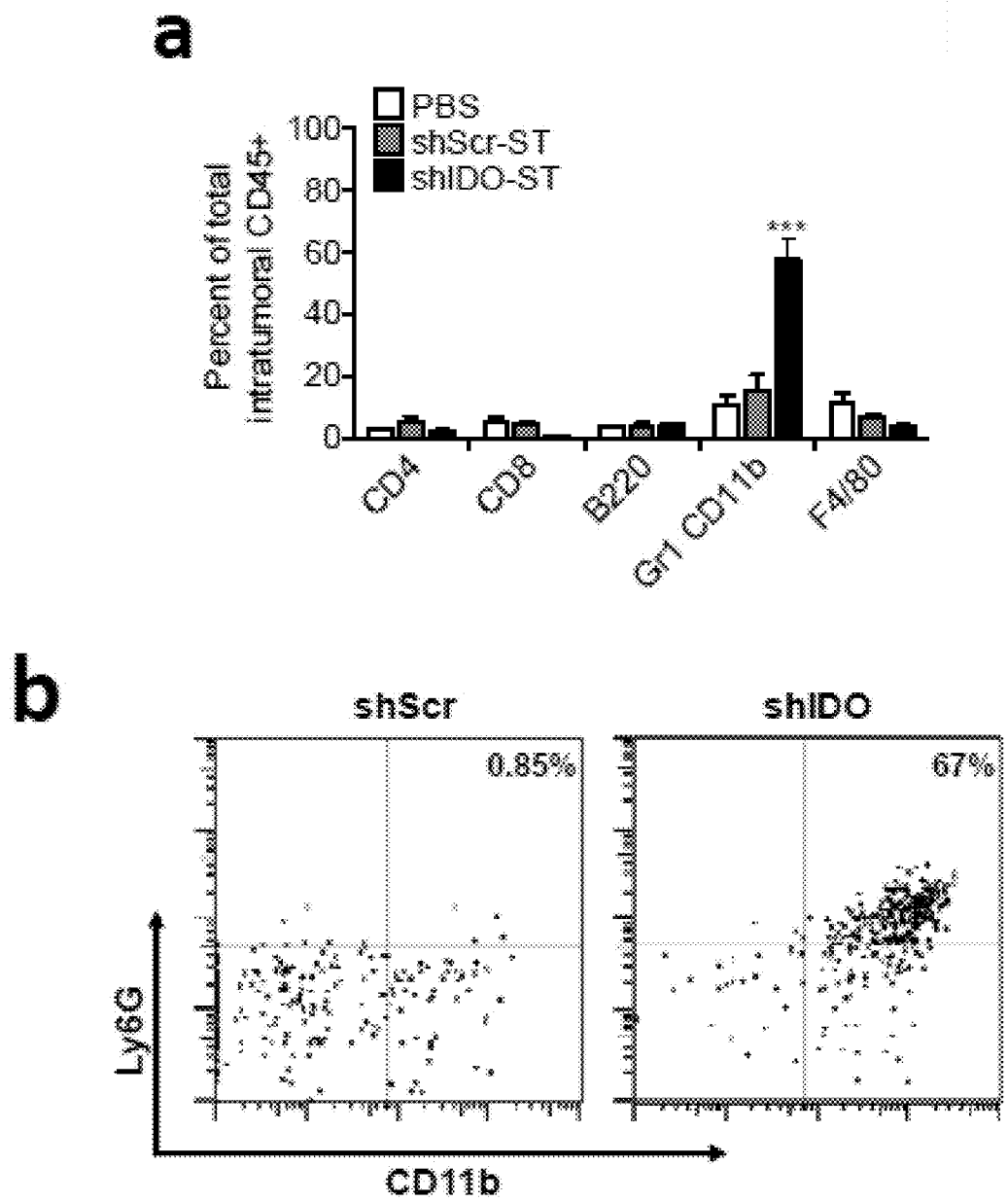
Figure 27A-B

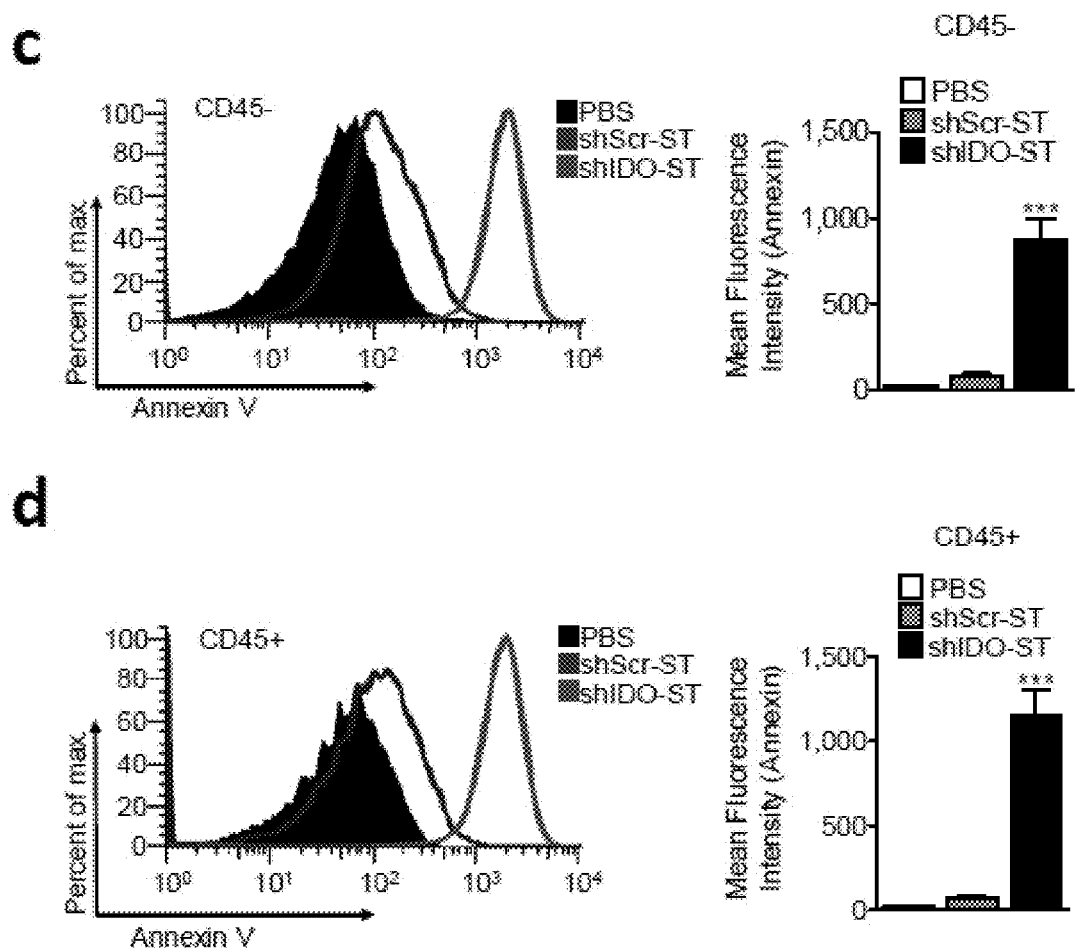
Figure 27C-D

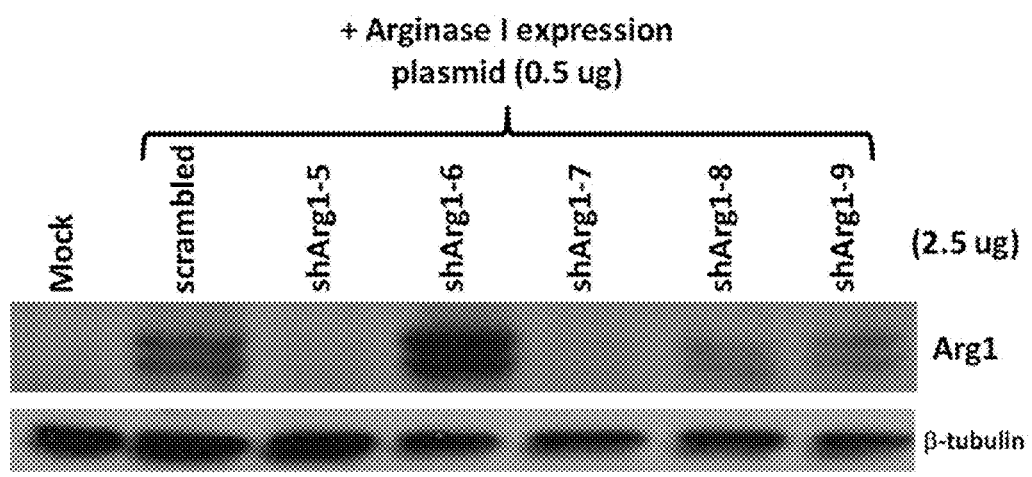
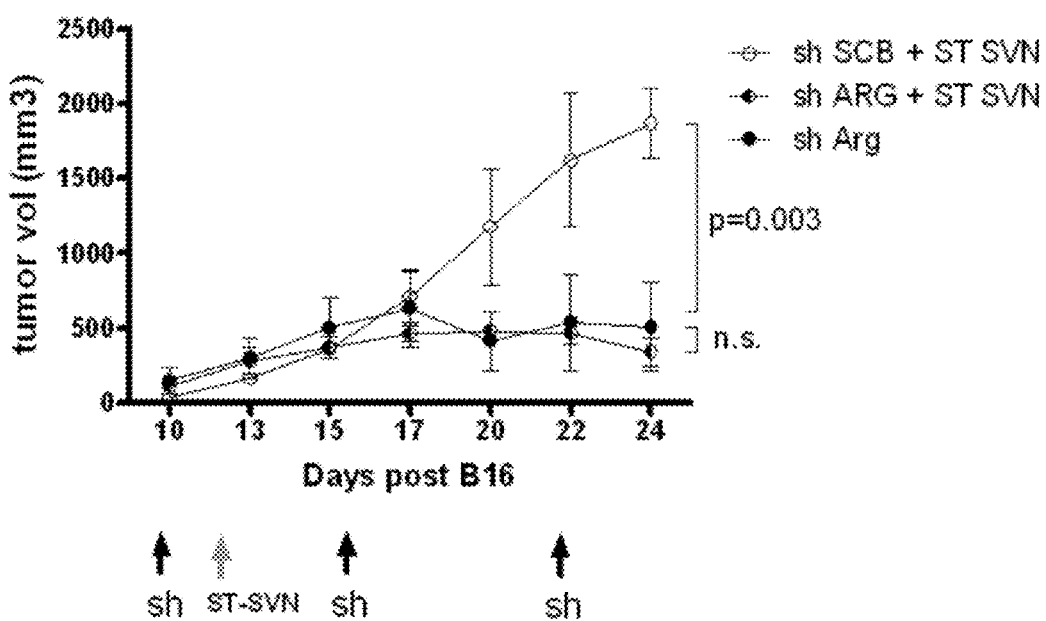
Figure 34A-B

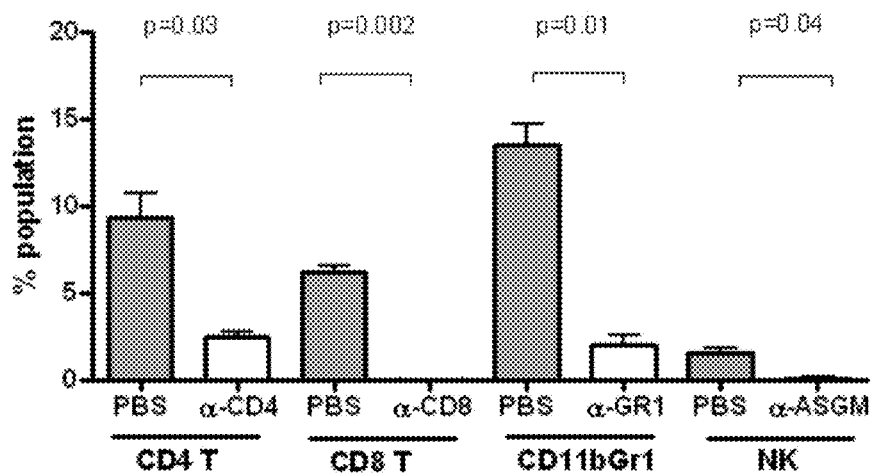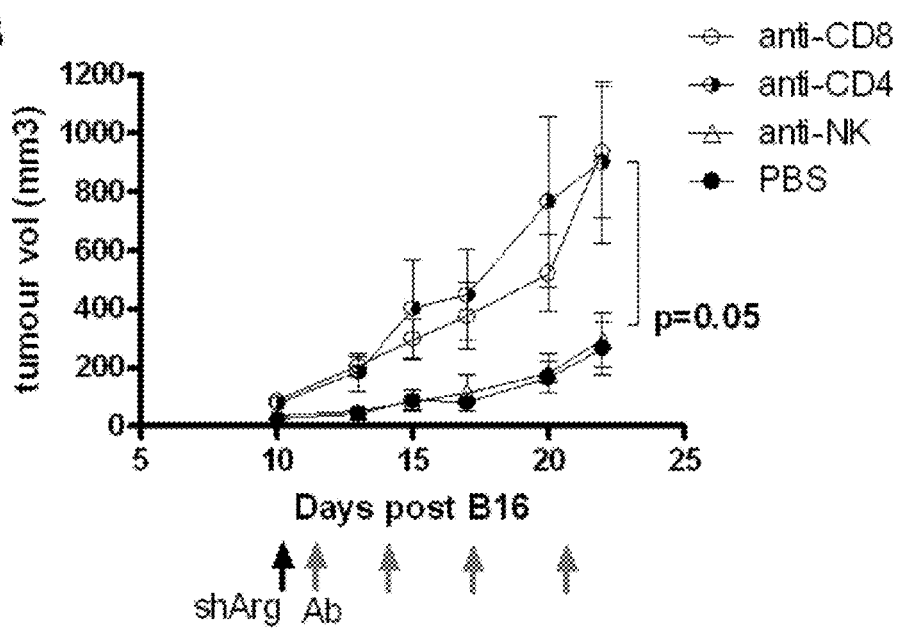
Figure 35A-B

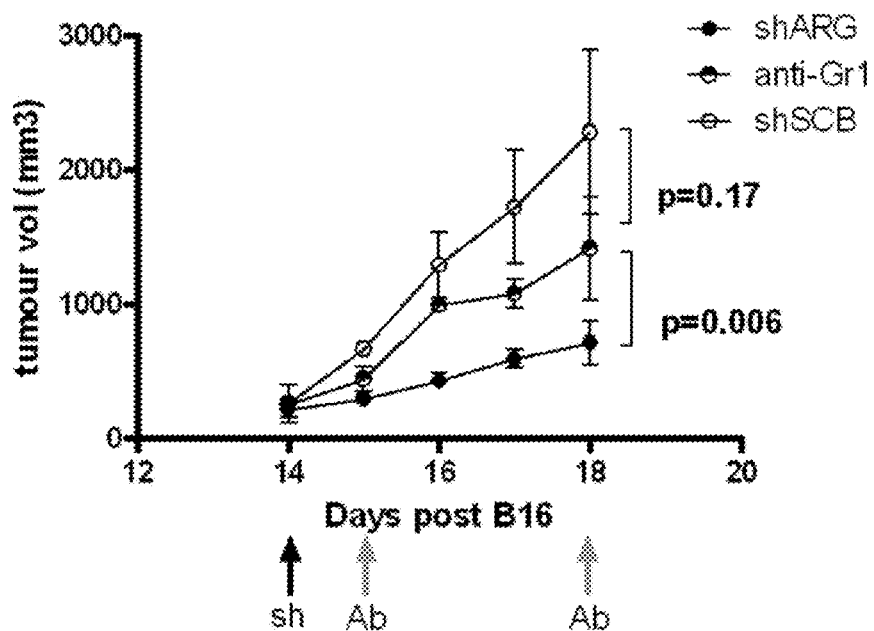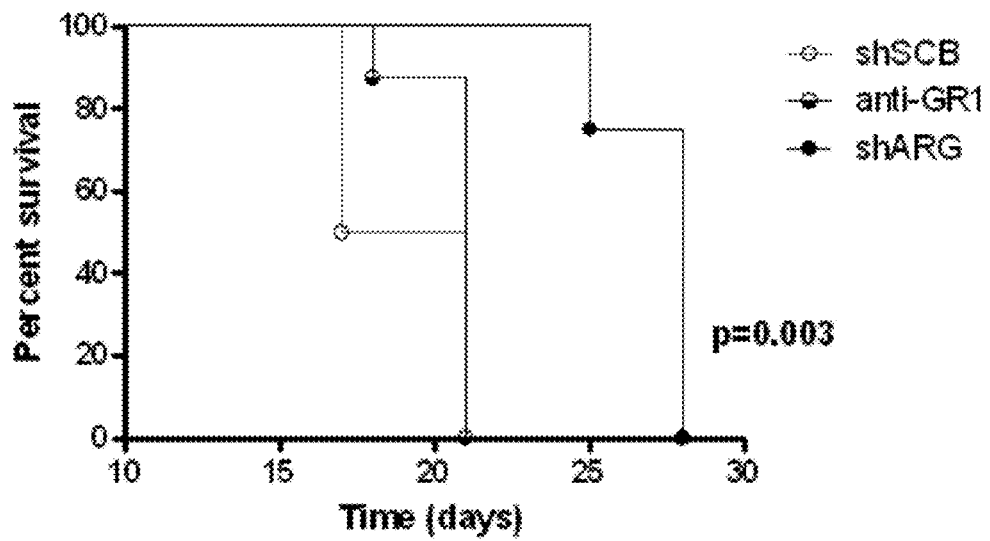
Figure 35C-D

MDSC (CD11b GR1+)    DC (CD11c+)

Arginase-I

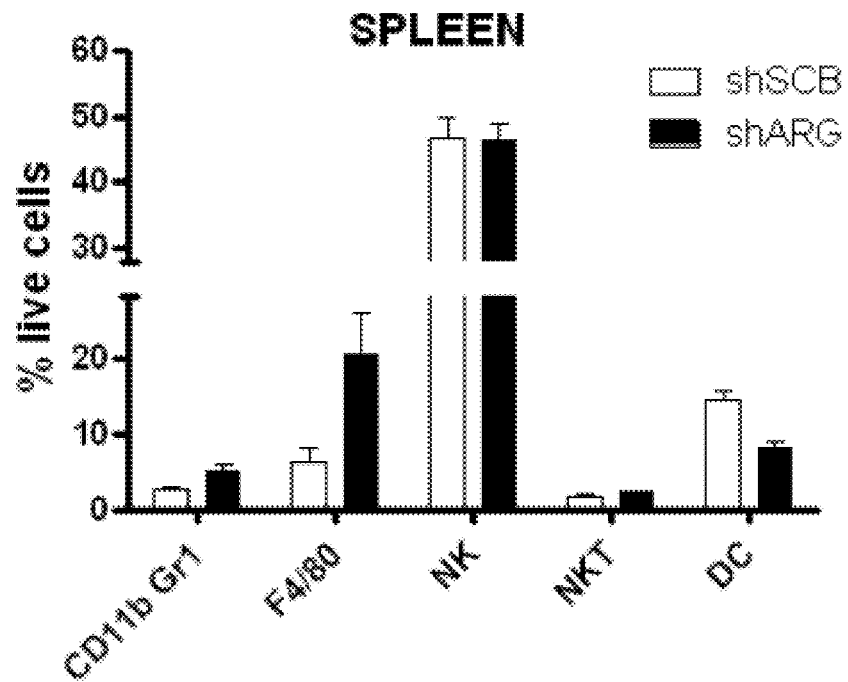
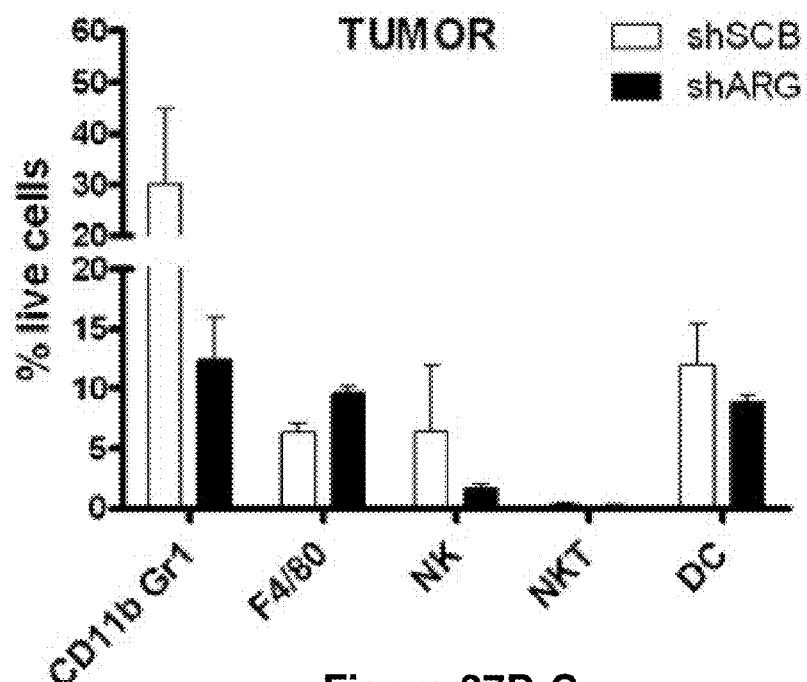
Figure 37B-C

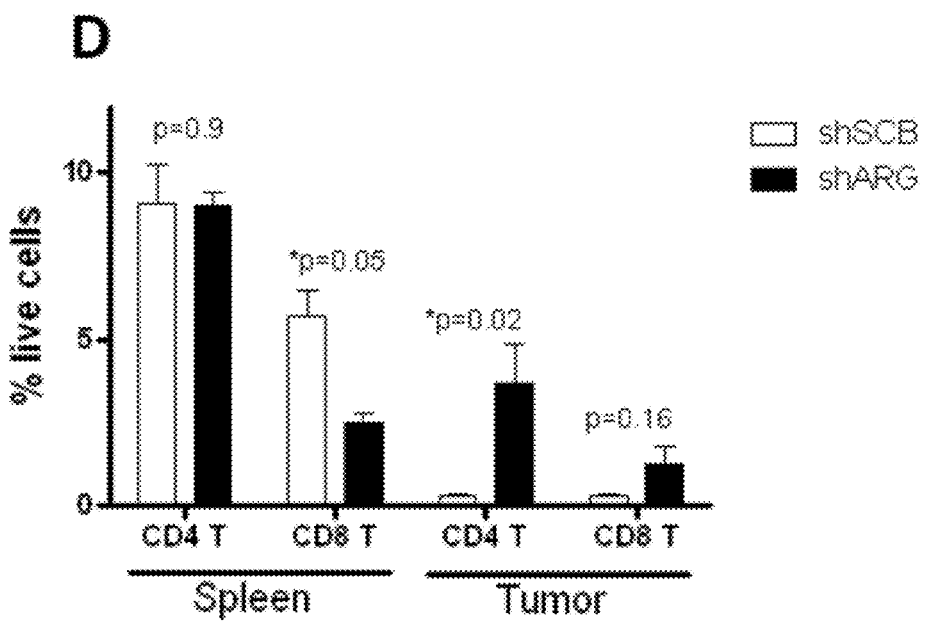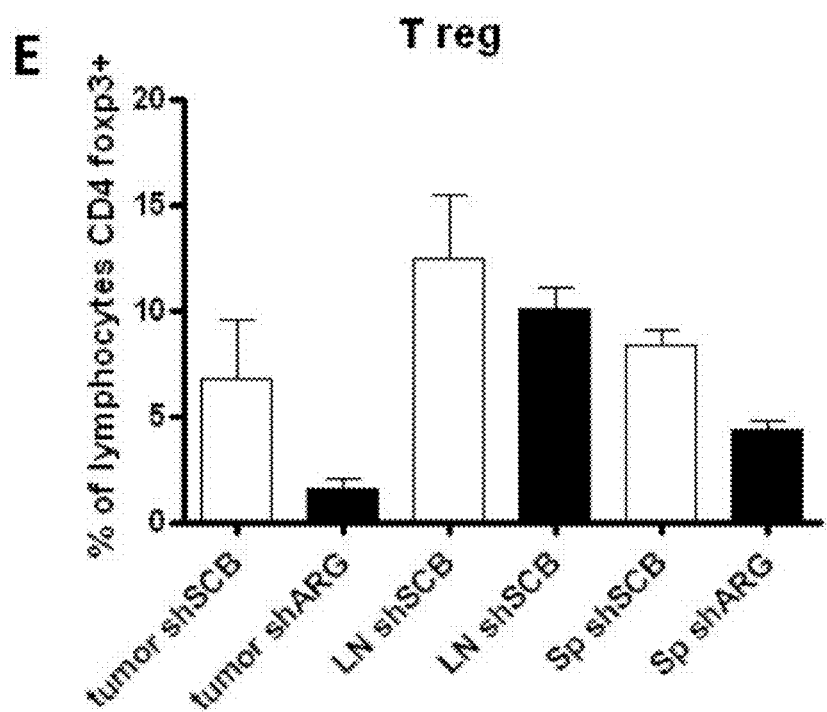
Figure 37D-E

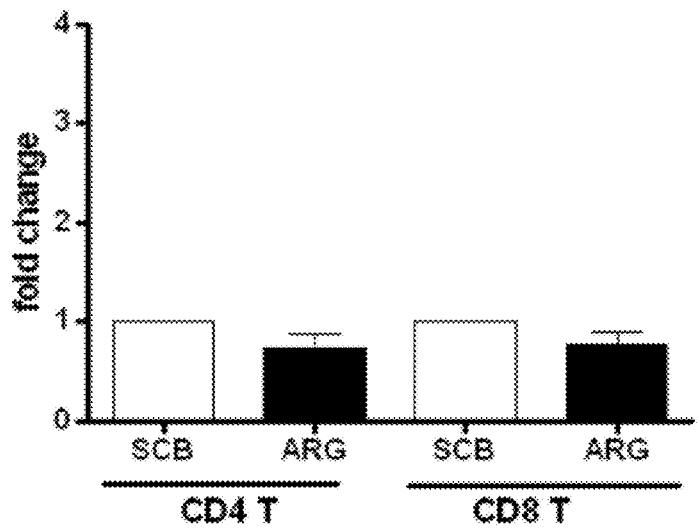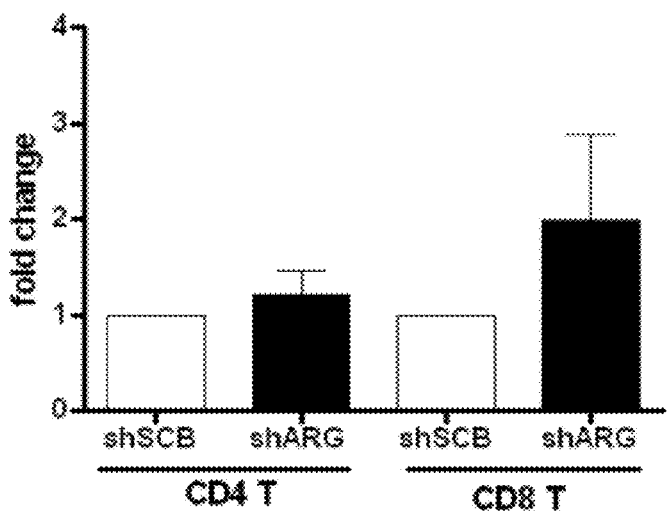
Figure 38A-B

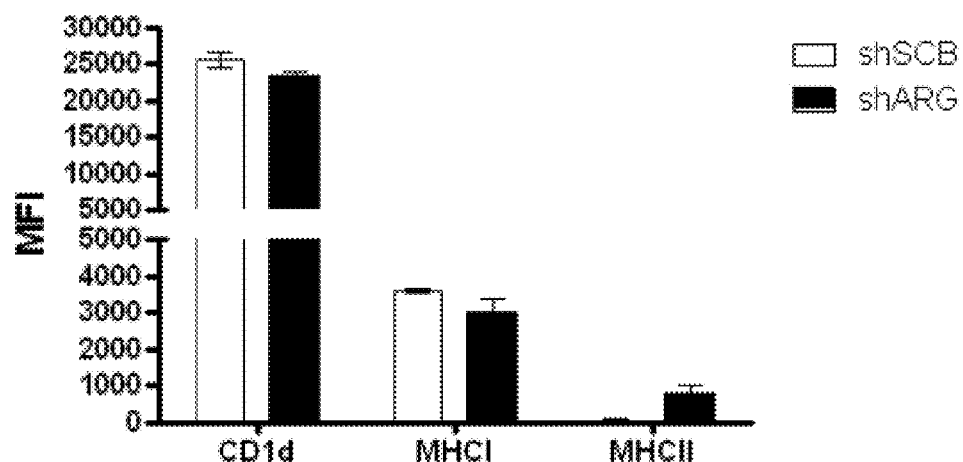
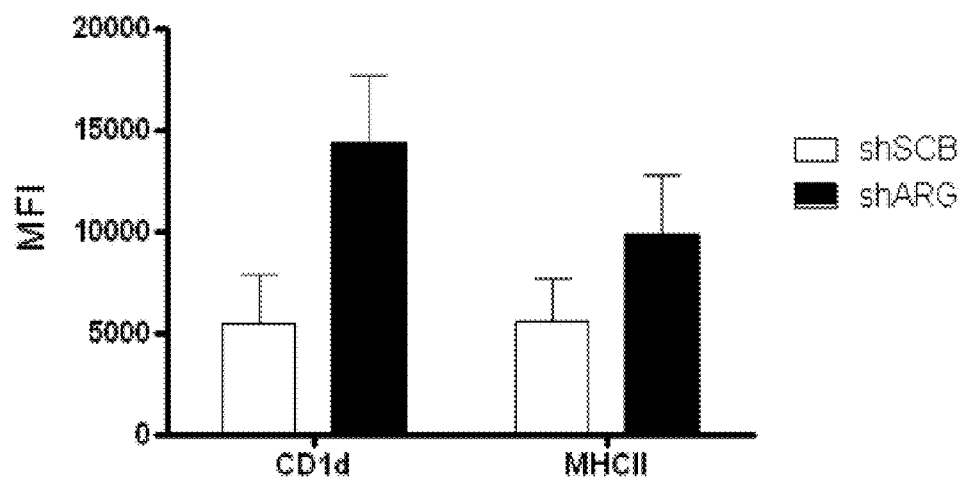
Figure 39A-B

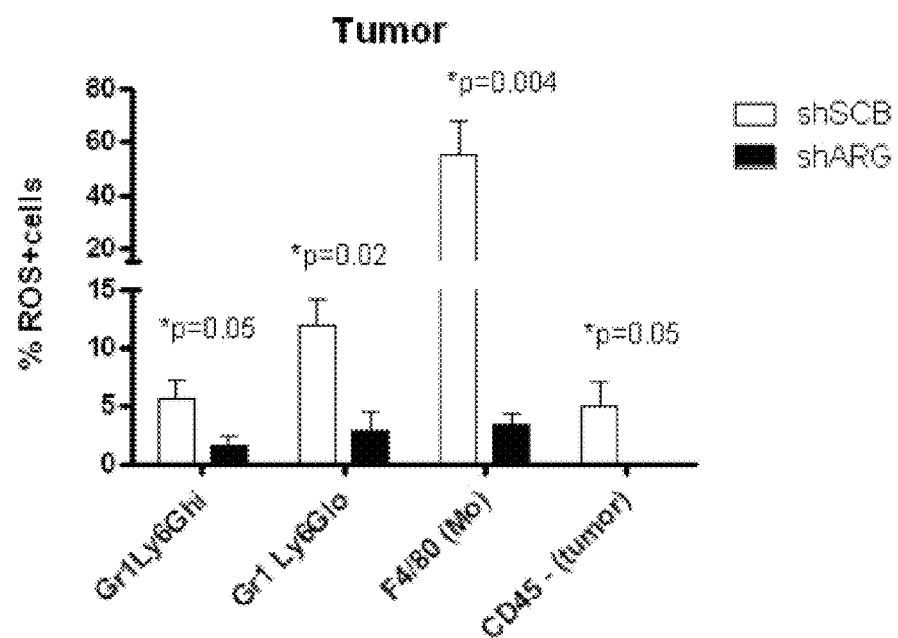
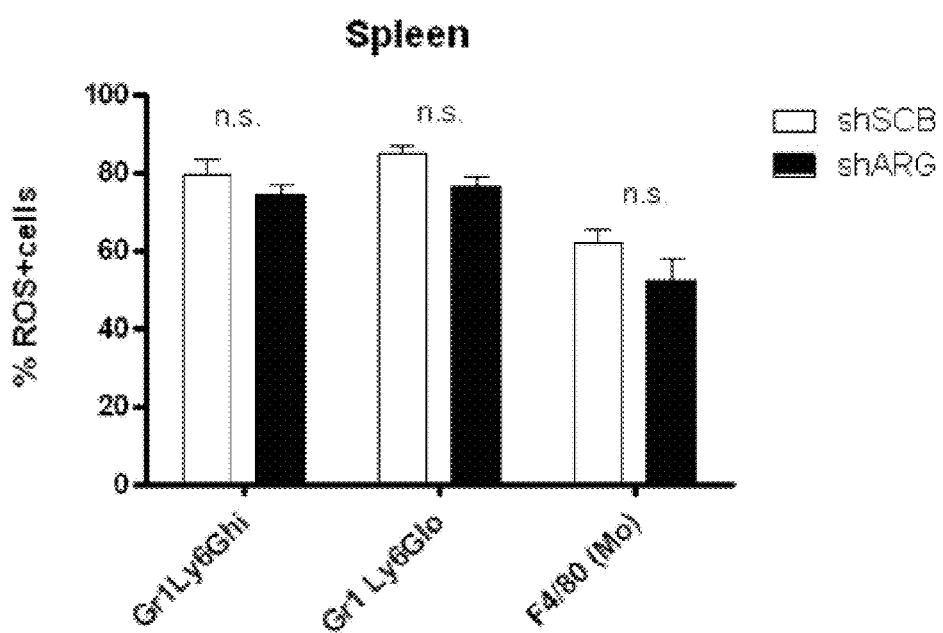
Figure 40B-C

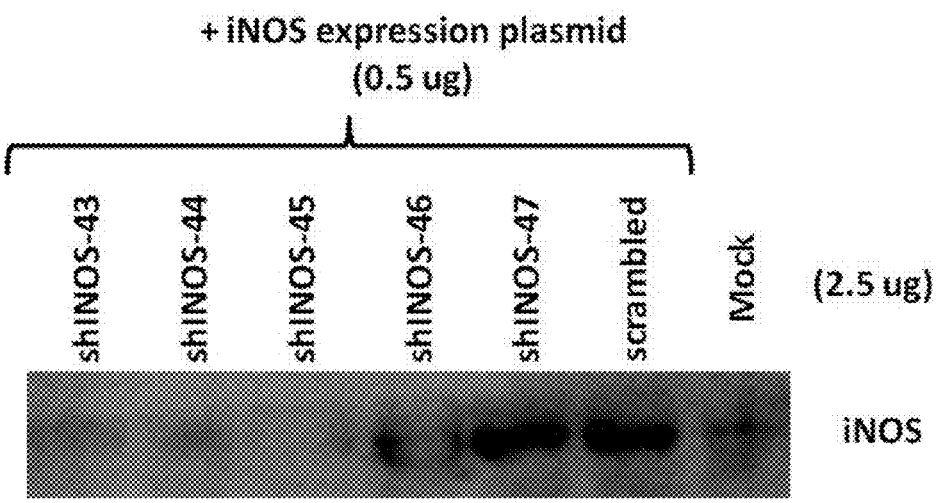
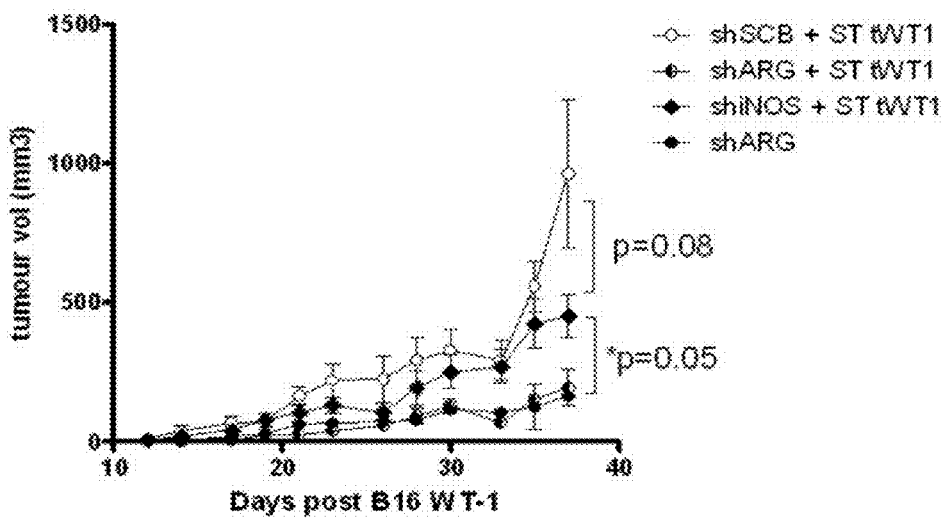
Figure 41A-B

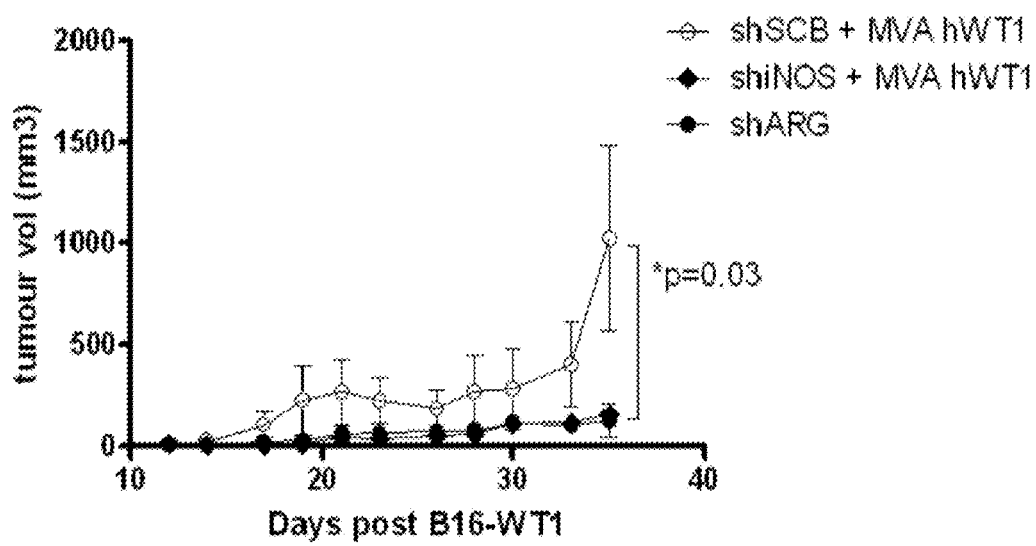
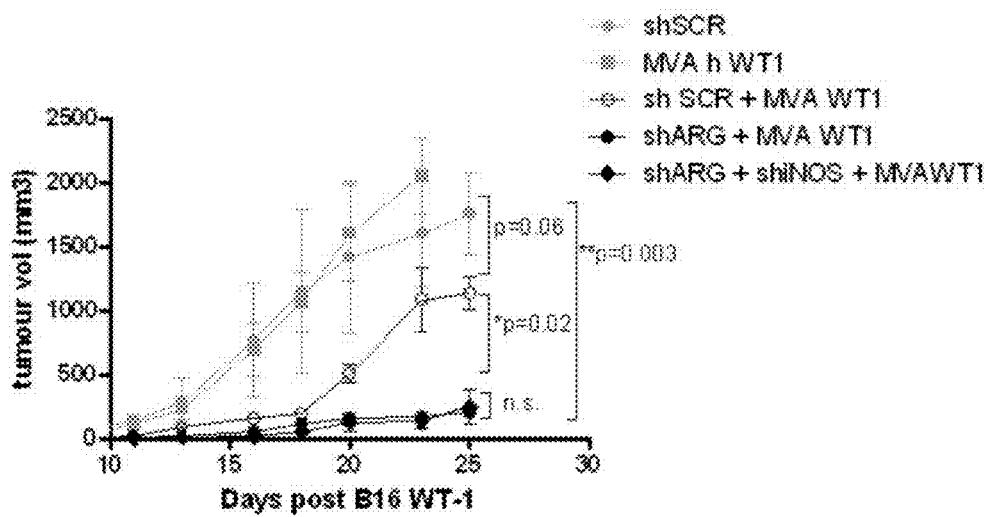
Figure 41C-D

TUMOR ASSOCIATED VACCINES AND COMPOSITIONS FOR DISRUPTING TUMOR-DERIVED IMMUNOSUPPRESSION FOR USE IN COMBINATION CANCER IMMUNOTHERAPY

CROSS REFERENCE TO RELATED APPLICATIONS

This application is a continuation of International Patent Application No. PCT/US12/35512, filed Apr. 27, 2012 and now pending, which claims the benefit of U.S. Provisional Application No. 61/480,316, filed Apr. 28, 2011, and U.S. Provisional Application No. 61/615,167, filed Mar. 23, 2012, all of which are hereby incorporated by reference as if fully set forth herein.

STATEMENT OF GOVERNMENT INTEREST

This invention was made with government support under P01-CA030206 awarded by the National Cancer Institute (NCI). The government has certain rights in the invention.

BACKGROUND

Antigens expressed by tumor cells are an increasingly popular target for the development of immunotherapeutics in the treatment of cancer. Vaccines against such antigens have been developed in hopes of directing an immune response against tumors causing attenuation and regression of tumor growth. However, tumor and cancer vaccines have had limited success due to, among other things, immunosuppressive mechanisms associated with the tumor itself and its associated microenvironment. These mechanisms include the secretion of TGF-β or IL-10 leading to Th2 polarization (Frumento et al. 2002; De Vita et al. 2000; Berghella et al. 1997). Even when favorable vaccination conditions promote robust tumor-specific immunity, increases in intratumoral regulatory T cells (Tregs) and myeloid-derived suppressor cells (MDSCs) within the tumor microenvironment attenuate the anti-tumor immune response (Norian et al. 2009; Polak et al. 2009; Gajewski et al. 2006; Whiteside 2008). Therefore, recruitment of large numbers of tumor-recognizing T cells by a cancer vaccine is not, on its own, sufficient to mediate tumor regression unless the tumor microenvironment is inhibited from dampening T cell function.

Tregs and other immune cells present within the tumor microenvironment are thought to protect tumors from potentially effective immune responses through several immunomodulatory mechanisms (Rodriguez et al. 2003). These mechanisms contribute to tumor-derived immune suppression. For example, activated Tregs may stimulate myeloid-derived suppressor cells to produce indoleamine 2,3-dioxygenase 1 and 2 (IDO1 and IDO2), Arginase 1 and inducible nitric oxide synthase (iNOS), each of which play a role in suppressing effector T cell function, stimulating T cell apoptosis and activating Treg cells to provoke further suppressor functions (see FIGS. 1-3). (Sakaguchi et al. 2009, Hwu et al. 2000; Uyttenhove et al. 2003) In addition, signal transducer of transcription 3 (STAT3) has been recognized as an oncogenic transcription factor in myeloid or tumor cells that, when activated, inhibits production of immunostimulatory molecules and promotes expression of immunosuppressive molecules (see FIG. 4) (Kortylewski & Pardoll 2005; Yu et al. 2007; Wang et al. 2004).

Because the immunosuppressive mechanisms associated with the tumor and the tumor microenvironment allow the tumor to evade an immune response generated by a cancer or tumor vaccine, there is a need for cancer treatments that interfere with these mechanisms to increase the efficacy of such vaccines.

SUMMARY

In one embodiment, a combination cancer immunotherapy regimen is provided. The combination cancer immunotherapy regimen comprises a first *Salmonella* strain comprising a plasmid that expresses survivin (SVN) and a second *Salmonella* strain comprising a plasmid that expresses an shRNA that suppresses the expression of an immunosuppressive target. In some aspects, the first and second *Salmonella* strains are attenuated *Salmonella typhimurium* strains.

In another embodiment, a single modality cancer immunotherapy regimen that includes a therapeutic composition is provided. Such a therapeutic composition may include a *Salmonella* strain comprising a plasmid that expresses an shRNA molecule that suppresses the expression of an immunosuppressive target and suppresses tumor growth. In some aspects, the *Salmonella* strain is an attenuated *Salmonella typhimurium* strain. In other aspects, the immunosuppressive target is STAT3, IDO1, IDO2, Arginase 1, iNOS, CTLA-4, TGF-β, IL-10, pGE2 or VEGF. In one embodiment, the immunosuppressive target is IDO1 or Arg1 and the shRNA molecule is any one of SEQ ID NO:5-14.

In another embodiment, a method of treating cancer is provided. Such a method comprises administering a therapeutically effective amount of a tumor antigen vaccine in combination with a therapeutically effective amount of a composition that disrupts tumor-derived immune suppression. In some aspects, the tumor antigen vaccine comprises a first attenuated *Salmonella typhimurium* strain comprising a plasmid that expresses survivin and the composition that disrupts tumor-derived immune suppression comprises a second attenuated *Salmonella typhimurium* strain comprising a plasmid that expresses shRNA that suppresses the expression of an immunosuppressive target. In some aspects, the first *Salmonella* strain is administered orally, and the second *Salmonella* strain is administered intravenously.

In another embodiment, the method for treating cancer may include administering a therapeutically effective amount of a therapeutic composition, the composition comprising an anti-immunosuppressant vector that disrupts tumor-derived immune suppression and suppresses tumor growth. In some embodiments, the anti-immunosuppressant vector comprises an attenuated *Salmonella typhimurium* strain comprising a plasmid that expresses an shRNA molecule that suppresses the expression of an immunosuppressive target. In some aspects, the immunosuppressive target is STAT3, IDO1, IDO2, Arginase 1, iNOS, CTLA-4, TGF-β, IL-10, pGE2 or VEGF. In one embodiment, the immunosuppressive target is IDO1 or Arg1 and the shRNA molecule is any one of SEQ ID NO:5-14.

In another embodiment, a method of suppressing tumor growth is provided. Such a method may include the steps of (a) intravenously administering to the subject a second *Salmonella* strain comprising a plasmid that expresses an shRNA that suppresses the expression of STAT3, IDO1, IDO2, Arginase 1, iNOS, or TGF-β and (b) orally administering to a subject a therapeutically effective amount of a first *Salmonella* strain comprising a plasmid that expresses a survivin (SVN) protein. In some aspects, the first and second *Salmonella* strains are attenuated *Salmonella typh-* imurium strains. In some embodiments, the first *Salmonella* strain is an MVP728 (purD-/htrA-) strain and the second *Salmonella* strain is a YS1646 (ATCC #202165, also known as VNP20009), RE88, LH430, SL7207, x8429, x8431 or x8468 strain. Further, the SVN may be a *Salmonella* codon optimized survivin (CO-SVN). In one aspect, the immunosuppressive target is STAT3, IDO1, IDO2, Arginase 1, iNOS, or TGF-β and the shRNA is any one of SEQ ID NO:1-19.

In another embodiment, the method of suppressing tumor growth comprises intravenously administering to a subject a single *Salmonella* strain comprising a plasmid that expresses an shRNA molecule that suppresses the expression of an immunosuppressive target and suppresses tumor growth. In some aspects, the *Salmonella* strain is an attenuated *Salmonella typhimurium* strain. In some embodiment, the shRNA molecule suppresses the expression of STAT3, IDO1, IDO2, Arginase 1, iNOS or TGF-β. In one embodiment, the immunosuppressive target is IDO1 or Arg1 and the shRNA molecule is any one of SEQ ID NO:5-19.

BRIEF DESCRIPTION OF THE DRAWINGS

FIG. 6 illustrates the construction and validation of SVN expression vectors. (A) shows bacterial lysates of MVP728-3342 and -2810 cultured overnight in inducing conditions (low phosphate, -P) or non-inducing conditions (high phosphate, +P) were analyzed by western blot for HA tagged survivin (SVN) or LisA. (B) shows the expression vectors 2810, 3342, and 3342Max were constructed to encode HA-tagged LisA, SVN, or SVN codon-optimized for *Salmonella* (CO-SVN), respectively, using the low copy plasmid backbone pWSK29. Each of these proteins was fused to the SPI-2 protein sseF and its expression is dependent on the SPI-2 promoter sseA. SscB encodes for a chaperone protein involved in transporting sseF and any fused proteins. Each construct was then electroporated into MVP728, an attenuated *Salmonella typhimurium* strain known to support expression of sseF-fused proteins from the sseA promoter (23). (C), SVN expression from MVP728 harboring 3342 and 3342Max (Max) constructs was detected by Western blotting of bacterial lysates cultured in inducing conditions (low phosphate media, PCN -P) or non-inducing conditions (high phosphate media, PCN +P). Fusion protein was detected using anti-SVN antibody. (D), detection of SVN and codon-optimized SVN expression from recombinant MVP728. The mouse macrophage cell line RAW264.7 was infected with MVP728 alone, MVP728-3342, or -3342Max for 1 h and then fixed and permeabilized with 1:1 acetone:methanol after 16 h. Cell monolayers were then stained with the conjugated antibodies LPS-FITC, HA-PE, and the nuclear stain DAPI. Cells were imaged under 100× oil immersion using an Axiovert 200. Scale bars, 5 μm.

FIG. 18 is the nucleotide (SEQ ID NO:29) and amino acid (SEQ ID NO:30) sequences for codon-optimized SVN (CO-SVN). Capital letters indicate $Salmonella$ optimized codon.

FIG. 19 is the nucleotide (SEQ ID NO:31) and amino acid (SEQ ID NO:32) sequences for minimally codon-optimized SVN. Capital letters indicate $Salmonella$ optimized codon.

FIG. 20 is the nucleotide (SEQ ID NO:33) and amino acid (SEQ ID NO:34) sequences for the non-codon optimized eukaryotic SVN.

FIG. 21 shows shRNA sequences that were tested for in vitro silencing of IDO in a co-transfection experiment. ShRNA sequences were cloned into the pLKO.1 vector (Sigma), which uses the U6 promoter for transcription. Each complete sequence contains a sense sequence homologous to murine IDO (blue), a loop sequence (black) and a complementary antisense sequence (red).

FIG. 23 illustrates that shIDO-ST treatment silences tumor IDO and controls tumor growth independent of host IDO and adaptive immunity. (a) shows representative DNA sequences encoding for shRNA against IDO and non-specific scrambled target. Sense (blue) and anti-sense (red) 21mer sequences are separated by the loop sequence CTC-GAG (black). (b) shows that cultured B16F10 cells are efficiently infected by shIDO-ST (MOI=50). ShIDO-ST is labeled with a FITC LPS-specific antibody (green, arrows) and the B16F10 cell nuclei are stained with DAPI (blue). Magnification is at 100×. Scale bar, 5 µm. (c) shows that shIDO-ST silences tumor-derived IDO. IDO-KO mice bearing s.c. B16F10 tumors (n=4) were treated with shScr-ST or shIDO-ST. Tumors were processed 1 d after treatment to produce cDNA for detection of IDO by qPCR. Error bars indicate standard error of the mean (SEM). (d) and (e) show that shIDO-ST treatment is effective in controlling B16F10 tumor growth in C57BL/6 (d) and IDO-KO (e) mice. B16F10 tumor-bearing mice (n=4) were treated with shScr-ST, shIDO-ST, pEQshIDO-ST, D-1MT or D-1MT+cyclophosphamide (CY). Tumor volumes were measured longitudinally. Error bars indicate SEM. ***P<0.001 by one-way ANOVA test. (f) and (g) show that shIDO-ST treatment is effective in controlling B16F10 tumor growth in mice depleted of individual immune subsets. B16F10 tumor-bearing B6 mice in (f) or IDO-KO mice in (g) (n=4) were treated with shIDO-ST. Antibody depletion of CD8+, CD4+, and NK immune subsets began 2 d after the first shIDO-ST inoculation, with maintenance depletions every 3 d. (h) shows that shIDO-ST treatment controls B16F10 tumor growth in RAG1-KO mice. B16F10 tumor-bearing RAG1-KO mice (n=4) were treated with shScr-ST or shIDO-ST. *P<0.05 by Student's t test

FIG. 27 illustrates that treatment with shIDO-ST increases tumor influx of polymorphonuclear neutrophils (PMN) and induces total intratumoral cell death. C57BL/6 mice bearing B16F10 tumors (≥7-8 mm diameter) were treated with PBS, shScr-ST, or shIDO-ST. Tumors were excised 1 week after treatment and processed. (a) shows intratumoral influx of $Gr1^+CD11b^+$ cells as a percentage of T, B, MDSC, and macrophage subsets from total $CD45^+$ cells using flow cytometry. *P<0.001 by one-way ANOVA test. (b) shows that the increased frequency of $Gr1^+CD11b^+$ cells is primarily due to $Ly6G^+$ PMN. Shown is the percentage of Ly6G+CD11b+ PMN gated from $Gr1^+$ $CD11b^+$ cells. (c) and (d) shows that intratumoral $CD45^-$ and $CD45^+$ cells from shIDO-ST-treated groups are significantly more apoptotic than the shScr-ST-treated group by Annexin V staining of $CD45^-$ and $CD45^+$ in single-cell suspensions of tumor from mice (n=4) receiving PBS, shScr-ST, or shIDO-ST treatment. Representative histograms (left panels in c, d) are shown. *P<0.001 by one-way ANOVA test.

FIG. 35 shows anti-tumor effects of shArg1 therapy is mediated by T cells and myeloid derived suppressor cells (MDSC). (A) In vivo depletion of distinct subsets of leukocytes was assessed by repeated administration of anti-CD4, anti-CD8, anti-Gr1, anti-Asilo-GM (anti-NK) monoclonal antibodies or PBS (i.p.) every 3-4 days to mice bearing B16F10 tumors (s.c.). The frequency of these subsets in the peripheral blood of these animals was measured by flow cytometry. (B) Mice (n=3) bearing B16 tumors were treated with shArg1 on day 10 and anti-CD8, anti-CD4, anti-NK antibody or PBS on days 11, 14, 17 and 21 (shArg1 shown as shArg in Figure). Tumor volume was assessed over time. (C) Tumor bearing mice were treated with shArg1 or shScramble (shSCB) on day 14 and depleted of MDSC with anti-GR1 antibody on days 15 and 18 (shArg1 shown as shARG in Figure). Tumor growth was measured over time. (D) Kaplan-Meier survival curves of the mice in (C) (shArg1 shown as shARG in Figure).

FIG. 38 shows silencing of Arginase-1 enhances the expression of CD3 ζ chain on CD8 T cells within the tumor microenvironment but has no effect on splenic T cells. (A) Splenocytes and tumors (B) from mice challenged with B16 (day 0) and treated with shArg1 or shSCB (day 12) were isolated day 19. The level of CD3 ζ chain expression on CD4$^+$ T and CD8$^+$ T cells was assessed by flow cytometry. Data presented as fold change in relation to mean value of shSCB group (shArg1 shown as shARG or ARG; shSCB also shown as SCB in Figure).

FIG. 39 shows silencing of Arginase-1 leads to the upregulation of MHC-II and CD1d complexes on dendritic cells. Dendritic cells (CD11c$^+$) from the spleen (A) or tumor (B) of mice treated as in FIG. 38 were stained with antibodies against MHC-I, -II and CD1d. Data presented as the mean fluorescence intensity (MFI). shArg1 shown as shARG in Figure.

FIG. 41 shows in vivo treatment with shiNOS slows down tumor progression. (A) ShRNA-expressing plasmids designed to silence iNOS (Sigma, shiNOS; 43 through 47) were co-transfected into COS-1 cells with an iNOS-expressing plasmid at a ratio of 5:1 shRNA:iNOS. Equal amounts of total lysate were loaded for western blot analysis of iNOS expression was detected using an iNOS-specific antibody (Cell Signaling Technology, Beverly, Mass.). ShiNOS-45 showed significant silencing of iNOS and was selected for transformation into YS1646 to generate YS1646-shiNOS. (B) Mice were challenged with melanoma B16F10 tumor cells transduced with WT-1 antigen ($1\times10^5$, s.c.) and treated with an initial intravenous injection of shSCB/ARG/iNOS ($5\times10^6$ cfu) on day 2, immunized with ST-tWT (A) or MVP728-WT-1 (C) vaccines on day 5 (oral gavage; $1\times10^7$ cfu) and boosted subsequently with shArg1/iNOS on days 11 and 18. Tumor volume was monitored over time. (D) Mice were challenged with B16F10-WT1 as above and treated with shArg1/shiNOS/SCB on day 2 followed by MVP728-WT-1 vaccination on day 6. Tumor volume was monitored over time. Statistical significance based on Student t-test analysis where p<0.05.

DETAILED DESCRIPTION

Figure 1:
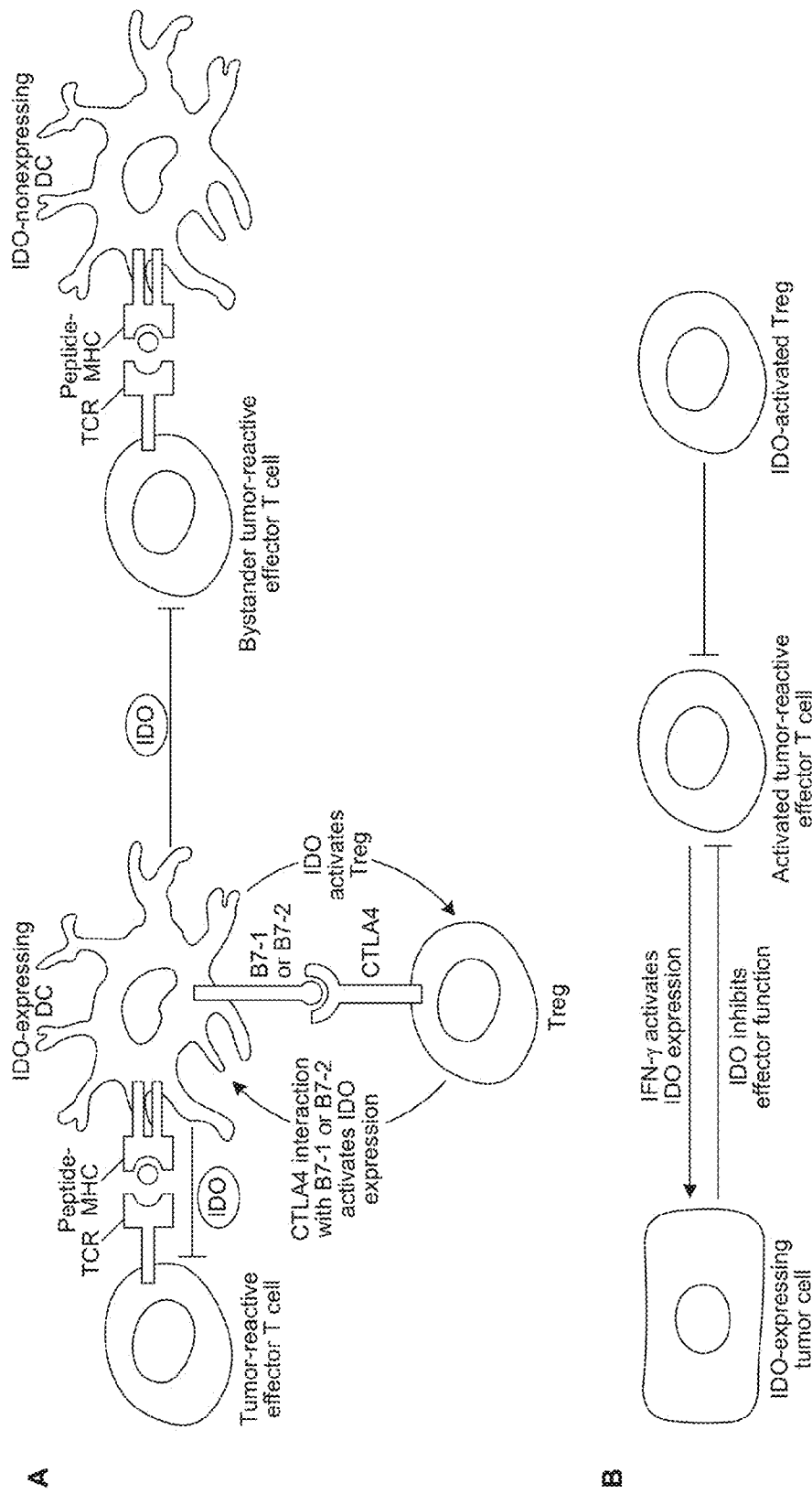
FIG. 1 is a schematic diagram showing the effects of IDO1 in the tumor microenvironment. (A) IDO1-expressing dendritic cells (DCs) directly suppress and anergize tumor-reactive effector T cells responding to antigens presented by IDO1+DCs. Additionally, IDO1 can inhibit T cell responses to antigens presented by neighboring antigen presenting cells (APCs) through bystander suppression. One mechanism that can induce IDO1 expression in DCs is reverse signaling mediated by B7-1 or B7-2 molecules expressed on DCs binding to CTLA4 expressed on Tregs. IDO1 expression by DCs can also activate Tregs and drive the differentiation of new Tregs from naïve T cells. (B) Tumor cells can either express IDO1 constitutively or upregulate IDO1 in response to inflammatory signals generated by activated effector T cells. IDO1 expression by tumor cells inhibits effector T cells and also activates Tregs to further contribute to the suppressive microenvironment within the tumor. The figure is from Munn D. H. and Mellor A L, Indoleamine 2,3-dioxygenase and tumor-induced tolerance. J Clin Invest 117:1147-1154 (2007), which is hereby incorporated by reference as if fully set forth herein.
Figure 2:
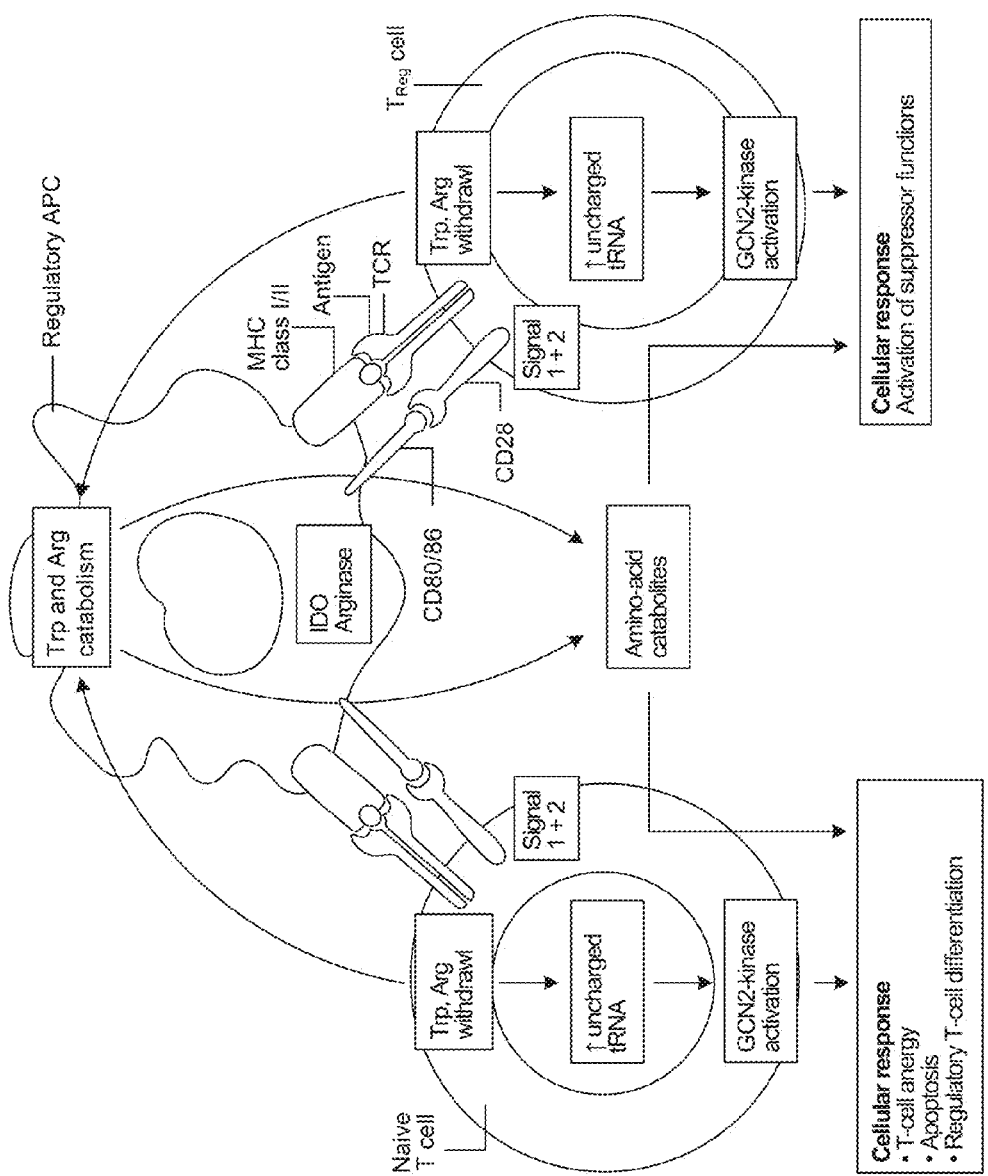
FIG. 2 is a schematic diagram showing the effects of Arginase 1 in the tumor microenvironment. The figure is from Mellor A. L. & Munn D. H. Creating immune privilege: active local suppression that benefits friends, but protects foes. Nature Reviews Immunology 8, 74-80 (2008), which is hereby incorporated by reference as if fully set forth herein.
Figure 3:
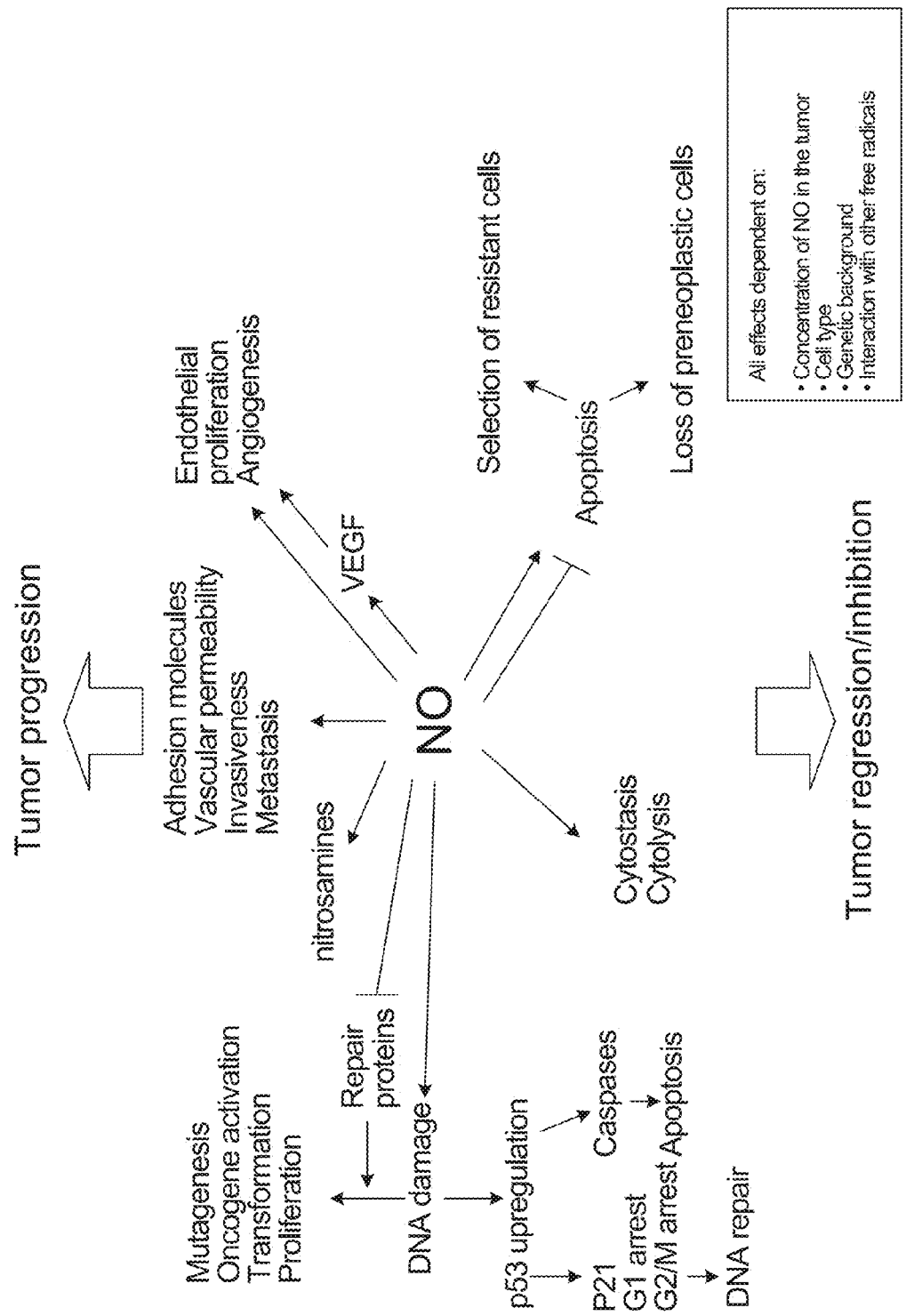
FIG. 3 is a schematic diagram showing the effects of iNOS in the tumor microenvironment. The figure is from Lechner et al. Inducible nitric oxide synthase (iNOS) in tumor biology: The two sides of the same coin. Semin Cancer Biol. 15(4):277-89 (2005), which is hereby incorporated by reference as if fully set forth herein.
Figure 4:
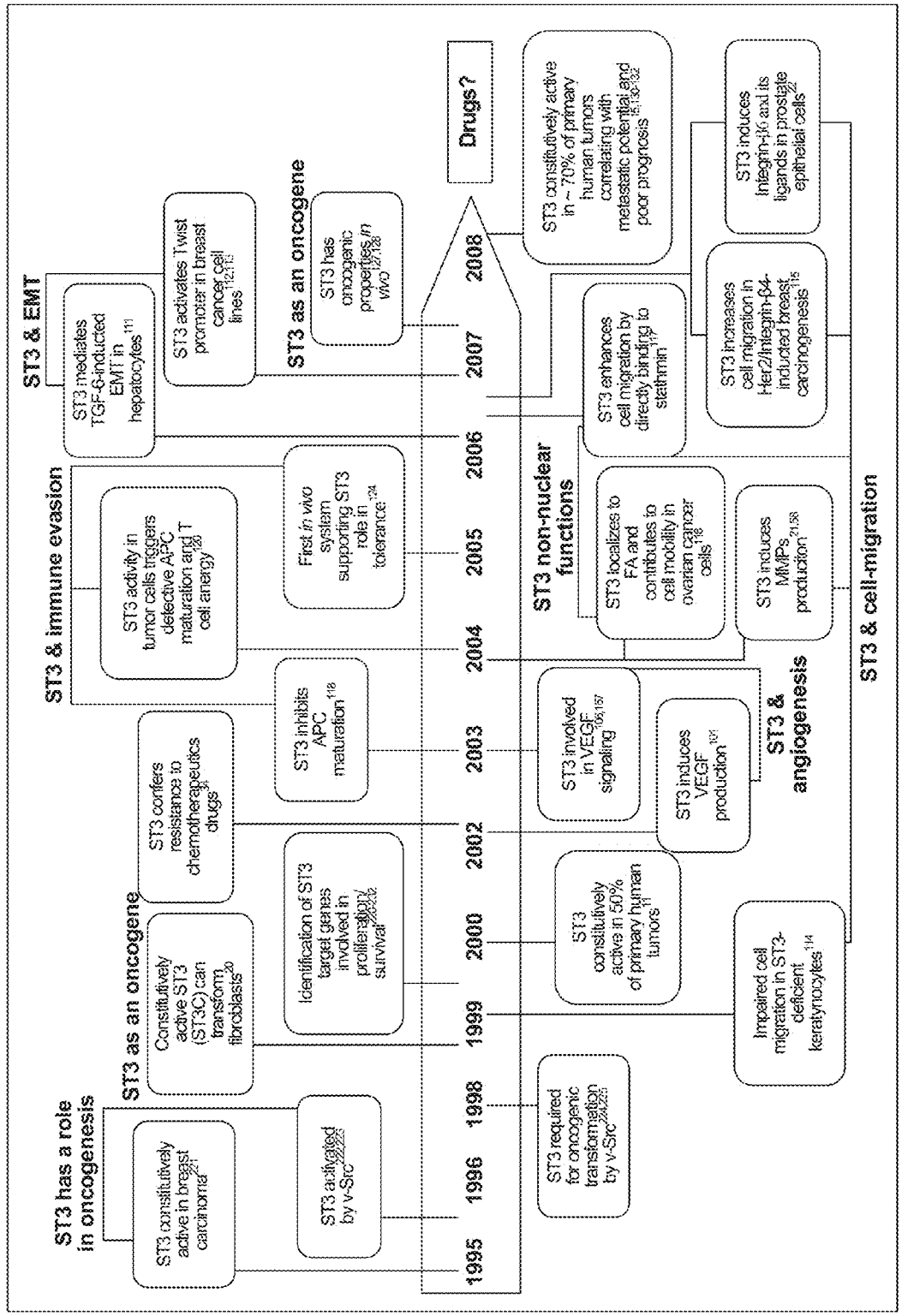
FIG. 4 is a schematic diagram showing the role of STAT3 in cancer. The figure is from Pensa, S. et al., STAT1 and STAT3 in Tumorigenesis: Two Sides of the Same Coin? in JAK-STAT PATHWAY IN DISEASE (Anastasis Stephanou, ed., Landes Bioscience 2009), which is hereby incorporated by reference as if fully set forth herein.

Therapeutic compositions used in a cancer immunotherapy regimen, methods for their use in the treatment of cancer and attenuation of tumor growth are provided herein.

According to the embodiments described herein, a cancer immunotherapy regimen may include one or more therapeutic compositions such as an anti-immunosuppressive vector or agent, a tumor antigen vaccination or a combination thereof. Such therapeutic compositions may target a gene or protein in a tumor or tumor microenvironment that, when acted on by the therapeutic composition, activates an immunomodulatory process. An immunomodulatory process is a cellular or biological process in a cell or tissue that leads to an increased or decreased immune response. Thus, the therapeutic compositions described herein act as immunostimulants, which increase an immune response, or immunosuppressants, which decrease or suppress an immune response. Further, the therapeutic compositions may have different immunomodulatory effects in different cells or tissues. For example, a particular therapeutic composition may act as an immunostimulant in a normal cell, but may act as an immunosuppressant in a tumor cell.

Tumor Antigen Vaccines

In one embodiment, a therapeutic composition may include a vaccine against an immunogenic tumor antigen or a tumor-associated-antigen (TAA) (a "tumor antigen vaccine"). TAAs are immunogenic substances or antigenic portions thereof that are expressed by tumor cells and can be recognized by the effector T cells and B cells of the immune system. Tumor antigen vaccines that are engineered to express a TAA in a host elicit an immune response against a tumor, resulting in attenuation of tumor growth or regression of the tumor. Any suitable TAA may be expressed by tumor antigen vaccines including, but not limited to, alphafetoprotein (AFP), carcinoembryonic antigen (CEA), Wilms' tumor-1 antigen (WT-1), MUC-1, epithelial tumor antigen (ETA), tyrosinase, melanoma-associated antigen (MAGE), abnormal products of ras and p53 genes and survivin (SVN).

In one embodiment, the tumor antigen vaccine is an SVN vaccine. Survivin (SVN) is a member of the inhibitor of apoptosis protein (IAP) family whose function is involved in prolonging cell survival and cell cycle control (Altieri & Marchisio 1999; Zhou et al. 2006). SVN is an important tumor-associated antigen (TAA) for therapeutic vaccination because it is overexpressed by most, if not all, solid tumors and is poorly expressed in normal adult tissues (Altieri 2003). Increased expression of SVN is also observed in endothelial cells during angiogenesis, thereby serving as an additional target for therapy (Tran et al 1999). In animal tumor models, downregulation or inactivation of SVN has been shown to inhibit tumor growth (Yin et al. 2008; Zhang et al. 2009; Ryan et al. 2009). Therefore, strategies to improve SVN-specific responses, such as using adjuvants or immunogenic vectors, are important to the success of therapeutic vaccination (Xiang et al. 2005; Xiang et al. 2005).

The SVN vaccine may include an expression vector having an expression cassette that encodes an SVN gene. In one aspect, the SVN gene may be a codon-optimized SVN (CO-SVN) (FIG. 18; SEQ ID NO:29) to increase the efficiency of SVN expression in a particular delivery vehicle. The expression vector may be a plasmid, a viral vector (e.g., adenoviral vectors, adeno-associated viral vectors, lentiviral vectors or retroviral vectors) or any other suitable vector that is able to express a recombinant protein or nucleic acid. In one embodiment, the expression vector is a plasmid that is inserted into a delivery vehicle, such as a bacterial cell or a eukaryotic cell. In one embodiment, the bacteria carrier may be any suitable bacteria strain that may be transformed with a plasmid, resulting in the expression or production of the recombinant gene or protein (e.g. SVN) contained therein.

The delivery vehicle that carries the SVN plasmid according to the embodiments and Examples described herein is an attenuated Salmonella strain, for example, any serovar of Salmonella enterica, including, but not limited to, Salmonella typhimurium, Salmonella enteritidis or Salmonella typhi.

Figure 33:
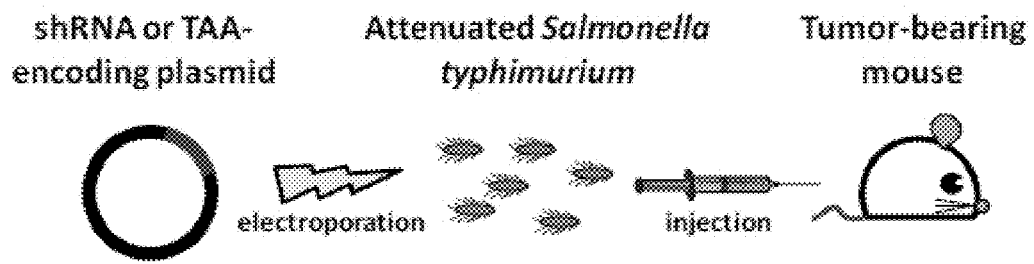
FIG. 33 shows construction and administration of recombinant Salmonella. Plasmids encoding shRNA sequences or tumor associated antigens (TAAs) are electroporated into attenuated Salmonella typhimurium (ST). TAA-encoding ST vaccines are administered twice to tumor-bearing mice by oral gavage, whereas those carrying shRNA plasmids are injected via intravenous route. Mice are monitored for changes in tumor burden, general health, and weight during treatment.

Advances in the generation of attenuated enteric bacterial vectors, such as Salmonella typhimurium, facilitates the highly translational tumor-specific delivery of antigens or plasmids (Chen et al. 2009; King et al. 2009; Xu et al. 2009). The vector itself acts as an adjuvant to elicit innate immunity and aid in generation of adaptive immunity against recombinant antigen. The most common Salmonella vaccines employ Salmonella pathogenicity 1 (SPI1) type 3 secretion systems (T3SS), which only produce recombinant antigen in a defined timeframe as the pathogen penetrates the host cell (Haraga et al. 2008). More advanced vaccine designs utilize SPI2 T3SS, which switches on recombinant antigen production when the Salmonella have entered the host cell, allowing for extended antigen production (Xiong et al. 2009). This type of Salmonella typhimurium (ST) T3SS platform may be used to deliver greater quantities of antigen directly to the tumor microenvironment (FIG. 33).

Numerous studies have documented strains that colonize hypoxic regions of solid tumors weeks following intravenous injection, with no detectable bacteria in peripheral organs, making it an effective delivery vehicle for targeting shRNA therapeutics into solid tumors (Theys et al. 2003; Rosenberg et al. 2002; Luo et al. 2001).

As described in the Examples below, a potent Salmonella-based vaccine was developed to express codon-optimized survivin (CO-SVN) (FIG. 18; SEQ ID NO:29). Therefore, in one embodiment, a tumor antigen vaccine that is part of the combination cancer immunotherapies, referred to herein as 3342Max, includes an attenuated Salmonella typhimurium strain that is transformed with a plasmid that expresses SVN. In one aspect the SVN is codon-optimized (CO-SVN) for Salmonella expression and the attenuated Salmonella typhimurium strain may be an MVP728 (purD-/htr-) strain. When used alone as a therapeutic vaccine, 3342Max has the ability to attenuate growth of aggressive murine tumors that overexpress SVN. However, the vaccine becomes ineffective against larger tumors that are associated with increased immunosuppressive conditions.

Anti-Immunosuppressant Vectors and Agents

In one embodiment, a therapeutic composition may include an expression vector that disrupts tumor-derived immune suppression (an "anti-immunosuppressant vector"). Such an expression vector may express an agent that inhibits, suppresses or blocks an immunosuppressive target gene or protein in the tumor microenvironment (an "anti-immunosuppressant agent"). In one embodiment, the expression vector includes an expression cassette that encodes the agent. The expression vector may be a plasmid, a viral vector (e.g., adenoviral vectors, adeno-associated viral vectors, lentiviral vectors or retroviral vectors) or any other suitable vector that is able to express the agent. As described further below, the anti-immunosuppressant vectors and agents described herein may be used alone as a single modality cancer immunotherapy regimen or with other therapeutic compositions in a combination cancer immunotherapy regimen.

In one embodiment, the expression vector is a plasmid that is inserted into a delivery vehicle, such as a bacterial carrier cell or a eukaryotic carrier cell. In one embodiment, the bacteria carrier cell may be any suitable bacteria strain that may be transformed with a plasmid, resulting in the expression or production of the agent contained therein. The delivery vehicle that carries the agent plasmid according to the embodiments and Examples described herein is an attenuated *Salmonella* strain, for example, any serovar or *Salmonella enterica*, including, but not limited to, *Salmonella typhimurium*, *Salmonella enteritidis* or *Salmonella typhi*. As described above, attenuated *Salmonella* strains are an effective delivery vehicle for targeting shRNA therapeutics into solid tumors. In some embodiments, the delivery vehicle is an attenuated *Salmonella typhimurium* strain, for example YS1646, RE88, LH430, SL7207, x8429, x8431 or x8468. In one embodiment, the attenuated *Salmonella typhimurium* strain may be a YS1646 *Salmonella typhimurium* strain (ATCC Accession No. 202165, also referred to herein as VNP20009).

The immunosuppressive target gene or protein may be any gene or protein associated with a tumor microenvironment that, upon inhibition, suppression or blockade by the agent, ultimately results in an increased immune response against the tumor and/or associated antigens. Such target genes or proteins may include, but are not limited to, IDO1, IDO2, Arginase 1, iNOS, STAT3, cytotoxic T lymphocyte antigen-4 (CTLA-4), Transforming Growth Factor-β (TGF-β), interleukin 10 (IL-10), prostaglandins (e.g., pGE2) and vascular endothelial growth factor (VEGF).

The agent may be any suitable molecule capable of blocking, inhibiting or suppressing target gene expression or a target protein activity including, but not limited to, antibodies or functional fragments thereof, small molecules, aptamers, nucleic acids and RNA interference molecules (e.g., small interfering RNA (sRNA), microRNA (miRNA) and small hairpin RNA (shRNA)). Suppression, inhibition or blockade of the immunosuppressive target gene or protein ultimately results in disruption of tumor-derived immunosuppression within the tumor microenvironment through direct or indirect mechanisms. In some embodiments, the agent may be an shRNA molecule that targets STAT3, IDO1, IDO2, Arginase 1, iNOS, CTLA-4, IL-10, VEGF, pEGF2, or TGF-β. According to one aspect, the shRNA molecules may be any of the following:

```
shSTAT3 (Origene)
shSTAT3#58:
                                     (SEQ ID NO: 1)
AGTTCCTGGCACCTTGGATTGAGAGTCAA shSTAT3#59:
                                     (SEQ ID NO: 2)
ACTGGATAACTTCATTAGCAGAATCTCAA shSTAT3#60:
                                     (SEQ ID NO: 3)
CATCAATCCTGTGGTATAACATGCTGACC shSTAT3#61:
                                     (SEQ ID NO: 4)
ACCTGAAGACCAAGTTCATCTGTGTGACA shIDO1 (Sigma: Mission)
shIDO1-8:
                                     (SEQ ID NO: 5)
CCTCGCAATAGTAGATACT shIDO1-9:
                                     (SEQ ID NO: 6)
CGTCTCTCTATTGGTGGAA shIDO1-10:
                                     (SEQ ID NO: 7)
GCAAAGAATCTCCTGCAGA shIDO1-11:
                                     (SEQ ID NO: 8)
GCCCATGACATACGAGAAC shIDO1-12:
                                     (SEQ ID NO: 9)
CCAGTCCGTGAGTTTGTCA shArg1 (Sigma: Mission)
shArg1-5:
                                    (SEQ ID NO: 10)
GCAGTTCCTTTCTGGTATG shArg1-6:
                                    (SEQ ID NO: 11)
GCCTTTGTTGATGTCCCT shArg1-7:
                                    (SEQ ID NO: 12)
CCAGGGACTGACTACCTTA shArg1-8:
                                    (SEQ ID NO: 13)
GCCAAAGACATCGTGTACA shArg1-9:
                                    (SEQ ID NO: 14)
TCTCTACATCACAGAAGA shiNOS (Sigma: Mission)
shiNOS-43:
                                    (SEQ ID NO: 15)
GTATTGTACTATTGTGGACTA shiNOS-44:
                                    (SEQ ID NO: 16)
CCAGTATTATGGCTCCTTTAA shiNOS-45:
                                    (SEQ ID NO: 17)
GCCACAGCAATATAGGCTCAT shiNOS-46:
                                    (SEQ ID NO: 18)
CCTATCTCCATTCTACTACTA shiNOS-47:
                                    (SEQ ID NO: 19)
GCTGTAACAAAGGAAATAGAA
```

In some embodiments, a *Salmonella typhimurium* (ST) strain may be transformed by a plasmid containing an shRNA (such as those above) that targets STAT3 (e.g., shSTAT3-ST), or IDO1 (e.g., shIDO1-ST), Arginase 1 (shArg1-ST), iNOS (shiNOS-ST), IDO2 (shIDO2-ST), CTLA-4 (shCTLA-4-ST), IL-10 (shIL-10-ST), pGE2 (shpGE2-ST), VEGF (shVEGF-ST) or TGF-β (shTGFβ-ST). Any suitable ST strain may be transformed with such a plasmid, including, but not limited to YS1646, RE88, LH430, SL7207, x8429, x8431, and x8468.

The therapeutic compositions described above may also include one or more pharmaceutically acceptable carrier. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

Cancer Immunotherapy Regimens

Because the tumor microenvironment may help a tumor evade an immune response against it, a cancer vaccine, such as a tumor antigen vaccine, may need an additional agent that is co-administered with said vaccine that acts as an adjuvant to establish or increase its efficacy. For example, previous studies have shown that tumor-associated stromal cells expressing fibroblast activation protein-α (FAP) are a source of immunosuppression in a model of pancreatic ductal adenocarcinoma (Kraman et al. 2010). Administration of a therapeutic vaccine in the absence of FAP expressing stromal cells showed an increase in hypoxia-induced tumor necrosis when compared to FAP+ mice. Similarly, modest additive effects have been shown when vaccination is combined with the drug gemcitabine (Ishizaki et al. 2010), and increased anti-tumor responses have been reported by inhibiting the tolerogenic molecule IDO1 (Zheng et al. 2006). These studies suggest that overcoming tumor-induced immunosuppression is important to achieve successful outcomes using immunotherapy.

Previous mechanism-based studies have revealed changes in cytokine profile, T cell subsets, and signal transduction modifiers that all contributed to the blunting of tumor growth as a result of a reduction or elimination of STAT3 expression (Kortylewski et al. 2005; Kortylewski et al. 2009b; Kortylewski et al. 2008). As a result, preliminary therapeutic strategies using small molecules and RNA interference molecules have been administered by direct tumoral injection. These approaches have shown moderate efficacy, but in every case there is tumor breakthrough within 20-25 days post-administration. An alternative strategy has been the approach of tumor-targeting *Salmonella* delivery of shRNA eukaryotic expression plasmids by intravenous (i.v.) injection. In contrast to the studies described herein, previous studies have found that shSTAT3 alone is sufficient to significantly limit tumor growth, independent of additional modalities such as vaccination (Zhang et al. 2007). However, the growth attenuation was transient in these studies and its success as an independent treatment modality remains in doubt. Moreover, in contrast to previous studies using a CpG DNA chimera with an RNAi sequence that was administered intratumorally (Kortylewski et al. 2009a), the STAT3-specific shRNA sequence used in the studies described herein have sequence identity to a single target. Therefore, the results of the studies described below using STAT3-specific and IDO1-specific shRNA are likely more reliable than those using CpG DNA chimera due to multiple off-target sequences (>100 in the mouse genome) tempering the interpretation of the results (NCBI-BLAST Analysis). Moreover, CpG has been shown to induce IDO, which might counteract the strategy of administering a CpG chimera.

Cancer vaccine therapies by themselves have only achieved limited success. Therefore, according to one embodiment, cancer treatment regimens that include a vaccine against a TAA, such as the aforementioned CO-SVN vaccine, may be combined with a therapeutic composition that disrupts tumor-derived immune suppression according to the embodiments described herein. As described above, the CO-SVN vaccine was rendered ineffective by larger tumor sizes. However, the efficacy of the vaccine may be rescued in tumor-bearing mice are treated with a *Salmonella* strain transformed by a plasmid containing an shRNA that targets STAT3 (e.g., shSTAT3-ST), or IDO1 (e.g., shIDO1-ST), *Salmonella* carrying an shRNA targeting Arginase 1 (shArg1-ST), iNOS (shiNOS-ST), IDO2 (IDO2-ST), CTLA-4 (shCTLA-4-ST), IL-10 (shIL-10-ST), pGE2 (shpGE2-ST), VEGF (shVEGF-ST) or TGF-β (TGFβ-ST) may also be used to rescue the efficacy of the CO-SVN vaccine.

Therefore, according to some embodiments, the therapeutic compositions described herein may be part of a combination or a single modality cancer immunotherapy regimen. A combination cancer immunotherapy regimen may include two or more therapeutic compositions, such as those described above. In one embodiment, the combination cancer immunotherapy regimen includes at least one tumor antigen vaccine and at least one composition that disrupts tumor-derived immune suppression. Additional therapeutic compositions may be included in the combination cancer immunotherapy regimen. Alternatively, the regimen may include expression vectors or other single compositions that disrupt tumor-derived immune suppression. For example, when treating cancer or attenuating tumor growth in a subject, administration of a single *Salmonella* comprising a vector that expresses an shRNA against IDO1, IDO2, STAT3, Arginase 1, iNOS, or TGF-β may be effective alone.

In one embodiment, a tumor antigen vaccine that is part of a combination cancer immunotherapy includes first *Salmonella* strain that includes a plasmid (MVP728 (purD-/htr-)) that expresses survivin (e.g., SVN or CO-SVN), and a composition that disrupts tumor-derived immune suppression that is part of a combination cancer immunotherapy includes a second *Salmonella* strain (e.g., YS1646) that carries a plasmid that expresses an shRNA that suppresses the expression of an immunosuppressive target gene or protein (e.g., STAT3, IDO1, IDO2, Arginase 1, iNOS, TGF-β) in the tumor microenvironment.

The combined strategy of silencing immunosuppressive molecules followed by vaccination may act synergistically to attenuate tumor growth and provides translational direction to improved tumor immunotherapy. STAT3 silencing was associated with increased proliferation and granzyme B levels from intratumoral CD4+ and CD8+ T cells in vaccinated mice. The combined strategy also increased apoptosis in tumors of treated mice and enhanced SVN-specific in vitro killing of tumor targets. Interestingly, mice treated with YS1646-shSTAT3 or 3342Max alone were similarly unsuccessful in rejecting established tumors, while the combined regimen was highly potent.

In another embodiment, the cancer immunotherapy regimen is a single modality cancer immunotherapy regimen, which includes a single *Salmonella* carrying an expression plasmid that encodes for an shRNA molecule to be expressed in the tumor microenvironment. The shRNA molecule may target and suppress the expression of STAT3 (e.g., shSTAT3-ST), IDO1 (e.g., shIDO1-ST), IDO2 (e.g., IDO2-ST), Arginase 1 (e.g., shArg1-ST), iNOS (e.g., shiNOS-ST) or TGF-β (e.g., shTGFβ-ST). In some aspects, the shRNA molecule may be any of SEQ ID NO:1-19. In certain embodiments, the shRNA molecule is shIDO (which targets IDO) or shArg1 (which targets Arginase-1); each of which are discussed in detail below IDO as a Single Modality Cancer Immunotherapy Regimen In one embodiment, an anti-immunosuppressant vector that expresses an shRNA to silence IDO expression may be sufficient to be used alone as a single modality cancer immunotherapy regimen. IDO is an important regulator of T cell function that also has profound effects on control of tumor growth (Katz et al. 2008, Lob et al. 2009; Soliman et al. 2010; Munn & Mellor 2007). An inhibitory role of IDO in tumor immunity follows its property of preventing rejection of an in utero fetus from its non-identical parent (Munn et al. 1998; Mellor et al. 2001). The properties of 1-methyltryptophan (1-MT) as an inhibitor of IDO were discovered by further investigations in this system and later shown to restore antitumor immunity in mouse transplantable tumor models (Mellor & Munn 2004; Munn et al. 2004). One fact that that underlies the feasibility of the approach described herein is that chemical or genetic IDO inactivation does not lead to autoimmunity suggesting that IDO plays a minimal role in maintaining tolerance (Mellor & Munn 2008). These findings led to studies of transplantable tumors such as Lewis lung carcinoma (LLC) which displayed attenuated growth in the presence of 1-MT (Friberg et al. 2002). IDO catabolizes tryptophan (Trp) generating the metabolite kynurenine, modulated by the immunosuppressive molecule CTLA4-Ig and reversed by the action of 1-MT (Grohmann et al. 2002).

T cell suppression by regulatory T-cells (Treg) is consistent with a mechanism involving IDO suppression of T cell function (Fallarino et al. 2003). It was later discovered that dendritic cells (DC) and in particular, plasmacytoid (p)DC, in tumor draining lymph nodes (TDLN) produced IDO thought to be an important mechanism for suppression of host-antitumor T cell responses (Munn et al. 2004; Mellor et al. 2005). When IDO was blocked, CD4+ T cells converted from a phenotype blocking T cell function to expressing a proinflammatory phenotype aiding tumor immunity (Baban et al. 2009). In the TRAMP prostate cancer model, strong evidence is provided that IDO expression in TDLN was more essential for TRAMP tumor incidence than IDO expression in tumor cells themselves (Kallberg et al. 2010). IDO also functions to suppress autoimmune colitis or viral replication indicating a complex physiology of IDO expression that assumes new properties when supporting tumor progression (Hoshi et al. 2010; Ciorba et al. 2010). The problem that IDO poses for successful immune targeting of tumors was illustrated by reports showing that CpG DNA treatment induced CD19+ pDC to activate Tregs in an IDO-dependent manner, leading to T cell suppression (Mellor et al. 2005). IDO is a significant counterweight to immune-mediated therapy, and is likely a significant obstacle to achieving a successful outcome for vaccine or immunotherapeutic strategies in cancer patients (Katz et al. 2008).

IDO molecular inhibitors. Tumor progression is often preceded by rising IDO levels either in serum or expressed by tumor resident pDC. Inhibition approaches for IDO have been the object of intense research, especially chemical inhibition of IDO catabolism of Trp (Lob et al. 2009; Macchiarulo et al. 2009; Predergast 2008). Alternatively, molecular approaches in which IDO levels are reduced using inhibitory RNA (RNAi) have also been developed using the murine B16 melanoma model (Zheng et al. 2006; Yen et al. 2009). B16 cells were transfected with a plasmid expressing a different shIDO than the RNAi candidate and administered s.c. to C57BL/6 (B6) mice. In a therapeutic setting, either intra-tumoral injection of synthetic IDO-RNAi or topically applied shIDO-expressing plasmid were effective at delaying tumor growth compared to control treatments. Similar to chemical approaches, the published shIDO or RNAi therapeutics were both T cell dependent—in marked contrast to the ST approach described in the Examples below.

IDO chemical inhibitors. It has been shown that IDO expression is regulated by the cancer suppression gene bin1, and cytotoxic agents combined with 1-MT could effectively reverse immunosuppression caused by IDO (Muller et al. 2005). bin1 and 1-MT blockage of IDO suppression of tumor control are T cell dependent, because nude (nu) or Rag1-KO (Hou et al. 2007) (knockout) immunodeficient or in vivo CD4 T cell depleted immunocompetent mice failed to show an effect of 1-MT to control tumor growth (Muller et al. 2005). It was also discovered that stereoisomers of 1-MT differentially inhibit IDO enzymatic activity (Hou et al. 2007). It was later shown that the D-isomer of 1-MT was specific for IDO, since in IDO-KO mice the treatment lost its effectiveness (Hou et al. 2007). Employing combination therapy with cytotoxic drugs such as cyclophosphamide (CY), paclitaxel, or gemcitabine, 1-DL-MT or its D-isomer showed superior activity than single agents (Hou et al. 2007). In the B16 model described in the Examples below, shIDO-ST suppressed tumor growth in IDO-KO mice, whereas the D-isomer of 1-MT was ineffective in controlling tumor growth in combination with CY in IDO-KO or nu/nu mice (Hou et al. 2007). Celecoxib, a Cox2 inhibitor indirectly modulates IDO expression through prostaglandin E2 (PGE2), a direct effector of IDO protein levels (Basu et al. 2006). Since 1-MT is a low potency compound with a Ki=34 µM (Kumar et al. 2008), studies to establish the structural requirements of inhibitors with far lower Ki are being conducted.

The plant compound Brassinin is active against IDO in B6 mice, but is ineffective in both nu and IDO-KO mouse models using B16 tumor (Banerjee et al. 2008; Gaspari et al. 2006). Potent IDO metabolic inhibitors based on a napthoquinone structure have vastly superior Ki and are active in B6 mice, yet ineffective in both nu and IDO-KO models (Kumar et al. 2008). Remarkably, Vitamin K3 (menadione) is a member of this class and demonstrates substantial antitumor activity. An alternative approach utilizes hydroxyamidine, a different chemical structure that has strong activity against murine tumors in B6 mice with lesser efficiency in nu or IDO-KO models (Liu et al. 2010; Koblish et al. 2010). The hydroxyamidine inhibitor has similar activities in both human and murine tumor systems and demonstrates lowering of kynurenine/tryptophan (Kyn/Trp) levels (Liu et al. 2010). Ethyl pyruvate, a common preservative interferes with the induction of IDO synthesis through a signal transduction mechanism. Though it is effective in B6 mice, it failed to contain tumor growth in both nu and IDO-KO models (Muller et al. 2010). Thus, most published chemical and RNA-based IDO inhibitors act by disrupting cellular IDO expression or function resulting in tumor growth regression in IDO+ mouse strains, yet are ineffective in nu or IDO-KO mouse models.

IDO in the tumor microenvironment. In several tumor models, particularly B16, a population of pDC in TDLN were shown to activate resting CD4+CD25+FoxP3+ Tregs to become potent suppressors of T cell function (Sharma et al. 2007). This suppression was blocked by 1-MT and forms a mechanistic basis for the T cell dependence of its inhibitory function. Suppression by pDC is dependent on the PD-1 pathway, though IDO had no affect once Tregs became activated. Treg suppression was associated with the GCN2 pathway which is activated by reduced levels of amino acids such as might occur if IDO depleted Trp (Harding et al. 2003; Munn et al. 2005). The GCN2 and PD1 pathways that mediate IDO suppression are consistent with a T cell dependent mechanism for IDO inhibitors, though surprisingly different from shIDO-ST which is independent of CD4+ or CD8+ T cells based on an in vivo depletion study. A follow-on study showed that IDO expressed in TDLN supported Treg suppressive phenotype while blockade of IDO activity transformed Tregs into polyfunctional T helper-17 cells (Sarma et al. 2009). It is not yet known whether IDO produced by tumor infiltrating DCs, tumor cells, or both is partially responsible for tolerance induction. shIDO-ST functions equally well in B6 or IDO-KO mice suggesting that tumor-expressed IDO may be essential for tumor growth. Recent findings demonstrate that IDO is recognized as a foreign Ag, and a T cell response recognizes AML blasts and IDO-expressing DC, a major immune inhibitory population (Sorensen et al. 2009). A follow-up study showed that IDO-specific T cells regulated DCs and tumor cells (Sorensen et al. 2011). Similarly, a recent report demonstrated that IDO2 generates a cytotoxic T cell response to IDO-expressing tumor cells (Sorensen et al. 2011). These facts illustrate how tumors overcome host immunity by implementing multiple immune suppression pathways Thus, according to some embodiments and as described in detail in the Examples below, immunosuppression by IDO may be disrupted by the ST silencing strategy described herein, and is effective as a single agent to control tumor growth. Unlike the mechanism of prior IDO inhibitors described above that are contingent on a competent adaptive T cell response (Predergast 2008), the shIDO-ST strategy is T cell independent and stimulates abundant intratumoral infiltration of Gr1-F/Ly6G+ neutrophils (Neut, also referred to herein as polymorphonuclear neutrophils (PMN)). Further, the observation of increased specific colonization of s.c. tumors by shIDO-ST gives this system a qualitative advantage over alternative delivery strategies because of the cell destructive properties of ST that are localized directly in the tumor microenvironment.

The ability of the shIDO-ST to recruit polymorphonuclear neutrophils (PMNs) to the tumor site gives the single agent the capacity to completely eradicate tumors, which includes cancer cells and vascularized stroma, significantly decreasing the potential for tumor regrowth. As such, PMNs hold considerable promise as efficient mediators of anticancer activity (Di Carlo et al. 2001a; Di Carlo et al. 2001b; Dallegri & Ottonello 1992). They are the most abundant leukocyte in the body and are constantly regenerated in vast numbers each day. Several anticancer therapies have been shown to employ PMNs as an important component of their antitumor efficacy (Stockmeyer et al. 2003; Hernandez-ilizaliturri et al, 2003). Nevertheless, such therapies have been limited by disseminated toxicity resulting from systemic delivery, dependence on adaptive immunity, which is often compromised in cancer patients, and, above all, immunoregulatory constituents of the tumor microenvironment that suppress PMN killing of cancer tissue (Chen et al. 2003). One major immunoregulatory element of tumors is the overexpression of IDO, a tryptophan-catabolizing enzyme that acts as a potent suppressor of adaptive immunity and, more recently, has been implicated in inducing apoptosis of PMN (Van der Sluijs et al. 2011). Despite many notable insights into the benefits of inactivating IDO to enhance adaptive antitumor responses, no efficacious drugs or therapies have proven effective in human clinical trials (Lob et al., 2009). Furthermore, no IDO inhibition strategy has ever been devised to augment innate antitumor responses. As described in the Examples below, a tumor-targeting *Salmonella typhimurium* (Low et al. 2004; Pawelek et al. 2003) transformed with an shRNA plasmid against the immunosuppressive molecule indoleamine 2,3-dioxygenase (Munn et al. 2004) (shIDO-ST) that, when delivered systemically into mice, causes significant PMN tumor infiltration and massive intratumoral cell death. It was shown that shIDO-ST treatment works independently of host IDO and adaptive immunity, which has important implications for use in immunocompromised cancer patients. It was also demonstrated that shIDO-ST treatment increases reactive oxygen species (ROS) produced by infiltrating PMNs and immunodepletion of these subsets completely abrogates tumor control. These findings present a viable addition or alternative to current cancer immunotherapies.

Arginase 1 as a Single Modality Cancer Immunotherapy Regimens

In one embodiment, an anti-immunosuppressant vector that expresses an shRNA to silence Arginase 1 expression may be sufficient to be used alone as a single modality cancer immunotherapy regimen. As shown in the Examples below, shArg1 alone is sufficient to suppress tumor growth. Further, combination treatment with shArg1 and 3342Max had no additional therapeutic benefit. This in vivo silencing of Arginase-1 is effective due to a mechanism of action that involves cell populations from both innate (MDSC) and adaptive (CD4$^+$ and CD8$^+$ T cells) immune systems.

MDSC were originally identified in tumor-bearing mice as cells that co-express CD11b and GR1. Currently, two main MDSC populations have been characterized: monocytic MDSC and granulocytic MDSC. In tumor-bearing mice, the granulocytic subset is the more prevalent population of MDSC, which suppress antigen-specific CD8 T cells predominantly by producing ROS. However, the monocytic subset is more immunosuppressive on a per cell basis, and in human studies, the number of monocytic MDSC correlates directly with T cell suppression and poor clinical outcome (Dolcetti et al. 2010; Youn et al. 2008; Movahedi et al. 2008; Mandruzzato et al. 2009). Despite the differences in their immunosuppressive capabilities, both subsets of MDSC overexpress Arginase-1 and iNOS (Youn et al. 2012; Brandau et al. 2011; Lu et al. 2011; Bronte et al. 2005; Nagaraj et al. 2007; Molon et al. 2011).

MDSC have been reported to mediate their immunosuppressive effects via an array of mechanisms involving both innate and adaptive immune cells. One of the reported mechanisms involves the activation and expansion of Tregs. The mechanism by which these cells enhance the expansion of Tregs and their suppressive function is not well established but direct cell-cell contact via CD40-CD40L (Pan et al. 2010), secretion of suppressive cytokines such as IL-10, TGF-B (Huang et al. 2006) and also the expression of Arginase-1 (Serafini et al. 2008) are likely to be involved.

One mechanism employed by MDSC to non-specifically diminish the anti-tumor effects of a variety of effector cells present in the local tumor environment is the generation of oxidative stress, which is caused by the production of ROS and reactive nitrogen species. Peroxynitrite and hydrogen peroxide are generated by the combined and cooperative action of Arginase-1, iNOS and NADPH oxidase all expressed by MDSC. These cells have been shown to generate large amounts of reactive species, which interfere and block T cell function at different levels. Such interference includes loss of CD3 ξchain expression (Schmielau et al. 2001) and alterations in IL-2 receptor signaling (Mazzoni et al. 2002) due to the nitration/nitrosylation of amino acids like cysteine, methionine, tryptophan and tyrosine resulting in the desensitization of the T cell receptor which is required for T cell proliferation and survival. In addition, recent data demonstrate that the nitration of chemokines (e.g. CCL2) has a profound impact in the migration of T cells to the tumor environment, in addition to an enhanced recruitment of MDSC to this site (Molon et al. 2011).

As discussed in the Examples below, it was shown that all three myeloid MDSC subsets, including macrophages, granulocytic MDSC and monocytic MDSC, express significantly less ROS within the tumor of mice treated with shArg1. Further, CD45⁻ tumor/stromal cells also generate significantly less ROS when Arginase-1 is inhibited. These results are consistent with a model in which Arginase-1 lowers the L-Arginine concentration in the microenvironment, thus inducing iNOS to produce $O_2^-$ in addition to NO, the exclusive product of iNOS at higher L-Arginine concentrations. NO reacts with $O_2^-$, giving rise to peroxynitrite ($ONOO^-$), a highly reactive oxidizing agent that nitrates tyrosines on proteins. Peroxynitrites can induce apoptosis in T lymphocytes by inhibiting activation-induced protein tyrosine phosphorylation (Brito et al. 1999) or by nitrating a component of the mitochondrial permeability transition pore, which causes release of death-promoting factors, such as cytochrome C (Aulak et al. 2001; Bronte et al. 2003). Furthermore, this change in microenvironment was not observed in the spleen, as these subsets of myeloid cells showed no differences in ROS production (FIG. 40C). As such, delivering the shArg1 using a ST vector can activate the immune response locally, specifically where it is needed, preventing potential systemic tissue damage and autoimmunity.

Further, Example 7 illustrates that the therapeutic effects of shArg1 may be mediated via the action of iNOS and its role in the generation of ROS/RNS. Arginase-1 activation has been reported to limit L-Arginine as a substrate for iNOS and thereby negatively regulate its activity (Munder et al. 1999). Both enzymes have been reported to metabolize L-Arginine at similar rates (Fligger et al. 1999), but depletion of cytosolic L-Arginine in MDSC by Arginase-1 induces the switch in iNOS activity shifting its function from the production of mostly NO to peroxynitrites (Bronte et al. 1003; Xia et al. 1997; Xia et al. 1998). In summary, the results shown in the Examples below suggest that shArg1 treatment inhibits the production of reactive species by modulating iNOS activity. Therefore, anti-tumor effects may be seen by inhibiting Arg1 or iNOS.

Methods for Treating Cancer

The therapeutic compositions and associated combination and single modality cancer immunotherapy regimens described above may be used in methods to treat cancer, to attenuate the growth of a tumor or to regress a tumor. The methods described herein may be used to treat or attenuate the growth of any cancer or tumor type. Cancers and tumor types that may be treated or attenuated using the methods described herein include but are not limited to bone cancer, bladder cancer, brain cancer, breast cancer, cancer of the urinary tract, carcinoma, cervical cancer, colon cancer, esophageal cancer, gastric cancer, head and neck cancer, hepatocellular cancer, liver cancer, lung cancer, lymphoma and leukemia, melanoma, ovarian cancer, pancreatic cancer, pituitary cancer, prostate cancer, rectal cancer, renal cancer, sarcoma, testicular cancer, thyroid cancer, and uterine cancer. In addition, the methods may be used to treat tumors that are malignant (e.g., primary or metastatic cancers) or benign (e.g., hyperplasia, cyst, pseudocyst, hematoma, and benign neoplasm).

In some embodiments, a method for treating cancer may include administering a therapeutically effective amount of a combination cancer immunotherapy regimen, such as those described herein, to a subject.

In other embodiments, a method for treating cancer may include administering a therapeutically effective amount of a single *Salmonella* expressing a single shRNA, such as those described herein, to a subject.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A "therapeutically effective amount," "effective amount" or "effective dose" is an amount of a composition (e.g., a therapeutic composition or agent) that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

Figure 11:
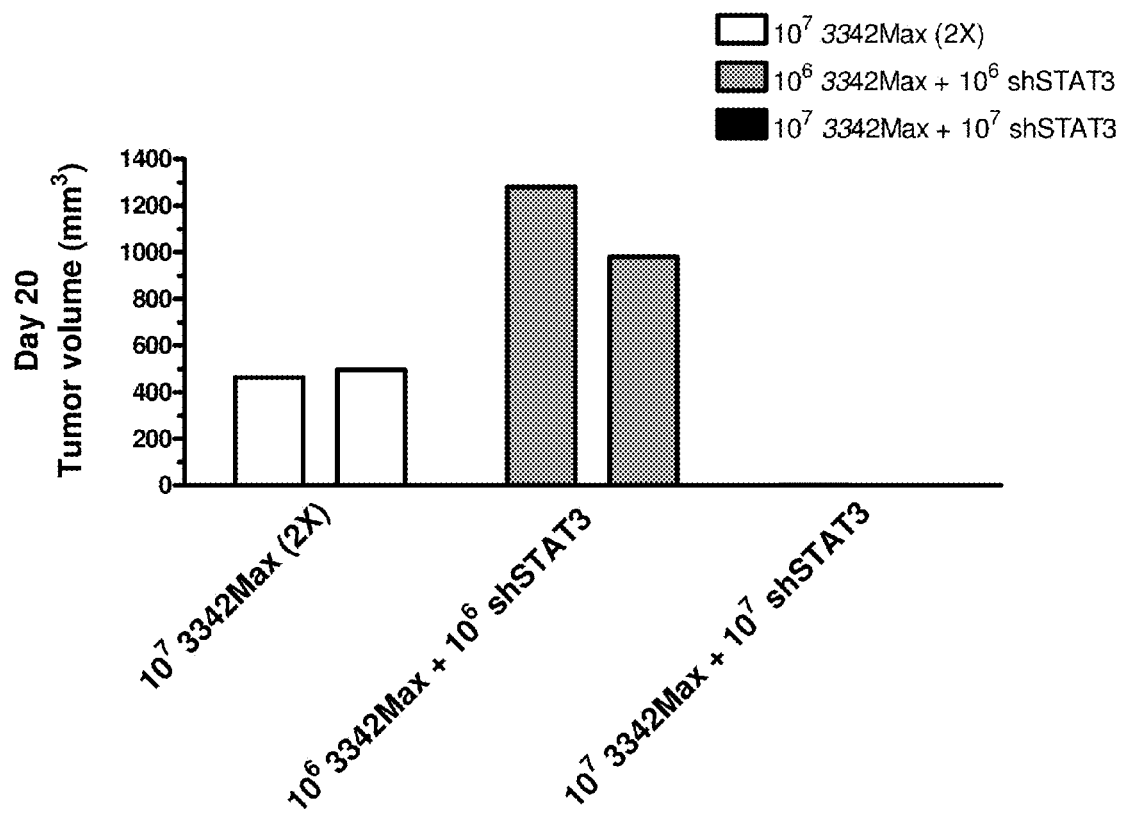
FIG. 11 is a bar graph illustrating that the combination treatment of 3342Max (10⁷ cfu) with YS1646-shSTAT3 (10⁷ cfu) is also effective in preventing lymphoma tumor growth in a day 3 EL4A2 Kb therapeutic model in HHDII mice compared to 3342Max treatment alone or at lower concentrations of each. These results provide evidence that this combination treatment may have broad application to various tumor types.

The endpoint for the models described herein is tumor growth attenuation, regression or rejection using a stringent therapeutic approach. Therefore, according to some embodiments, methods of suppressing tumor growth or regressing a tumor (i.e., reducing tumor volume) in a subject are provided herein (FIG. 11).

According to the embodiments described herein, the methods for treating cancer, attenuating tumor growth or regressing a tumor, may include administering, to a subject, a therapeutically effective dose of a single modality cancer treatment regimen or a combination cancer treatment regimen. In some embodiments, the single modality cancer treatment regiment includes administering a single *Salmonella* strain that includes an expression vector or plasmid that expresses an shRNA molecule that disrupts tumor derived immune suppression. In this case, the single *Salmonella* strain may be effective on its own, without administration of additional therapeutic compositions. The single *Salmonella* strain may be any attenuated strain that is suitable for carrying a plasmid that expresses shSTAT3, shIDO1, shIDO2, shArg1, shiNOS, or TGF-β, including, but not limited to, YS1646, RE88, LH430, SL7207, x8429, x8431, x8468. In one embodiment, the single *Salmonella* strain is YS1646 and the associated plasmid expresses shIDO1.

In other embodiments, the combination cancer treatment regimen may include a therapeutically effective amount of at least one tumor antigen vaccine and a therapeutically effective amount of at least one composition that disrupts tumor-derived immune suppression. Alternatively, a single *Salmonella* that disrupts tumor-derived immune suppression can be administered effectively on its own, without a second *Salmonella* delivering a tumor vaccine. The tumor antigen vaccine may include a first *Salmonella* strain that carries a plasmid that expresses survivin and the composition that disrupts tumor-derived immune suppression may include a second *Salmonella* strain that carries a plasmid that expresses shRNA that suppresses the expression of an immunosuppressive target gene or protein in the tumor microenvironment. The first *Salmonella* strain may be an attenuated MVP728 (purD-/htr-) strain that carries a plasmid that expresses SVN or CO-SVN. The second *Salmonella* strain or in some cases the ONLY given strain may be any attenuated strain that is suitable for carrying a plasmid that expresses shSTAT3, shIDO1, shIDO2, shArg1, shiNOS, or TGF-β, including, but not limited to, YS1646, RE88, LH430, SL7207, x8429, x8431, x8468. In one embodiment, the second *Salmonella* strain is YS1646.

According to some embodiments described herein, the two systemically delivered therapeutic compositions described above are inadequate to control tumor growth alone, but are effective when administered in combination with each other in a combined cancer therapy. Specifically, attenuated *Salmonella typhimurium* (ST) carrying either a STAT3-specific shRNA plasmid (e.g., shSTAT3-ST or YS1646-shSTAT3) or an SVN expression plasmid (3342Max) were administered consecutively and observed to function synergistically leading to effective tumor rejection. The combined approach improves the prospects for successful vaccination against cancer by altering the tumor microenvironment to be less antagonistic to tumor infiltrating T cells such as those stimulated by vaccine-encoded TAAs.

As described in detail in the Examples below, an intravenously administered shRNA against STAT3 acts synergistically with an oral DNA vaccine against SVN in a therapeutic setting, resulting in suppression of subcutaneous B16F10 melanoma growth. The in vivo suppression of B16F10 tumor growth is the result of increased tumor cell apoptosis, as determined by annexin V staining, possibly caused by an increased level of SVN-specific CD8+ T cells within the tumor. Additionally, suppression of tumor-expressed SVN by silencing STAT3 could contribute to the observed increase in apoptosis (Aoki et al. 2003). The Ki67+/Ki67-ratios also indicated that these intratumoral T cells were actively proliferating, thereby supporting the notion that shRNA against STAT3 attenuated immunosuppression within the tumor microenvironment. Moreover, the fact that neither the vaccine nor shRNA against STAT3 alone was effective to control tumor growth suggests that the combined treatments acted synergistically. These data support that implementing successful immunotherapy may be ineffective without a receptive tumor microenvironment generated through additional modalities such as shRNA to inhibit immunosuppression.

In one embodiment, the tumor antigen vaccine and the composition that disrupts tumor-derived immune suppression (i.e., the first and second *Salmonella* strains and associated plasmids) are administered in combination with each other. "In combination" or "in combination with," as used herein, means in the course of treating the same disease in the same patient using two or more agents, drugs, treatment regimens, treatment modalities or a combination thereof, in any order. This includes simultaneous administration, as well as in a temporally spaced order of up to several days apart. Such combination treatment may also include more than a single administration of any one or more of the agents, drugs, treatment regimens or treatment modalities. Further, the administration of the two or more agents, drugs, treatment regimens, treatment modalities or a combination thereof may be by the same or different routes of administration.

In the embodiments described herein, a single *Salmonella* strain may be administered, in combination with an expression vector that expresses an agent that inhibits, suppresses or blocks IDO1, IDO2, STAT3, Arginase 1, iNOS, or TGF-β for the regression and/or attenuation of tumor growth in cancer.

Such methods may include steps of administering to the subject a therapeutically effective amount of a vaccine against a TAA and then administering to the subject an agent that inhibits, suppresses or blocks an immunosuppressive target gene or protein in the tumor microenvironment. In other circumstances, the vaccine is not required, and only an agent that inhibits, suppresses or blocks an immunosuppressive target gene or protein in the tumor microenvironment is required.

SVN was used to provide the widest versatility for vaccination because it is a ubiquitously expressed TAA. In contrast to *Salmonella*-based SVN vaccines used in previous studies, which have been relatively ineffective when used alone, the SVN vaccines described herein do not require additional cytokine or chemokine components for effectiveness (Xiang et al. 2005; Xiang et al. 2005; Siong et al. 2009). Similar to other reports describing *Salmonella* routes of administration was the use of oral systemic administration of *Salmonella* transformed with SVN expression plasmids described herein. This approach has the advantage of practicality because *Salmonella* are efficiently recognized by antigen processing macrophages in the gut or other mucosal sites (Evans et al. 2003; Catic et al. 1999).

The therapeutic compositions described herein may be administered by any suitable route of administration. A "route of administration" may refer to any administration pathway known in the art, including but not limited to aerosol, enteral, nasal, ophthalmic, oral, parenteral, rectal, transdermal (e.g., topical cream or ointment, patch), or vaginal. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In one embodiment, the tumor antigen vaccines described herein (e.g., an SVN or CO-SVN *Salmonella*-based vaccine and associated expression plasmids) are administered orally and the compositions that disrupt tumor-derived immune suppression described herein (e.g., YS1646-shSTAT3 YS1646-shIDO1, YS1646-shArg1 or YS1646-shiNOS) are administered intravenously.

Figure 7:
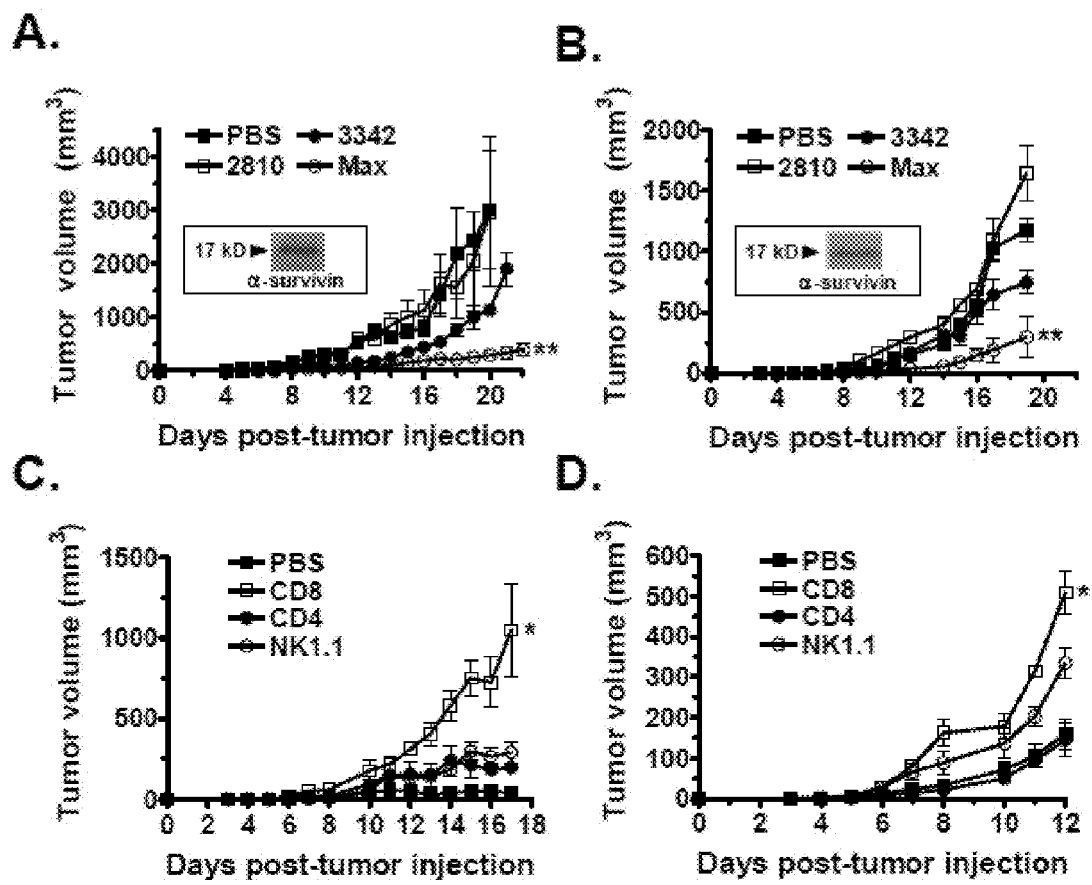
FIG. 7 shows that codon optimization of SVN enhances suppression of tumor growth in murine models of lymphoma and melanoma. Insets of A and B, lysates of the lymphoma (EL4A2 Kb) and melanoma (B16F10) cell lines were analyzed by Western blot for SVN expression. Groups of mice were injected subcutaneously (s.c.) with (A) EL4A2 Kb or (B) B16F10 on day 0 and then vaccinated with MVP728-2810, -3342, -3342Max, or PBS on day 3. C and D, Following s.c. injection of tumor on day 0, mice bearing palpable EL4A2 Kb (C) or B16F10 (D) tumor were vaccinated twice with 3342Max (days 3 and 7) and depleted of immune subpopulations (day 5) by intraperitoneal injection of 200 μg of anti-CD8 mAb (clone H35), anti-CD4 mAb (clone GK1.5), or anti-NK1.1 mAb (clone PK136) with a maintenance dose every 3 days thereafter (Ishizaki et al. 2010).

In addition to the studies directed to melanoma cancer described above, the methods for treating cancer and attenuating tumor growth described herein may be applied to a wide variety other cancers and tumors. For example, administering survivin (3342Max) in combination with YS1646-shSTAT3 efficiently prevents growth of not only melanoma tumors, but also lymphoma tumors (FIG. 7).

Figure 15:
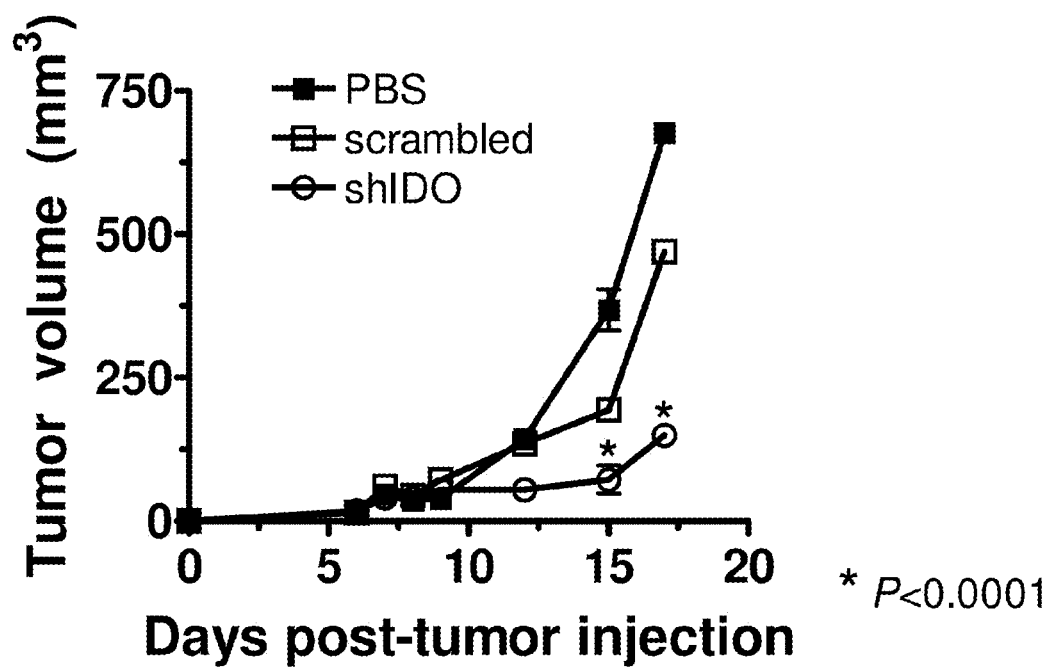
FIG. 15 is a graph illustrating the effect of intravenous injection of attenuated $Salmonella$ strain YS1646 that carries shIDO1-9 (YS1646-shIDO1) in a Pan02 (pancreatic) murine tumor model. Mice were treated with PBS, YS1646-scrambled or -shIDO1 when subcutaneously injected Pan02 tumors reached ≥5 mm in diameter. Tumor volume was assessed up to 18 days post-tumor challenge.

In addition to the studies directed to melanoma cancer described above, the methods for treating cancer and attenuating tumor growth described herein may be applied to a wide variety of other cancers and tumors. For example, administering YS1646-shIDO efficiently prevents growth of not only melanoma tumors, but also pancreatic tumors (FIG. 15). The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Construction and Evaluation of SVN Expression Vectors

Materials and Methods

Animals and tumor lines. C57BL/6 (Jackson) and transgenic HLA-A2 HHDII mice (Pascolo et al. 1997) (6-8 weeks old) were obtained from breeding colonies housed at the City of Hope (COH) Animal Research Center (Duarte, Calif.). The EL4-A2 Kb murine lymphoma (Dr. Linda Sherman, Scripps Research Institute, La Jolla, Calif.) and B16F10 murine melanoma cell lines (Drs. Hua Yu and Marcin Kortylewski, COH, Duarte, Calif.) were gifts. Cell lines were maintained at 37° C., 5% CO2 in DMEM containing 10% fetal bovine serum.

Tumor challenge, vaccination, and shRNA therapy. For tumor challenge, $5 \times 10^5$ EL4A2 Kb or $10^5$ B16F10 tumor cells were injected subcutaneously into HHDII or C57BL/6 mice, respectively. Tumor growth was monitored daily or every other day using a caliper (tumor volume=Length×Width×Height). For testing vaccination alone, MVP728 carrying 2810, 3342 or 3342 Max were administrated by gavage twice at days 3 and 7 at $10^8$ cfu in C57BL/6 mice and $10^7$ cfu in HHDII mice.

Bacteria strains. *S. typhimurium* strains MVP728 (purD-/htrA-) and YS1646 (ATCC#202165) were cultured by shaking at 37° C. in LB or LB-O media.

*Salmonella* SPI2 expression vectors, and generation of recombinant *Salmonella*. pWSK29 constructs containing the SPI2 expression cassettes for LisA (2810) or SVN (3342) are described elsewhere (Xiong et al. 2009). For construction of pWSK29 encoding *Salmonella* codon optimized survivin (CO-SVN), 2810 was digested with XbaI/EcoRV to release the LisA fragment from the pWSK29 backbone. The gel purified pWSK29 backbone was used to clone the synthesized CO-SVN gene (Genscript, Piscataway, N.J.) engineered with XbaI/EcoRV sites for in frame fusion with the sseF gene. SPI2 expression vectors were electroporated into *S. typhimurium* strain MVP728 with a BTX600 electroporator using a 0.2 cm gap cuvette (BTX, San Diego, Calif.) at the following settings: 2.5 kV, 186 ohms, 50 μF.

Western Blot Analysis. A Western blot for *Salmonella* expression of SVN was carried out as described previously (Xiong et al. 2009). Briefly, 3342 and 3342Max were grown overnight at 37° C. in a MOPS based buffer (Sigma) containing either low phosphate (113 μM) to induce SPI2 expression or high phosphate (25 mM) which does not induce. Bacterial pellets were boiled in SDS loading buffer and equal amounts of lysate were loaded. Blots were probed using a monoclonal rabbit antibody (ab76424) against SVN (Abcam, Cambridge, Mass.).

Optimization of SVN Improves Recombinant Antigen Expression

Figure 5:
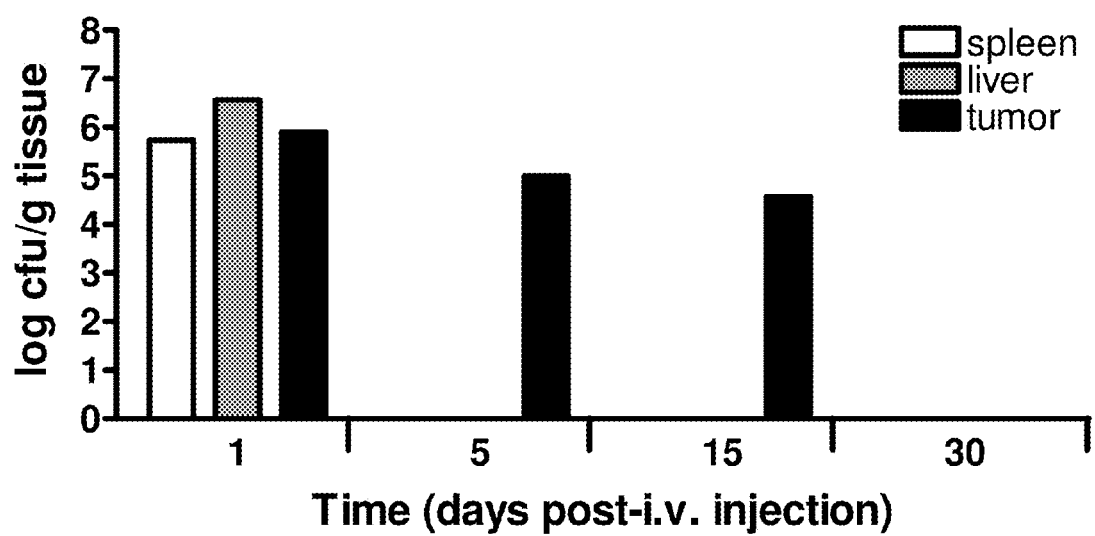
FIG. 5 is a bar graph illustrating the tissue distribution of intravenous (i.v.) injection of attenuated *Salmonella* strain YS1646 in B16F10 tumor-bearing C57BL/6 mice.

The SVN tumor antigen was used to study its role in controlling tumor growth after oral administration of *Salmonella typhimurium* carrying an SVN-expressing plasmid. As described herein, *Salmonella typhimurium* is advantageous at least because of its tropism for hypoxic environments, which is a property of most tumors. This makes the delivery a good choice for targeting tumors. Five different commonly used *Salmonella typhimurium* (ST) strains were examined (RE88, SL7207, LH430, X8429 and YS1646). It was discovered that YS1646 (also known as VNP20009) dwelled longest in the B16 tumor after clearance from somatic tissues of tumor bearing B6 and that YS1646 was detected exclusively in tumors 15 days post i.v. injection, whereas there were no cultivable bacteria in any somatic tissue (FIG. 5).

Previous work using the MVP728 bacterial vector transformed with plasmid 3342, which expresses SVN, demonstrated partial success in rejecting murine models of colon carcinoma and glioblastoma (Xiong et al. 2009).

Non-codon optimized SVN (FIG. 20) expression from 3342 was found to be suboptimal (or minimal) when compared to the expression of the bacterial protein LisA from 2810 (FIG. 6A). To determine whether codon optimization (CO) of SVN to *Salmonella* preferred codons would allow for increased stability and protein expression leading to greater SVN-specific anti-tumor effects following vaccination, a *Salmonella typhimurium* CO-SVN sequence was generated using an online algorithm (JCat Codon Adaptation Tool; www.jcat.de) and then synthesized (Genscript). As shown in FIG. 6B, the low copy plasmid pWSK29 was engineered to express the SPI2 chaperone protein sscB (Dai & Zhou 2004) and sseF protein fused to either LisA (2810), SVN (3342), or CO-SVN (3342Max) for expression and secretion by MVP728. According to the embodiments described herein, the expression of these genes would be regulated by the SPI2 specific promoter for sseA.

FIG. 6C shows the results of CO's effect on SVN expression by growing the recombinant *Salmonella* in SPI2-inducing conditions (Deiwick et al. 1999) (FIG. 6C). Under non-inducing conditions (PCN-FP), no significant expression of SVN was observed. However, under SPI2 inducing conditions (PCN-P), SVN expression was significantly higher when a minimally optimized codon version of SVN (FIG. 19) was fused to 3342 (3342 Min) or the maximally optimized codon version of SVN (FIG. 18) was fused to 3342 (3342Max) as compared to the non-optimized eukaryotic codon version of SVN, 3342. SVN expression and secretion by 3342Max was further evaluated by infecting the mouse macrophage line RAW264.7 with either 3342 or 3342Max to determine intracellular expression of SVN by immunofluorescence. As shown in FIG. 6D (HA-survivin panel), SVN expression was greater in 3342Max (characterized by more foci) as compared to 3342. Further, mAb staining for both the LPS (LPS-St) panel and the HA (HA-survivin) panel localized to the cytoplasm and overlapped in the Merge panel, independent of the nuclear DAPI staining (DAPI panel). These data suggest that optimization of SVN tailored to preferred *Salmonella* codons greatly improves recombinant antigen expression.

Initial trials using 3342 were only partially successful against small tumors that had just a few days to develop vascularization (FIG. 7). The problem was solved by investigating the expression levels of SVN compared to the bacterial LisA and finding significantly lower levels of SVN by Western blot analysis compared to the bacterial LisA protein under almost identical conditions (FIG. 6A). Since the bacterial LisA protein was so heavily expressed in *Salmonella*, the sequence of SVN from was changed from human to *Salmonella typhimurium* preferred codons to achieve the same goal. In preliminary experiments, a gradation of effectiveness was found against growth of established subcutaneous tumors dependent on expression levels (non-codon optimized vs. codon optimized). The predictability of the increasing effectiveness to reject established tumors made it unnecessary to continue to simultaneously evaluate all forms, and the most effective form (3342Max) was exclusively used in all further comparisons. Ultimately, it was found that control of B16F10 tumor growth using 3342Max vaccination worked shortly after tumor challenge, when tumors became immediately palpable. However, upon treatment of mice with larger B16F10 tumors of volumes >50 mm$^3$, the vaccine was unable to attenuate tumor growth. This may be due to immunosuppressive mechanisms becoming more established as the tumor grows, rendering the primary vaccine immunotherapy alone less effective (Polak et al. 2009; Deepak & Acharya 2010).

CO-SVN Enhances Suppression of Tumor Growth

To determine whether enhanced expression of SVN by 3342Max translated into a more efficacious vaccine, two murine tumors in the B6 (H-2b) background were evaluated: EL4A2 Kb lymphoma and B16F10 melanoma that overexpress SVN (insets of FIGS. 7A, 7B). In both murine models, subcutaneously injected tumor cells were allowed to grow until a palpable tumor was present, generally <10 mm$^3$. Mice were then gavaged twice (4 days apart) with either PBS or MVP728 harboring either 2810, 3342, or 3342Max constructs. In both tumor models, 3342Max vaccination was superior to all other experimental treatments in attenuating tumor growth (FIGS. 7A and 7B). It was then determined which lymphocyte subsets were most responsible for the attenuation of tumor growth by carrying out in vivo antibody depletion of CD8+, CD4+, and NK populations in tumor bearing mice vaccinated identically as mice shown in FIGS. 7A and 7B (see FIGS. 7C and 7D). Both tumor models showed depletion of CD8+ T lymphocytes that resulted in significant loss of tumor control, while only in the B16F10 model was there also an effect of NK depletion (Kortylewski et al. 2009a). These data suggest that vaccination with 3342Max elicits superior CD8+ T cell responses that limit tumor growth, likely a result of enhanced SVN expression.

Example 2 shRNA Suppression of STAT3 or IDO1: Effect on Tumor Growth Alone and in Combination with SVN Vaccines Materials and Methods In addition to those described in Example 1 above, the following materials and methods were used in the studies described below.

shRNA Plasmids and Generation of Recombinant *Salmonella*. Constructs against STAT3 and IDO1 were cloned separately into pGFP-V-RS (Origene, Rockville, Md.) or pLKO.1-puro (Sigma, St. Louis, Mo.) and tested for STAT3 and IDO1 silencing by stable transfection of B16F10 cells or co-transfection of an IDO-expressing plasmid followed by Western blot analysis using polyclonal rabbit antibody against STAT3 (Santa Cruz Biotech, Santa Cruz, Calif.) or IDO1 (Millipore, Temecula, Calif.).

The pGFP-V-RS vector containing the 29-mer shRNA sequence ACCTGAAGACCAAGTTCATCTGTGTGACA (SEQ ID NO:4) (ID#GI556360; shSTAT3#60) exhibited >70% knockdown of STAT3 expression by Western blot (FIG. 8A) and was selected for generation of recombinant YS1646. The pGFP-V-RS vectors containing the shRNA sequences corresponding to shIDO1-9 (FIG. 12; SEQ ID NO:6) also exhibited significant knockdown of IDO1, and were selected for generation of recombinant YS1646.

Selected shRNA plasmids were electroporated into *S. typhimurium* strain YS1646 with a BTX600 electroporator using a 0.2 cm gap cuvette (BTX, San Diego, Calif.) at the following settings: 2.5 kV, 186 ohms, 50 uF.

Tumor Challenge, Vaccination, and shRNA Therapy. For tumor challenge, 5×10$^5$ EL4A2 Kb or 10$^5$ B16F10 tumor cells were injected subcutaneously (s.c.) into HHDII or C57BL/6 mice, respectively. Tumor growth was monitored daily or every other day using a caliper (tumor volume=Length×Width×Height). For experiments using shRNA therapy alone, tumors were treated when they became palpable in the mouse (≥10 mm$^3$). For combined therapy, YS1646-STAT3 or -scrambled was first injected at 10$^7$ cfu in C57BL/6 mice when tumor volumes were ≥50 mm$^3$ followed by vaccination with 3342Max, 3342 or 2810.

Quantitative PCR for Detection of STAT3 Levels. Mice bearing palpable B16F10 tumors were i.v. injected with 10$^7$ cfu of YS1646-scrambled, -shSTAT3, or PBS twice, 4 days apart. At days 3, 7, and 10, mice (n=3) were sacrificed and RNA was extracted from tumor homogenates and used for generation of single strand cDNA (Fermentas, Glen Burnie, Md.). To quantitate STAT3 levels, SYBR®-Green qPCR analysis (BD Biosciences, Franklin Lakes, N.J.) using the following primers specific for STAT3 and the housekeeping gene GAPDH for normalization:

```
STAT3 Forward:
                                    (SEQ ID NO: 20)
5'-CATGGGCTATAAGATCATGGATGCGAC-3'

STAT3 Reverse:
                                    (SEQ ID NO: 21)
5'-AGGGCTCAGCACCTTCACC GTTATTTC-3'

GAPDH Forward:
                                    (SEQ ID NO: 22)
5'-CAAGGTCATCCATGACAACTTTG-3'

GAPDH Reverse:
                                    (SEQ ID NO: 23)
5'-GTCCACCACCCTGTTGCTGTAG-3'
```

Immunofluorescence staining. For detection of intracellular SVN expression from recombinant *Salmonella*, RAW264.7 murine macrophages seeded on coverslips were infected for 30 minutes at an MOI of 10 with wildtype MVP728, 3342, or 3342Max grown to late-log phase. Cells were then incubated overnight in DMEM-10 containing 10 μg/mL gentamicin. Cells were fixed/permeabilized with 1:1 acetone:methanol and then stained with conjugated antibodies FITC-LPS (Santa Cruz Biotech, Santa Cruz, Calif.) and PE-HA (Covance, Princeton, N.J.) overnight at 4° C. in the dark. Cells were stained with DAPI and then immediately imaged on an Axiovert 200 using live imaging software (Axiovision, Skokie, Ill.). Cells shown in FIG. 6 are representative of cells observed within multiple comparable fields.

Flow cytometry. Conjugated mAbs directed to PECy7-CD8 and PerCP-CD45 were purchased from BD Pharmingen (San Diego, Calif.) and mAb to APC-Cy7-CD4, FITC-Ki-67, Pe-Granzyme B, and FITC-annexin V were purchased from eBioscience (San Diego, Calif.). Intracellular Granzyme B, Ki-67 and annexin V staining were performed following the manufacturer's protocol (eBioscience). Samples were run on a FACS-Canto (Becton Dickinson, La Jolla, Calif.) and analyzed using FlowJo™ software (TreeStar, Ashland, Oreg.).

Cytotoxicity assay. Cytotoxicity against B16F10 melanoma cells in treated mice was determined with a standard $^{51}$Cr release assay at E:T ratios of 100:1, 20:1 and 4:1 (Ishizaki et al. 2010). Briefly, effectors used in the assay were derived from spleens of B16F10-bearing (≥25 mm3) C57BL6 mice (n=3) i.v. injected with either $10^7$ cfu of YS1646-shSTAT3 or -scrambled followed by gavage with $10^7$ cfu of 3342Max 4 days later. Mice were sacrificed ~1 week post-gavage and splenocytes were co-incubated with RMA-S cells loaded with SVN library (Ishizaki et al. 2010). Effectors were then co-incubated for 4 hours with 5,000 Cr51-loaded B16F10 targets in 96-well plates at ratios of 100:1, 20:1, and 4:1 (in triplicate). Radioactivity released into the supernatant was measured using a Cobra Quantum gamma counter (PerkinElmer). Percent specific lysis was calculated using the formula: (experimental release−spontaneous release)/(maximum release−spontaneous release)× 100.

Selection of shRNA Expression Plasmids and Suppression of mRNA Levels In Vitro and In Situ When subcutaneous B16F10 tumors were allowed to grow to moderate size (tumor volumes >50 mm$^3$), 3342Max vaccination had no efficacy to attenuate their growth when given as a single agent (data not shown). Because the 3342Max vaccine was determined to work efficiently in less demanding circumstances (see FIG. 7), failure in the more advanced setting may be the result of greater levels of tumor-derived immunosuppression (Anderson et al. 2007). To determine if the efficacy of the vaccine could be rescued, the tumor microenvironment was manipulated by silencing the tolerogenic molecule STAT3 (Yu et al. 2007; Kortylewski et al. 2009b; Kortylewski et al. 2008).

STAT3 or IDO1 mRNA expression were inactivated using shRNA expression plasmids, each carried by the tumor-targeting *Salmonella* strain YS1646 (Clairmont et al. 2000). Several commercially available shRNA plasmids (Origene and Sigma:Mission; SEQ ID NO:1-9) were tested to silence the expression of STAT3 or IDO1 in stably transfected B16F10 tumor lines or HEK293 cells co-transfected with an IDO1 expression plasmid (Origene), respectively. As shown by Western blot shSTAT3#60 (FIG. 8A) and shIDO-9 (FIG. 12) showed dramatic silencing (>70%) of the endogenous STAT3 or IDO1 when compared to a scrambled shRNA control plasmid. Other shSTAT3 or shIDO plasmids had intermediate to no effect on endogenous STAT3 or IDO1 expression.

Figure 16:
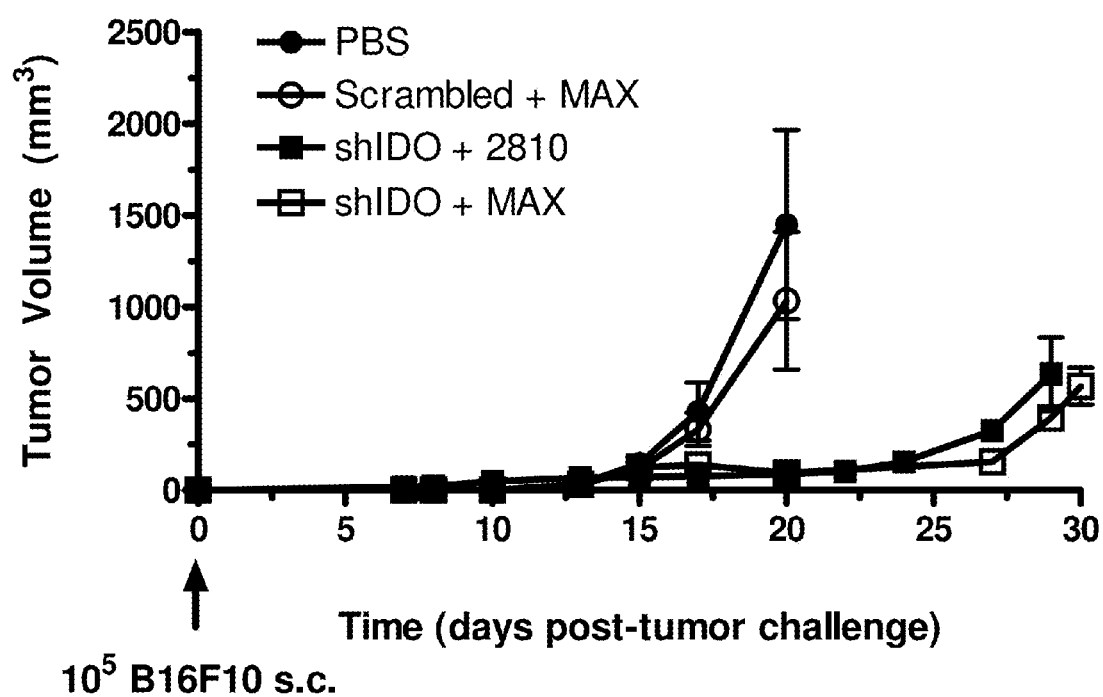
FIG. 16 is a graph illustrating the effect of intravenous injections of YS1646-shIDO1 in combination with 3342Max (MAX) in a B16F10 tumor-bearing C57BL/6 mouse model. The combined treatment showed no significant difference in tumor growth attenuation when compared to shIDO1 alone, indicating that shIDO is insensitive to such additions, it pairs will with other treatment groups and may be useful alone, without any additional treatments.

Targeted Silencing of STAT3 Combined with 3342Max Suppresses Tumor Growth in a More Aggressive Melanoma Tumor Model Next, a combination of shSTAT3 and 3342Max vaccination (shSTAT3+Max) was delivered in mice with significantly larger B16F10 tumors and compared to mice given 2810, shSTAT3 or PBS to determine whether suppression of STAT3 expression would be effective in increasing the efficacy of the vaccination. Mice bearing B16F10 tumors >50 mm$^3$ were systemically (i.v.) injected with $10^7$ cfu of YS1646-shSTAT3, scrambled, or PBS. Four days later, mice were gavaged with $10^7$ cfu of 3342Max, 2810, or PBS. As shown in FIG. 8C, the combination of shSTAT3 with 3342Max rescues the activity of the vaccination to attenuate tumor growth significantly better than control groups. These results suggest that the combination of shSTAT3 therapy and SVN vaccination may be used as a powerful synergistic treatment for attenuation of tumor growth. In contrast, treatment with intravenous YS1646-shIDO in combination with 3342Max (MAX) in a B16F10 tumor-bearing C57BL/6 mouse model showed no significant difference in tumor growth attenuation when compared to shIDO alone (FIG. 16).

Decreased Phospho-STAT3 Levels are Observed in Tumor Macrophages Following shSTAT3 and 3342Max Treatment.

Figure 9A:
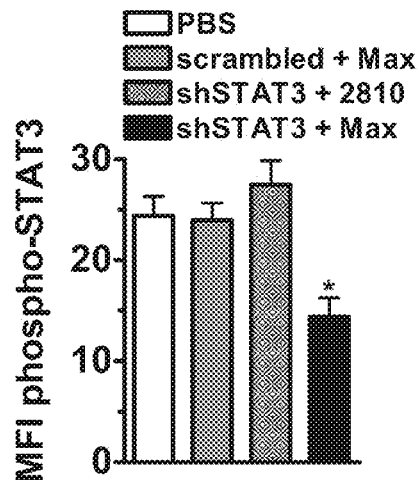
FIG. 9 shows that YS1646-shSTAT3 treatment followed by 3342Max vaccination attenuates STAT3 activation in resident tumor macrophages and enhances infiltration of T lymphocytes. B16F10 tumor-bearing mice (≥50 mm³, n=5) were injected i.v. with 10⁷ cfu of YS1646-scrambled, -shSTAT3, or PBS. Four days later, mice were then gavaged with 10⁷ cfu of MVP728-3342Max, -2810, or PBS. B16F10 tumors were excised from mice seven days after vaccination and then homogenized for staining and flow cytometry. (A) Comparison of phospho-STAT3 levels in F4/80+ macrophage for each treatment group. Phospo-STAT3 expression is presented as mean fluorescence intensity (MFI) and error bars represent standard error of the mean (SEM). (B) Frequency of CD4+ and CD8+ cells found in the tumor for each treatment group. Data represent absolute number of cells/mm³ tumor. CD4⁺ (C) and CD8⁺ (D) T cells were also analyzed for the expression of the proliferation marker Ki-67.

Flow cytometry was used to determine the levels of activated STAT3 in specific immune subsets present in the tumor following treatment with shSTAT3 and 3342Max. No significant decreases of phospho-STAT3 in CD4+, CD8+, CD11c+, or CD11b+ were found in any of the treatment groups. However, significant decreased phospho-STAT3 levels were observed in F4/80+ macrophages for the shSTAT3+3342Max treated group (FIG. 9A). No significant decreases of phospho-STAT3 were observed for the shSTAT3+2810 group. These results suggest that only the shSTAT3+3342Max treatment is able to prevent activation of STAT3 in the F4/80+ subset, likely a result of early STAT3 silencing followed by tumor control, whereas shSTAT3+2810 is unable to do so regardless of early STAT3 silencing due to uncontrolled tumor growth.

Figure 9B:
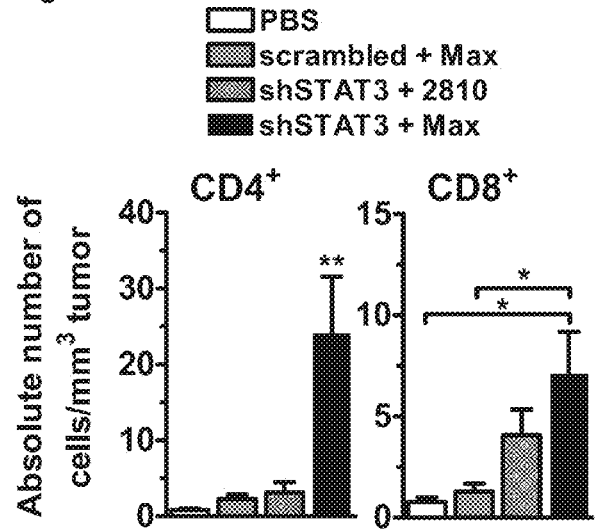
Figure 9C:
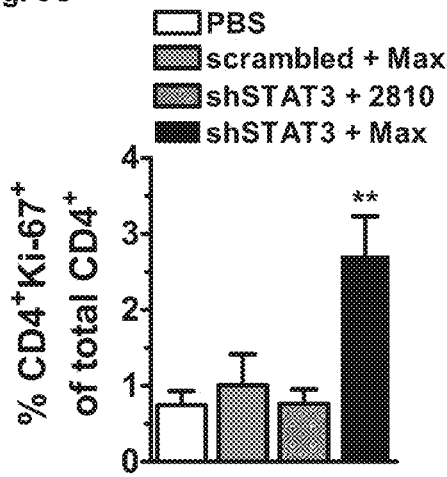
Figure 9D:
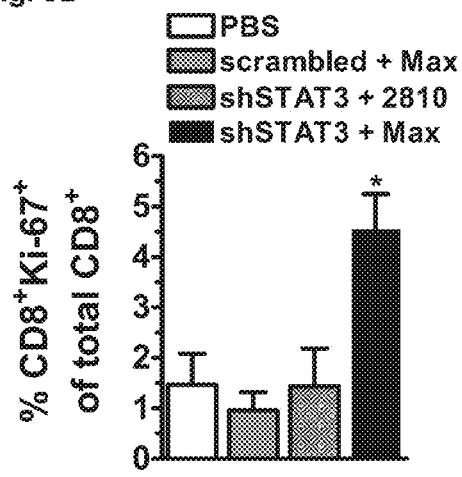

YS1646-shSTAT3 Enhances Tumor Infiltration and Proliferative Capacity of T Lymphocytes Because ablation of STAT3 increases intratumoral immune function, the frequency and functional status of intratumoral CD4+ and CD8+ T cells was examined in vaccinated mice. As shown in FIG. 9B, the percentage of B16F10 intratumoral CD4+ and CD8+ T cells was statistically greater in mice treated with shSTAT3+3342Max than in the scrambled+3342Max or PBS treatment groups.

Figure 10:
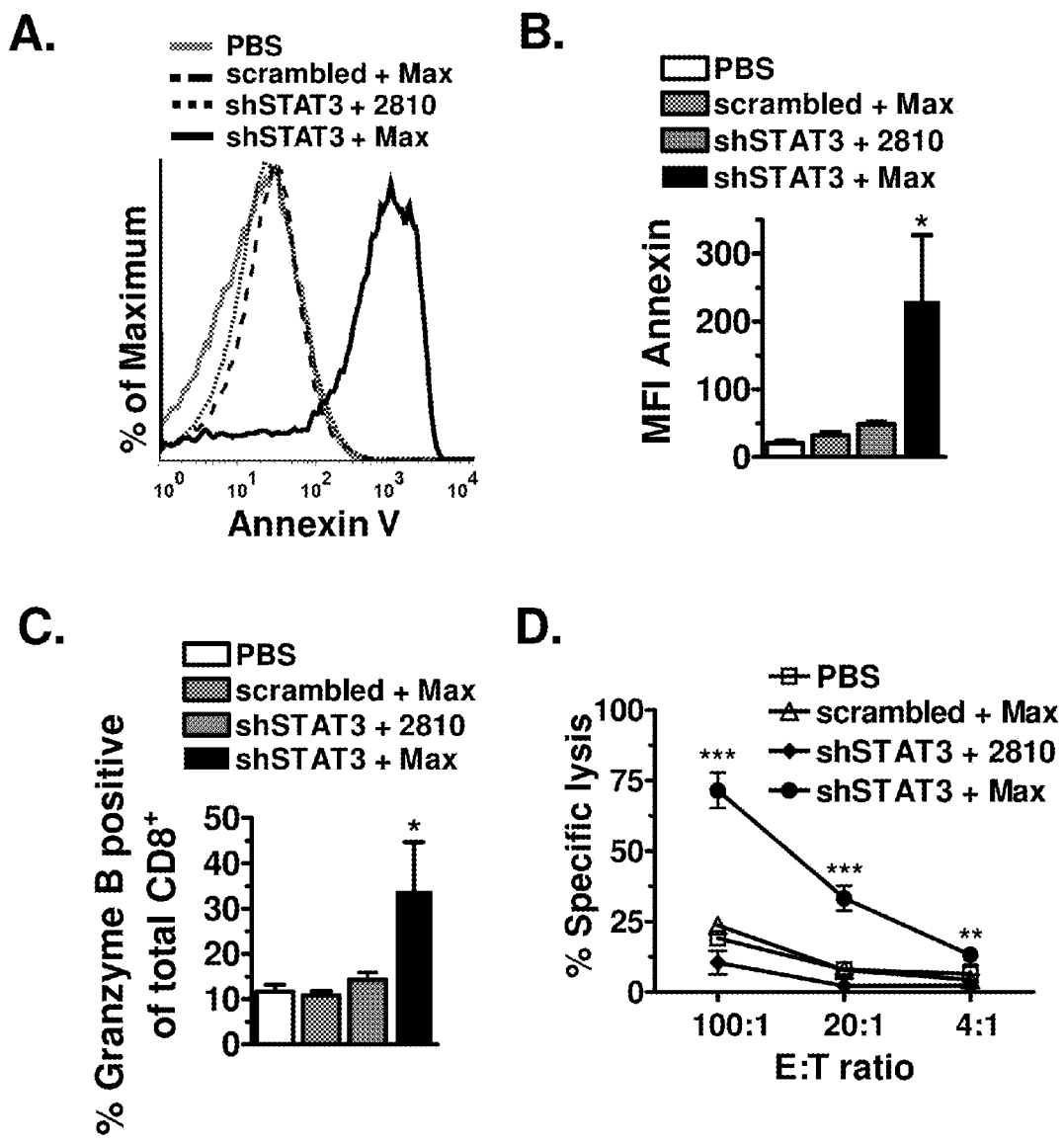
FIG. 10 shows that YS1646-shSTAT3 enhances SVN-specific cytotoxic responses. B16F10 tumor-bearing mice (n=5) received combined treatment as described in FIG. 10. (A) is a histogram representing Annexin V staining of tumor homogenates from a representative mouse from each treatment group. (B) illustrates separate tumor homogenates (n=5) from each group were stained with FITC-conjugated Annexin V and analyzed by flow cytometry. Mean fluorescence intensity (MFI) of Annexin V represents cells gated from total tumor CD45− cells. Error bars represent SEM. (C) illustrates that tumor homogenates (used in A) were stained with PE-Granzyme B and PECy7-CD8 and then analyzed by flow cytometry. Data represent mean percentages of Granzyme B⁺CD8⁺ cells out of total CD8⁺ cells. (D), shows splenocytes from mice in A (n=4) that were isolated to generate effectors for use in a chromium release assay against B16F10 targets. To generate effectors, splenocytes were incubated for 7 days with RMA-S cells initially loaded with total human SVN library (15mers, overlapping by 11). Effectors were then incubated in a 4-hour Cr⁵¹ release assay with Cr⁵¹-loaded B16F10 targets at E:T ratios of 100:1, 20:1, and 4:1, in triplicate. Percent specific lysis was calculated using the following formula: (experimental release-spontaneous release)/(maximal release-spontaneous release)×100%.

The proliferative index of these intratumoral CD4+ and CD8+ T cells was evaluated by determining Ki67 expression. Both the CD4+ and CD8+ populations expressed a higher levels of Ki67+ in the shSTAT3+3342Max group compared to control groups (FIGS. 10C and 10D). The marked proliferation suggests that the combined shRNA and vaccination treatments allow intratumoral T cells to proliferate and expand more rapidly. Thus, the increased frequency may not solely be explained by a redistribution of existing T cells from other sites.

YS1646-shSTAT3 Enhances SVN-Specific Cytotoxic Responses and Tumor Cell Apoptosis Tumor cell death was evaluated by determining the extent of apoptosis using annexin V staining of gated CD45− cells, mainly tumor cells (Byrne & Halliday 2003), from all of the treatment groups. The CD45− cells revealed significantly higher apoptotic frequencies in mice treated with shSTAT3+ 3342Max than the control groups. Data from a representative mouse is shown in FIG. 10A as a histogram and pooled data shown in FIG. 10B. The increased apoptosis of tumor cells may be explained by the cytotoxic activity of immune cells or by a shSTAT3-based mechanism to enhance apoptotic signal transduction. To determine the immune-based mechanisms, the function of the CD8+ T cell subset was investigated by evaluating granzyme B levels in B16F10 tumor-bearing mice (>50 mm3) treated with shSTAT3+ 3342Max versus groups treated with scrambled+3342Max or shSTAT3-F2810 (FIG. 10C). The proportion of CD8+ T cells expressing granzyme B in the mouse group treated with shSTAT3+3342Max was considerably higher than both control groups. These results suggested a cytotoxic mechanism of tumor growth control which was further assessed using a direct in vitro cytotoxicity assay.

SVN-Specific Cytotoxicity Contributes to Control of Established Subcutaneous B16F10 Tumors It was determined if T cells obtained from B16F10 tumor-bearing mice treated with shSTAT3+3342Max possessed functional capacity to kill survivin-expressing tumor cells in vitro by conducting a chromium release assay (FIG. 10D). Splenocytes harvested from B16F10 tumor bearing mice (n=4) treated as in FIG. 10A were stimulated in vitro with a SVN peptide library, then evaluated for in vitro cytotoxic recognition and killing of chromium-loaded B16F10 tumor targets. Mice treated with either scrambled+ 3342Max or shSTAT3+2810 alone could not effectively kill B16F10 tumor cells. In contrast, splenocytes from all mice receiving shSTAT3+3342Max treatment were effective at killing B16F10 tumor targets (0.001<p<0.01) at all effector ratios (FIG. 10D). These results suggest that the mechanism of tumor growth attenuation is by SVN-specific T cells directly killing tumor cells, but only when mice are pre-treated with shSTAT3. In addition, the combination treatment of 3342Max ($10^7$ cfu) with YS1646-shSTAT3 ($10^7$ cfu) is also effective in preventing lymphoma tumor growth as compared to 3342Max treatment alone or at lower concentrations of each, which indicates that this combination treatment may have broad application to various tumor types (FIG. 11).

Effect of Systemic Delivery of shSTAT3 or shIDO1 on Tumor Growth

YS1646 carrying the shSTAT3#60 plasmid (YS1646-shSTAT3) generated as described above was used to test whether systemic delivery of *Salmonella* by an i.v. route could silence STAT3 expression in situ in the tumor. Mice bearing subcutaneous B16F10 tumors (>50 mm3) were injected i.v. twice with $10^7$ cfu of YS1646-shSTAT3, -scrambled, or PBS (4 days apart). Post-treatment, no significant attenuation of tumor growth was observed for mice treated with YS1646-shSTAT3 alone compared to control groups (data not shown). Tumors were then isolated, homogenized, and total RNA was extracted for quantitative PCR. Significant silencing of STAT3 was observed three days after YS1646-shSTAT3 administration compared to mice that were administered YS1646-scrambled or PBS (FIG. 8B). STAT3 silencing continued to increase on day 7 in the shSTAT3 group. This result implicates that direct knockdown of STAT3 RNA is important to the therapeutic activity of the shSTAT3-Max treatment. On day 10, STAT3 silencing moderated, but mRNA levels were still lower than the control groups (FIG. 8B).

Figure 13:
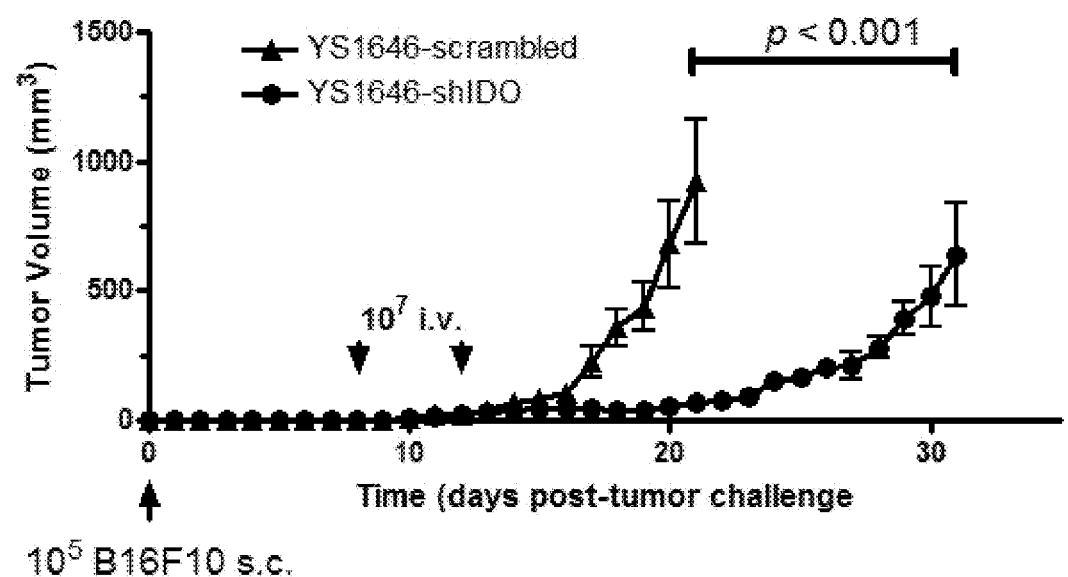
FIG. 13 is a graph illustrating the effect of intravenous injection of attenuated $Salmonella$ strain YS1646 that carries shIDO1-9 (YS1646-shIDO1) in a B16F10 tumor-bearing C57BL/6 mouse model where tumors were treated when diameters were ≥5 mm. Tumor volume was assessed up to 31 days post-tumor challenge in mice injected with YS1646-shIDO1 or YS1646-scramble control.
Figure 14:
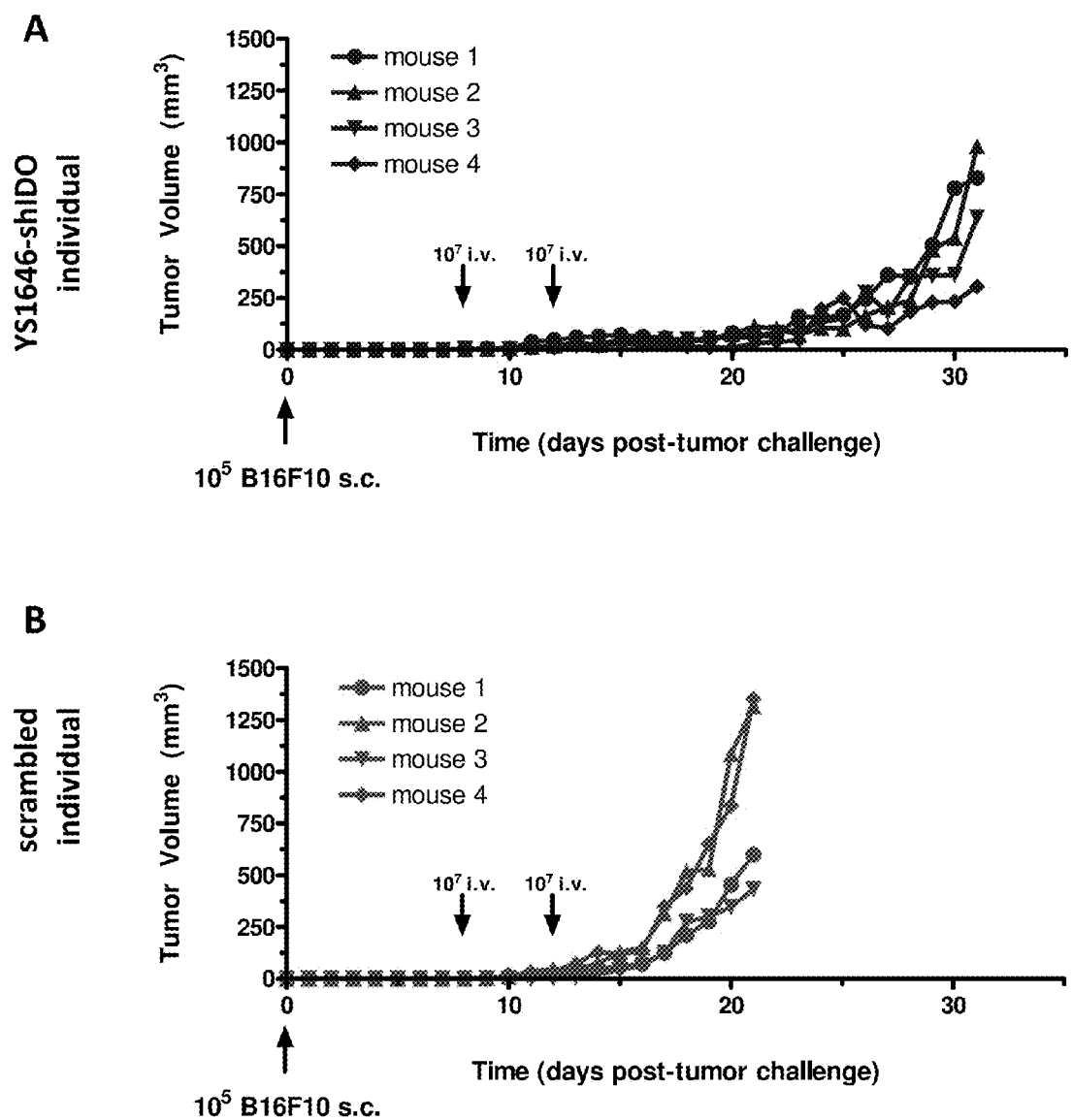
FIG. 14 is a pair of graphs representing individual mice from FIG. 13 and the effect of intravenous injection of (A) YS1646-shIDO1 or (B) YS1646-scrambled control in the B16F10 tumor-bearing C57BL/6 mice (n=4). Tumor volume was assessed up to 31 days post-tumor challenge in mice injected with YS1646-shIDO1 or YS1646-scramble control.
Figure 17:
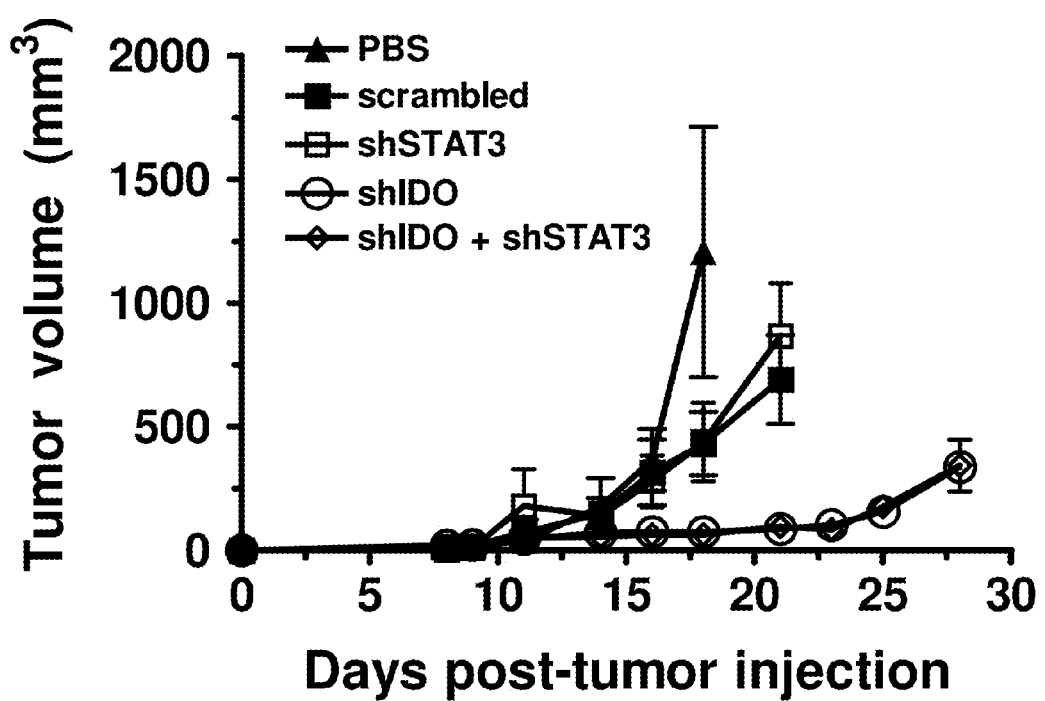
FIG. 17 is a graph illustrating the effect of intravenous injections of YS1646-shSTAT3, YS1646-shIDO1 or a combination of YS1646-shSTAT3 and YS1646-shIDO1 in a B16F10 tumor-bearing C57BL/6 mouse model. The combined treatment showed no significant difference in tumor growth attenuation when compared to shIDO1 alone.

YS1646-shSTAT3 and YS1646 carrying the shIDO-9 plasmid (YS1646-shIDO) generated as described above were then used to determine whether silencing of STAT3 and/or shIDO effects tumor development or growth of B16F10 tumors. Briefly, B16F10 tumors in C57BL/6 mice were allowed to grow to approximately 25-50 mm³ and then YS1646-shSTAT3, YS1646-shIDO or a combination thereof were administered by intravenous injection (FIGS. 13, 14, and 17). Controls used were a *Salmonella* delivery vehicle containing a plasmid with a scrambled version of the shRNA plasmid and/or a PBS control group. As shown in FIGS. 13, 14 and 17, shIDO treatment showed a significant suppression of B16F10 tumor growth. shSTAT3 treatment alone was far less effective than shIDO alone, and showed moderate to no suppression of B16F10 tumor growth (FIG. 17). Treatment with both shIDO and shSTAT3 did not suppress tumor growth any greater than that achieved with shIDO treatment alone (FIG. 17). These results confirmed that YS1646-shIDO succeeded in specifically suppressing tumor growth when used as a single agent. ShIDO alone was shown to be more effective than a scrambled sequence in a Pan02 pancreatic tumor model (FIG. 15).

Example 3

Tumor-Targeted Delivery of 100-Specific shRNA

Generation of shIDO-ST. shRNA constructs against IDO (FIG. 21) (Sigma, cat#SHCLNG-NM 008324) were tested for silencing by co-transfection of HEK293 cells with an IDO-expressing plasmid at a ratio of 5:1 (2.5 μg/0.5 μg) using Lipofectamine 2000 (Invitrogen). Cells were maintained in DMEM with 10% FBS for 48 hrs. Lysates of transfected cells were generated using a RIPA lysis buffer and equal amounts were loaded for western blot. IDO protein was detected using the monoclonal mouse antibody clone 10.1 (Millipore). β-tubulin was used as a loading control using the monoclonal mouse antibody clone D66 (Sigma, cat. no. T0198). The pLKO.1-puro vector containing the 21-mer shRNA sense sequence CGTCTCTCTAT-TGGTGGAAAT (SEQ ID NO:24) (ID#TRCN0000066909) exhibited >75% IDO knockdown and was selected for transformation into VNP20009 (also known as YS1646, ATCC#202165). Scrambled shRNA (shScr) (Sigma) and IDO shRNA (shIDO) plasmids were electroporated into VNP20009 with a BTX600 electroporator (BTX) at 2.5 kV, 186 ohms. Clones were selected on LB-ampicillin plates, cultured by shaking at 37° C. in LB-O-ampicillin media, and confirmed for the presence of the correct plasmid by restriction digest and retesting by co-transfection and western blot of IDO.

Animals and cell lines. C57BL/6, IDO-KO, and Rag1-KO mice (Jackson, 6-8 weeks) were obtained from breeding colonies housed at the City of Hope (COH) Animal Research Center (Duarte, Calif.). Animals were handled according to Institutional Animal Care and Use Committee guidelines under IACUC protocol #08048. The B16F10 murine melanoma line was a gift from Drs. Hua Yu and Marcin Kortylewski (COH) and were maintained in DMEM containing 10% FBS. The H35 (CD8) and GK1.5 (CD4) hybridomas were purchased from ATCC and the RB6-8C5 hybridoma (originally produced by Robert L. Coffman) used to generate Gr-1 antibody for depletion experiments was a gift from Dr. Hans Schreiber (University of Chicago). All hybridomas were maintained in RPMI containing 10% FBS.

Tumor challenge and therapy. For tumor challenge, 2.5× $10^5$ B16F10 cells were injected subcutaneously into the upper left abdomen of C57BL/6 mice. Tumor growth was monitored daily or every other day using a sliding millimeter caliper. Treatment included either phosphate buffered saline (PBS) or 2.5×$10^6$ cfu of shIDO- or shScr-ST injected intravenously twice, 4 days apart, into mice when tumor volumes reached ≥50 mm³ (7-8 mm in diameter). Preparation and treatment of B16F10 tumor-bearing (≥50 mm³) mice with D-1MT, with or without cyclophosphamide, was done as previously described (Hou et al. 2007). Briefly, the D-1MT+ cyclophosphamide (CY) groups were treated with D-1MT daily (5 mg/day by gavage) and given one dose of cyclophosphamide (150 mg/kg i.p.) 4 days after starting D-1MT treatment when tumors reached ≥50 mm³. Mice receiving D-1MT alone were given 20 mg/day by gavage. Numbers of mice per group are indicated in figure legends (FIG. 23D) and experiments were generally repeated more than twice to confirm reproducibility of results.

Quantitative PCR for detection of IDO levels. Mice bearing B16F10 tumors (≥50 mm³) were i.v. injected with 2.5×$10^6$ cfu of shIDO-ST or shScr-ST. 72 hours later, mice were sacrificed and RNA was extracted from tumor homogenates for generation of single stranded cDNA (Fermentas). To quantitate IDO levels, SYBR®-Green qPCR analysis (BD Biosciences) using primers specific for IDO was carried out using GAPDH for normalization. Primers are listed below.

IDO primers:
Forward:
(SEQ ID NO: 25)
5'-GGAACCGAGGGGATGACGATGTTC-3'

Reverse:
(SEQ ID NO: 26)
5'-AGACTGGTAGCTATGTCGTGCAGTGC-3'

GAPDH primers:
Forward:
(SEQ ID NO: 27)
5'-CAAGGTCATCCATGACAACTTTG-3'

Reverse:
(SEQ ID NO: 28)
5'-GTCCACCACCCTGTTGCT GTAG-3'

Immunofluorescence staining. For detection of intracellular recombinant ST infection, B16F10 cells seeded on coverslips were infected for 2 hours at an MOI of 10 with shIDO-ST. Cells were then incubated overnight in DMEM-10 containing 10 µg/mL gentamicin. Cells were fixed/permeabilized with 1:1 acetone:methanol and stained with conjugated FITC-LPS antibody (Santa Cruz Biotech) overnight at 4° C. followed by DAPI staining. Cells were imaged at 100× magnification on an Axiovert 200 using live imaging software (Axiovision). Image shown is representative of cells observed within multiple fields.

Figure 22:
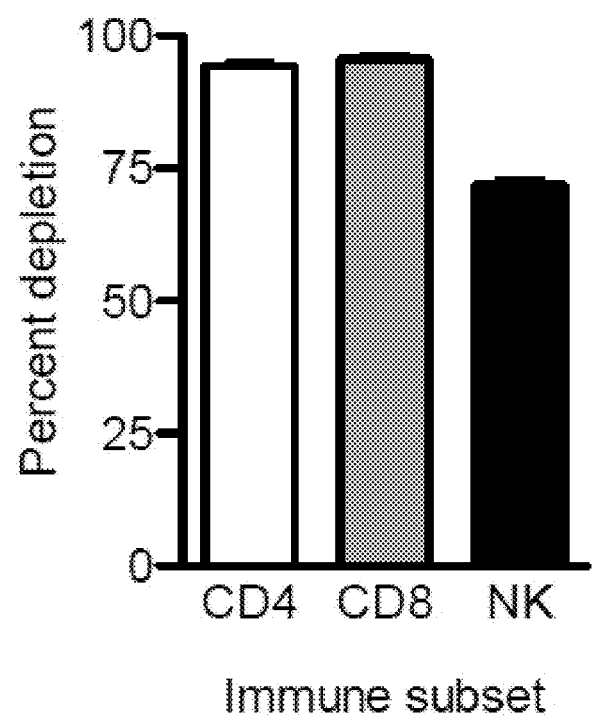
FIG. 22 shows depletion of CD4+, CD8+, and NK immune subsets. B16F10 tumor-bearing mice (n=3) were depleted of CD4+, CD8+, and NK cell subsets by i.p. injection of depleting antibody specific for each immune population. Mice were not treated during this time. Data represents cell populations in blood 24 hours after first i.p. injection

Depletion of immune subpopulations. $CD8^+$, $CD4^+$, and NK cell depletions were done through continuous i.p. injections of depleting antibody clones H35 (CD8), GK1.5 (CD4) or anti-asialo GM1 (NK; Wako) at 200 µg/injection. Selective depletion of PMN was achieved by continuous i.p. injections of Gr-1 depleting antibody (30 µg/injection). Antibody was administered 2 days after first treatment with ST and then given every 3 days after as maintenance doses. Depletion of individual immune subpopulations (>95%) was confirmed in blood by flow cytometry on a FACS-Canto (Becton Dickinson) and analyzed using FlowJo™ software (TreeStar) (FIG. 22).

Flow cytometry. Conjugated monoclonal antibodies (mAbs) directed to PECy7-CD8, PE-Gr-1, PECy7-Ly6G, FITC-CD11b, APC-CD11c, PE-B220, and PerCP-CD45 were purchased from BD Pharmingen and mAb to APC-Cy7-CD4, APC-F4/80, and FITC Annexin V were purchased from eBioscience. Annexin V staining was performed following the manufacturer's protocol (eBioscience). For reactive oxygen species (ROS) analysis, samples were incubated with CD45, Ly6G and 2',7'-dichlorofluorescin diacetate (DCFH-DA) (Sigma, cat. no. D6883) for 20 minutes at 37° C. in a 5% CO2 incubator. All samples were run on a FACS-Canto and analyzed using FlowJo™ software.

Statistical analysis. The Student's t test was used to calculate two-tailed P value to estimate statistical significance of differences between two treatment groups in the whole study. One-way ANOVA plus Bonferroni post-test were applied to assess statistical significance of differences between multiple treatment groups. Statistical test and significant P values were indicated in figures and/or figure legends. *$P<0.001$, $P<0.01$, *$P<0.05$. Data were analyzed using the Graphpad Prism Software v4.03 (Graphpad). All experiments were typically performed at least twice, and all data are presented as mean+standard error of the mean (SEM).

Results

Figure 12:
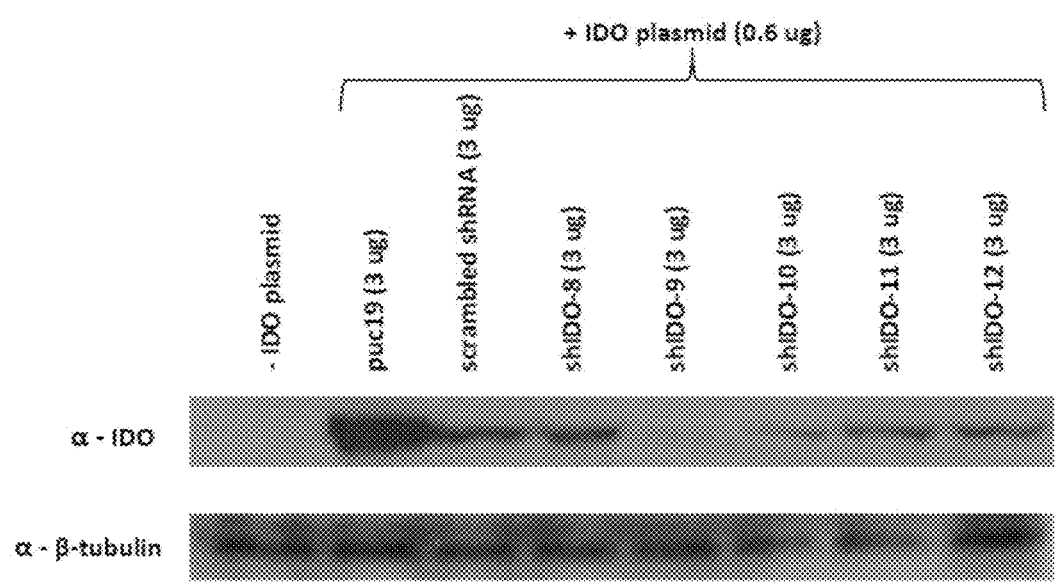
FIG. 12 is a Western blot of IDO1 protein expression from HEK293 lysates after co-transfection of an IDO expression plasmid (Origene) with an shRNA construct (shIDO1-8, shIDO1-9, shIDO1-10, shIDO1-11, or shIDO1-12) at a ratio of 5:1 shIDO:IDO expression plasmid. The most optimal silencing was observed by IDO1-9 (>70%). Lysates were generated 48 hrs post-transfection and equal amounts were loaded for western blot. β-tubulin is used as a loading control. IDO has a molecular weight of ~42 kD.

Tumor-derived IDO can be inactivated by using a unique combination of IDO-specific shRNA plasmids delivered by the clinically tested ST strain VNP20009 (Toso et al. 2002; Manuel et al.) (shIDO-ST). In addition to tumor colonization, ST also recruits PMNs almost exclusively (Kirby et al. 2002), a characteristic of ST that has not yet been extensively exploited for cancer therapy. Simultaneous silencing of IDO and colonization by ST may be required to generate a focused cytotoxic PMN response within the immunosuppressive microenvironment of the tumor. To that end, several shRNA constructs were tested (FIG. 21) for their ability to silence IDO expressed from a separate plasmid. Using western blot analysis, a significant reduction of IDO expression was observed from the shIDO#9 construct (FIG. 23a), with a >75% knockdown compared to scrambled shRNA (shScr) control (FIG. 12).

Figure 24:
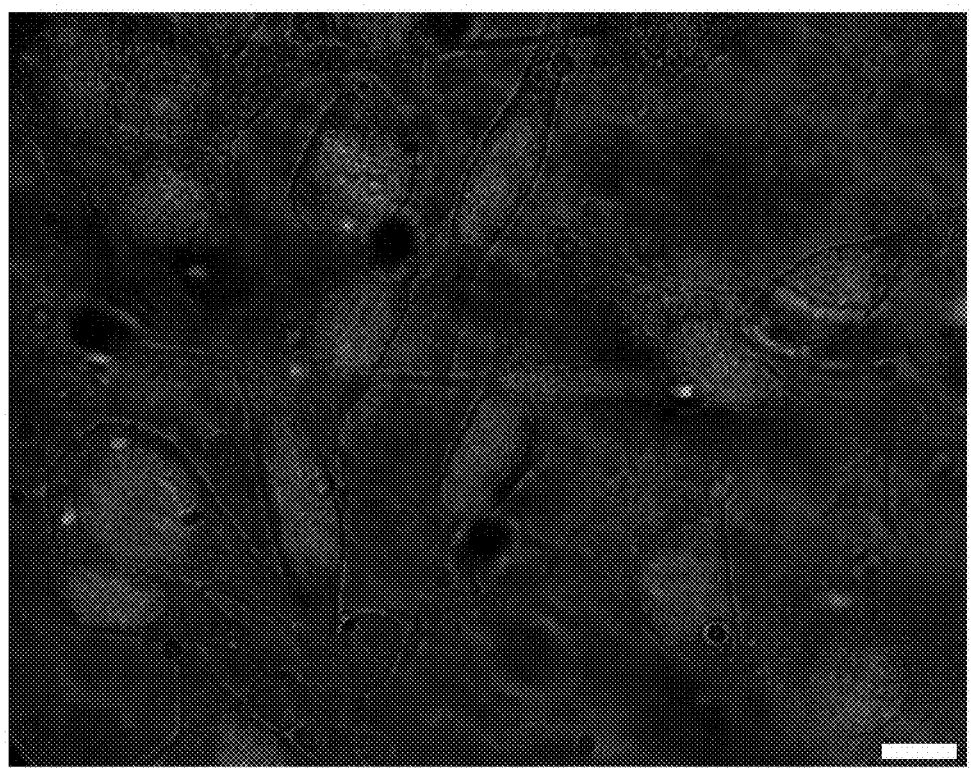
FIG. 24 shows a full representation of representative field in detection of shIDO-ST infected B16F10 culture cells. B16F10 cells cultured on coverslips were infected with shIDO-ST for 2 hrs with late-log phase bacteria at an MOI of 10. Coverslips were then washed and incubated for an additional 16 hrs with gentamicin before fixing/permeablizing with 1:1 acetone:methanol. Salmonella are labeled using a FITC LPS-specific antibody (green) and the B16F10 cell nuclei are stained with DAPI (blue). Magnification is at 100×. Scale bar, 5 µm.
Figure 25:
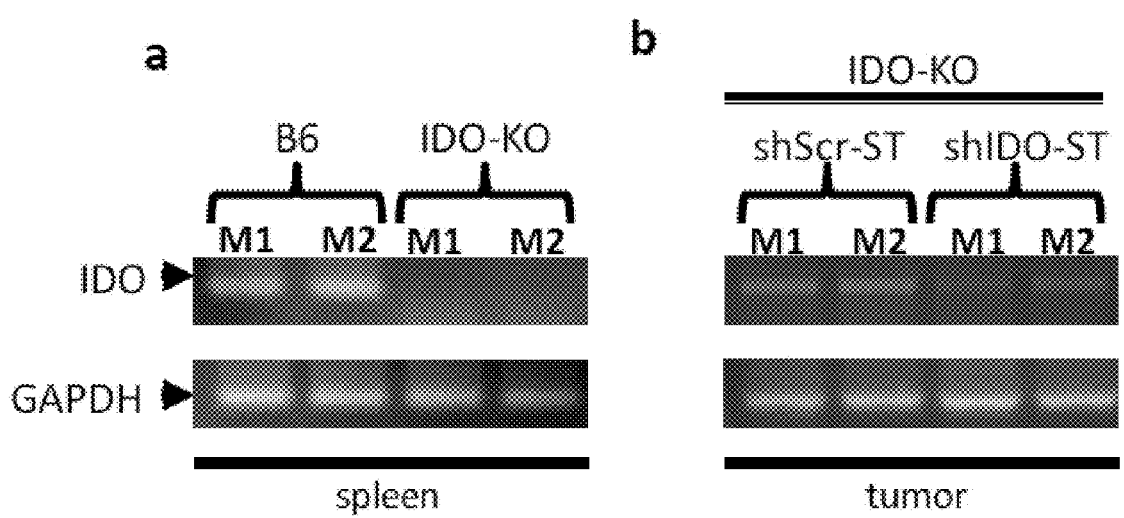
FIG. 25 shows measuring of IDO expression in C57BL6 mice, IDO-KO mice and in B16F10 cells growing in IDO-KO mice. (a) spleens from B6 or IDO-KO mice (n=2) were examined for presence of IDO by PCR. GAPDH is used as a normalizer to confirm equal initial cDNA amounts. (b) B16F10 tumor-bearing IDO-KO mice (n=2) were treated twice i.v., 4 days apart, with shScr-ST or shIDO-ST. Tumors were processed 1 d after the 2nd injection to produce cDNA for detection of IDO by PCR. In both treated groups, IDO expression is detected in B16F10 cells, with slightly less expression in shIDO-ST treated mice. M=mouse

The shIDO plasmid was transformed into VNP20009 for further analyses. Assessing the infectability of the newly generated recombinant shIDO-ST, it was determined that >70% of cultured B16F10 melanoma cells were infected with shIDO-ST by fluorescence microscopy (FIG. 23b, see FIG. 24 for full image) following incubation with late-log phase bacteria at an MOI of 10. These data suggest that transformation of VNP20009 with shIDO plasmid did not impede infectivity. To measure tumor-specific IDO silencing by shIDO-ST in vivo, mice lacking cellular IDO (IDO-KO) (FIG. 25a) were used to confirm that IDO silencing was occurring in IDO-expressing B16F10 cells (FIG. 25b). Quantitative analyses of tumor homogenates using qPCR revealed a significant reduction in IDO mRNA from shIDO-ST-treated mice compared to shScr-ST-treated mice (FIG. 23c). These data confirm that IDO is expressed in B16F10 cells growing subcutaneously in mice and that expression is silenced following treatment with shIDO-ST.

Figure 26:
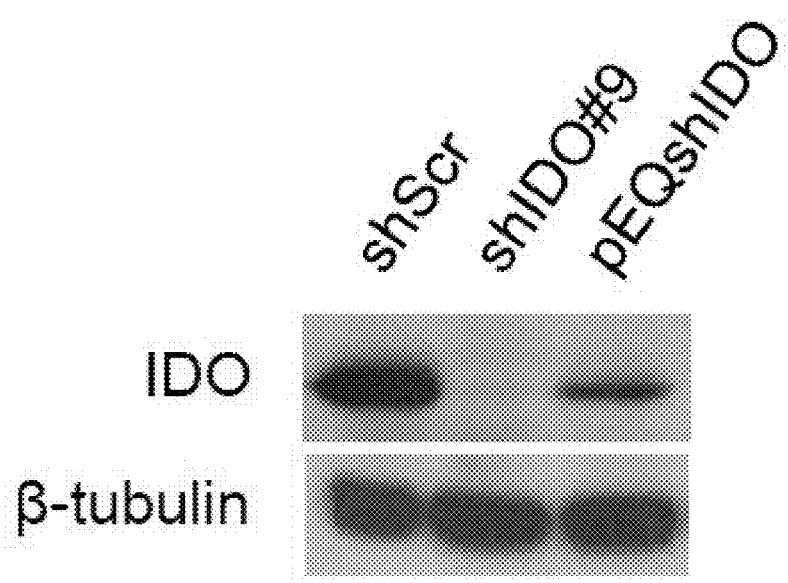
FIG. 26 shows measuring of IDO expression from a co-transfection of EK293 cells with shRNA and IDO-expressing plasmids. An alternate shRNA plasmid specific to IDO, pEQshIDO15, was used for confirmation of the IDO-specific effect by shIDO#9. Shown is a co-transfection assay using a 5:1 ratio of shRNA plasmid to IDO-expressing plasmid. Equal numbers of cells were transfected and, 48 hours later, equal amounts of lysates generated were loaded for western blot detection of IDO protein. β-tubulin is used as a loading control.

To determine the antitumor effects of IDO silencing by shIDO-ST, longitudinal measurements of subcutaneous B16F10 tumor growth were carried out in mice treated with shIDO-ST. It was found that shIDO-ST was successful in attenuating B16F10 growth (FIG. 23d) and extending survival of tumor-bearing mice compared to groups treated with a shScr-ST control. ShIDO-ST was also significantly better in controlling growth of B16F10 tumors compared to mice treated with the previously described regimen of the IDO inhibitor D-1-methyl tryptophan (D-1MT) combined with cyclophosphamide (CY) (Hou et al. 2007) ($P<0.05$). To rule out possible off-target effects by shIDO-ST, a published alternate shRNA sequence against IDO (Zheng et al. 2006) was also used, which exhibits ~50% less activity than that of shIDO#9 (FIG. 26), and found that recombinant VNP20009 carrying the alternate shRNA (pEQshIDO-ST) could attenuate tumor growth at the same level as shIDO-ST (FIG. 23d). Thus, the strategy described herein maintains its efficiency even at 50% of its maximal IDO silencing potential. These results highlight the superior efficacy of shIDO-ST over chemical IDO inhibitors in controlling tumor growth and extending survival.

Many small molecule inhibitors, such as D-1MT, are limited because they only target the IDO activity of host APCs and are therefore ineffective against IDO expressing tumor cells (Hou et al. 2007; Kumar et al. 2008). Therefore, it was determined whether shIDO-ST, which silences tumor IDO (FIG. 23c), could control tumor growth in the absence of host IDO. Because B16F10 are syngeneic to the C57BL/6 background, tumors can be grown in Ido1−/− mice to allow determination of the relative importance of host IDO and tumor IDO in blocking antitumor responses. Surprisingly, it was found that shIDO-ST could significantly control B16F10 growth in mice deficient of IDO compared to shScr-ST- and D-1MT-treated groups (FIG. 23e), confirming that the mode of action of shIDO-ST is mediated primarily through the silencing of tumor-derived IDO. These results also demonstrate that IDO expression by B16F10 is sufficient to block antitumor immune responses regardless of host IDO.

Previously studied IDO inhibition strategies, like D-1MT combined with CY or gemcitabine, show dependence on T-cells for efficacy (Hou et al. 2007; Zheng et al. 2006). In general, T-cell-dependent immunotherapies suffer from the low frequency of T-cells in the tumor, which are tolerized and thus limited in proliferative capacity and antitumor function. To determine whether shIDO-ST therapy was dependent on adaptive T-cell immunity, the ability of shIDO-ST to attenuate tumor growth in C57BL/6 or IDO-KO mice depleted of specific immune subsets was tested (FIG. 22). In contrast to IDO inhibitors, it was observed that significant tumor growth control by shIDO-ST was maintained in mice depleted of CD8+, CD4+, or NK cells (FIGS. 23f-g). Further evaluation of ShIDO-ST treatment in tumor-bearing Rag1-KO mice, which are devoid of T- and B-cells, revealed that shIDO-ST still remains active in controlling tumor growth (FIG. 23h). Thus, shIDO-ST is advantageous over current chemical IDO inhibitors as it has the potential to function in both immunocompetent and immunocompromised cancer patients. Furthermore, the data represent an alternate mechanism of tumor evasion by IDO that is independent of adaptive T-cell immunity.

Figure 28:
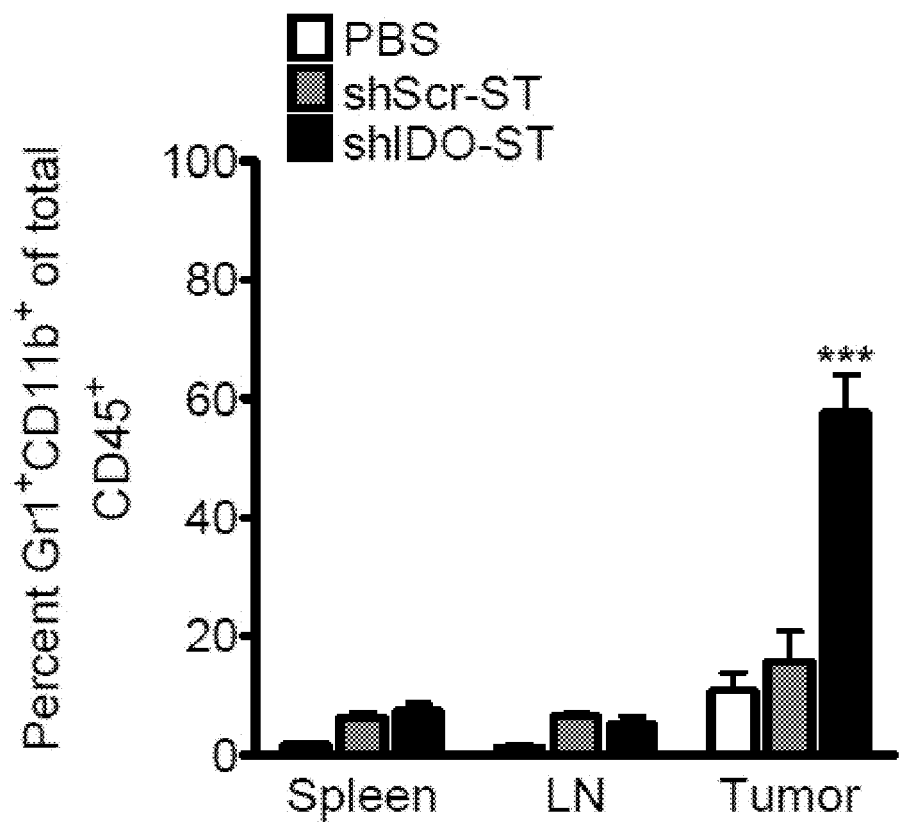
FIG. 28 illustrates the frequency of Gr1+CD11b+ cells in organs of tumor-bearing mice receiving PBS, shScr-ST, or shIDO-ST treatment. B16F10 tumor-bearing mice (n=4) were treated when tumors reached ≥50 mm³. Tumor homogenates were stained with antibodies against Gr1 and CD11b and then analyzed by flow cytometry. Error bars represent SEM. ***P<0.001 by one-way ANOVA test.

Further investigation of immune subsets in shIDO-ST-treated mice revealed a significant increase of intratumoral Gr1+CD11b$^+$ cells (FIG. 27a), which was not observed in spleen or tumor-draining lymph nodes. (FIG. 28). Because the Gr-1 antibody recognizes both Ly6G and Ly6C subpopulations (Fleming et al. 1993), the increased frequency of Gr1$^+$CD11b$^+$ cells represents a range of possibilities including myeloid derived suppressor cells, PMN, dendritic cells, or other subsets of monocytes. Since ST colonization of spleen has been shown to significantly increase splenic PMN frequency (Kirby et al. 2002), tumor colonization by shIDO-ST may attract PMN into the tumor that account for a large percentage of the Gr1+CD11b+ cells. Using an antibody against the PMN-specific marker Ly6G, it was determined that >90% of the Gr1$^+$CD11b$^+$ population was Ly6G positive (FIG. 27b), implicating PMN as an important immune subset mediating tumor growth control. Unlike previous studies with D-1MT and other chemical IDO inhibitors, a specific immune population involved in the antitumor effects of the treatment has been defined, which can be used as a criterion for administering and predicting efficacy of shIDO-ST therapy.

Figure 29:
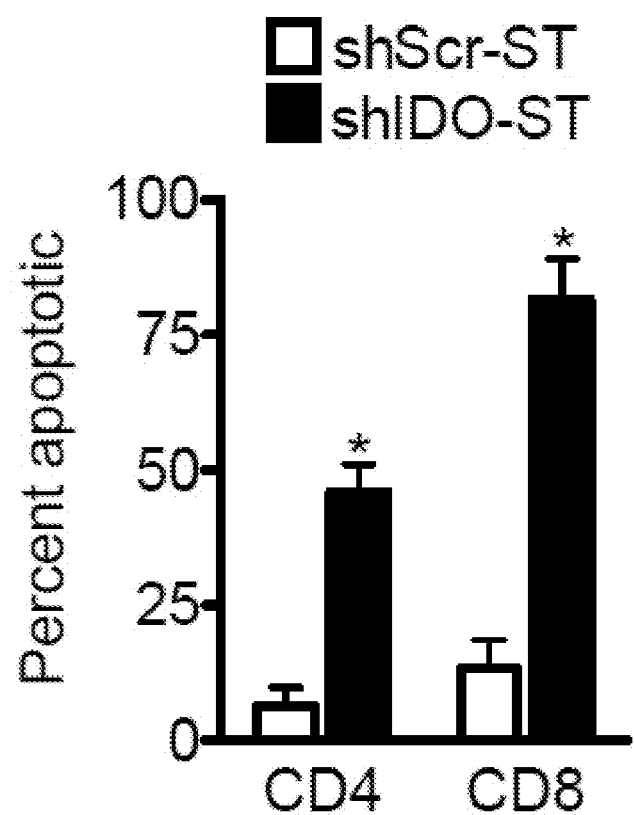
FIG. 29 shows apoptotic CD45+ subsets in tumors of shIDO-ST treated mice includes CD4+ and CD8+ cells. Tumor homogenates from tumor bearing mice of shScr-ST and shIDO-ST treated mice were stained with Annexin V and CD4 or CD8 antibody and then analyzed by flow cytometry. Percent apoptotic represents CD4+ or CD8+ T cells that are Annexin V positive out of total CD4+ or CD8+ T cells, respectively. *P<0.05 by Student's t test.

Recruitment of PMN into tumors by shIDO-ST was used to determine if complete intratumoral cell death was occurring, indicative of both tumor cells and the vascularized stroma being destroyed, which significantly lowers the potential for tumor regrowth. Therefore, the extent of intratumoral cellular apoptosis was measured in nontumor (CD45$^+$) and tumor (CD45$^-$) cell subsets through Annexin V staining. In line with PMN-mediated tumor killing, a significant amount of Annexin V staining of both CD45$^+$ and CD45$^-$ populations was observed in shIDO-ST-treated mice, suggesting total intratumoral apoptosis (FIG. 27c-d). Further analysis revealed that both CD8$^+$ and CD4$^+$ populations, found at low frequencies in the tumor (FIG. 27a), were significantly more Annexin V positive (FIG. 29) compared to shScr-ST-treated mice, independently confirming the basis for the minimal contribution of adaptive immunity to the function of shIDO-ST. Altogether, these results demonstrate that silencing IDO in the tumor by shIDO-ST leads to increased recruitment of PMN and causes total intratumoral cell death. This data is the first to implicate IDO in regulating PMN activity in vivo and presents a novel strategy to focus the cancer-killing properties of PMN using tumor-colonizing Salmonella.

Figure 30:
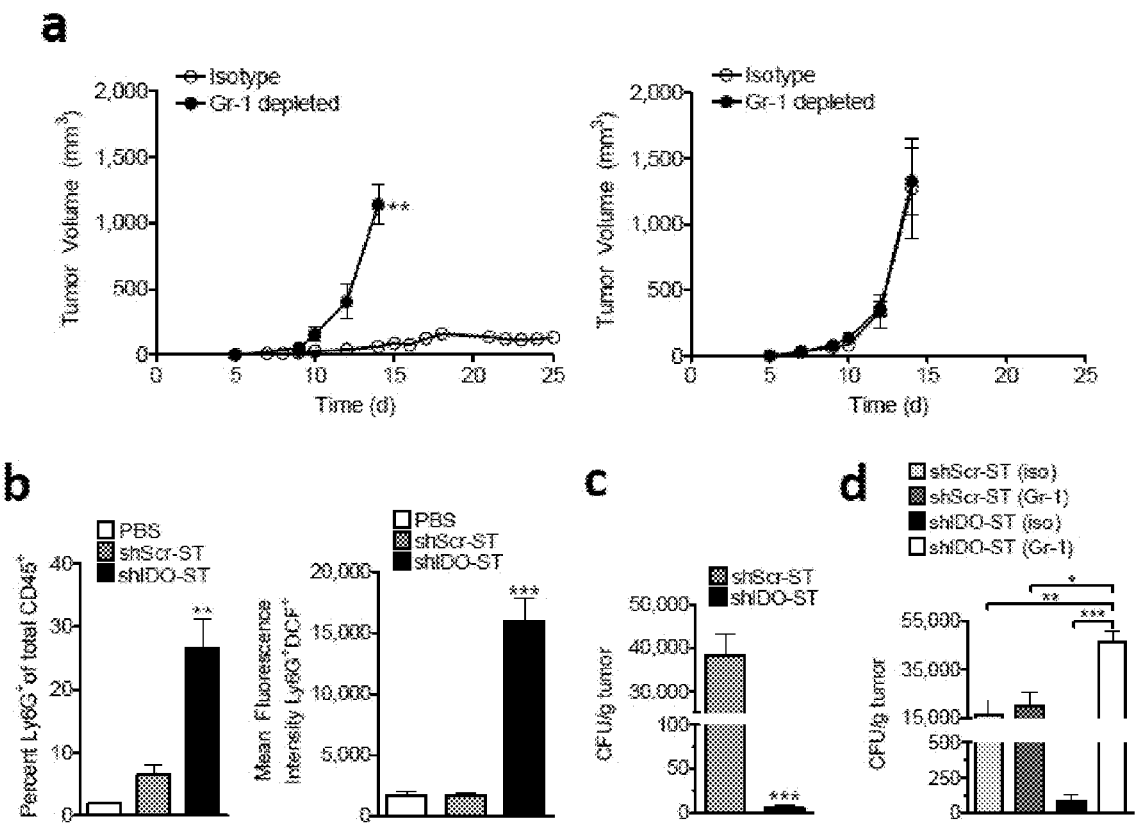
FIG. 30 illustrates that treatment with shIDO-ST augments intratumoral PMN activation, which is required for antitumor immunity and bacterial clearance. (a) shows that depletion of PMN using Gr-1 depleting antibody results in loss of tumor growth control by shIDO-ST. B16F10 tumor-bearing B6 mice were treated with either shIDO-ST (left panel) or shScr-ST (right panel) when tumors reached ≥50 mm³. Two days following the first ST injection, mice were depleted of PMN by i.p injection of Gr-1 depleting antibody with maintenance injections every 3 days. Tumor volume was measured longitudinally. P<0.01 by Student's t test. (b) shows that increased intratumoral PMN frequency in mice treated with shIDO-ST exhibit increased ROS activity. Two days after treatment with PBS, shScr-ST, or shIDO-ST, single cell suspensions of tumors (n=4) were prepared and incubated with anti-CD45, anti-Ly6G, and DCFH-DA. Samples were analyzed by FACS. The left panel represents percentage of $Ly6G^+$ cells present out of total $CD45^+$ cells. Right panel represents mean fluorescence intensity (MFI) of $Ly6G^+DCF^+$ cells present in total $CD45^+$ cells. P<0.01, ***P<0.001 by one-way ANOVA test. (c) Clearance of shIDO-ST 48 hrs following treatment in tumor-bearing mice. Tumor homogenates in (b) were lysed and plated onto bacterial LB-ampicillin plates. Colonies per gram tumor tissue (CFU/g tumor) were calculated 24 hrs after incubating plates at 37° C. (d) shows that Gr-1 depletion of PMN prevents clearance of shIDO-ST in tumor. C57BL/6 mice (n=4) bearing B16F10 tumors were treated as in (a). Two days after treatment, mice were sacrificed and tumor homogenates were lysed and plated onto bacterial LB-ampicillin plates. *P<0.05, P<0.01, *P<0.001 by Student's t test.

To determine if PMNs were ultimately required for tumor growth control, PMN depletion studies were performed in tumor-bearing mice receiving shIDO-ST treatment. As shown in FIG. 30a (left panel), PMN depletion resulted in the loss of tumor control by shIDO-ST compared to mice given control isotype antibody. The complete loss of shIDO-ST-mediated tumor control resulting from Gr-1 depletion confirms that PMN are the effectors of tumor control and that IDO silencing or tumor colonization by shIDO-ST are insufficient to cause tumor regression. In mice treated with shScr-ST (FIG. 30a, right panel), no significant difference in tumor growth kinetics was seen between Gr-1 or control isotype depleted groups supporting previous observations that shScr-ST does not recruit PMN to the tumor (FIG. 27a) and therefore does not control tumor growth to any measurable extent.

Figure 31:
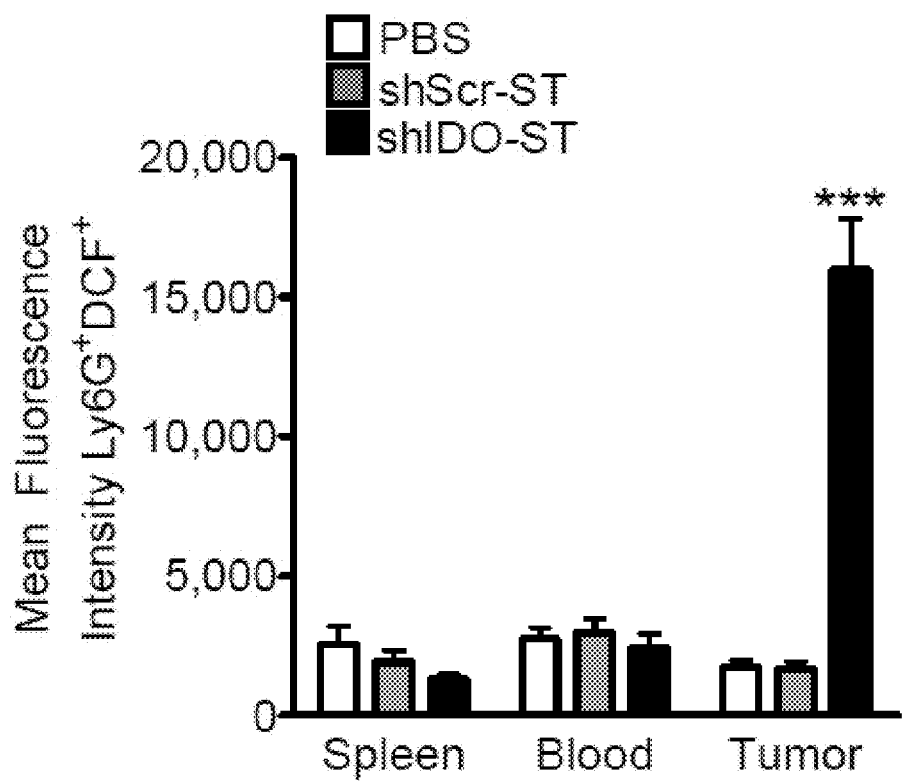
FIG. 31 illustrates neutrophils exhibiting enhanced ROS production are exclusively found in tumors of mice treated with shIDO-ST. Blood and single-cell suspensions of tumor and spleen from tumor-bearing mice treated with PBS, shScr-ST, or shIDO-ST were prepared 48 hrs following treatment. Samples were stained with Ly6G antibody and the membrane-permeable, non-fluorescent substrate 2',7'-dichlorofluorescin diacetate (DCFH-DA). DCFH-DA is converted to the fluorescent form DCF by reactive oxygen species (ROS), which is detectable by flow cytometry. Shown is the MFI of Ly6G+DCF+ cells from total CD45+ cells.

Although it was evident that PMN were required for the therapeutic efficacy of shIDO-ST, the mechanism by which PMNs caused regression of B16F10 tumor was still unclear. Therefore, studies were performed to measure levels of reactive oxygen species (ROS), a major product generated by PMN during microbial infection, which is also a potent mediator of tumor killing (Wang & Yi 2008; Zivkovic 2005). To quantify PMN ROS production, the non-fluorescent probe 2',7'-dichlorofluorescein diacetate (DCFH-DA) was used, which diffuses into cells and can be converted by ROS to the highly fluorescent 2',7'-dichlorofluorescein (DCF) detectable by flow cytometry (Rothe & Valet 1990). Tumor-bearing mice receiving either PBS, shScr-ST or shIDO-ST therapies were sacrificed 48 hours after treatment and intratumoral PMN were assessed for ROS activity. Within this time, significantly higher intratumoral PMN frequencies were observed in mice treated with shIDO-ST compared to control-treated groups (FIG. 30b, left panel). Furthermore, when PMN were analyzed for ROS activity using the DCFH-DA fluorescence assay, it was found that only intratumoral PMN from shIDO-ST-treated mice exhibited significant increases in fluorescence compared to control groups (FIG. 30b, right panel). Enhanced ROS production was not seen in PMN isolated from blood or spleen of tumor-bearing mice treated with shIDO-ST (FIG. 31). These results confirm that shIDO-ST treatment generates ROS-producing PMN exclusively in the tumor.

Increased apoptosis of tumor cells is likely an indirect effect of activated PMN responding to clear tumor-colonizing ST. To determine whether shIDO-ST persistence is affected by the increased presence of PMN, ST was enumerated in the tumors of mice receiving either shScr-ST or shIDO-ST. In mice receiving shScr-ST, considerable numbers of bacteria in tumor were found 48 hrs post-treatment while, surprisingly, significantly fewer bacteria were found in mice receiving shIDO-ST (FIG. 30c). Then, PMN were then depleted in tumor-bearing mice either treated with shScr-ST or shIDO-ST. No change in shScr-ST numbers in isotype or Gr-1 depleted mice (FIG. 30d) was observed. However, significant increases of shIDO-ST were observed in tumors when mice were depleted of PMN, suggesting that PMN play a direct role in bacterial clearance from the tumor. Furthermore, in the absence of PMN (Gr-1 depleted), greater numbers of shIDO-ST colonization (P<0.05) were observed as compared to shScr-ST control, suggesting that IDO silencing plays a critical role in enhancing ST colonization.

Thus combining shIDO with ST presents a strategy to increase colonization of ST and may overcome previous deficiencies in colonization associated with using VNP20009 alone in clinical trials of metastatic melanoma.

The use of the natural properties of *Salmonella* or IDO inhibition for exploiting PMNs as effectors for tumor killing has not been done. Although PMNs are known to accumulate in *Salmonella*-colonized spleens (Kirby et al. 2002), it was unclear why PMNs were not recruited to *Salmonella*-colonized tumors (FIGS. 27a-b). By silencing IDO with shIDO-ST, it was determined that PMNs, like tumor-specific T-cells, are subject to IDO-mediated immunosuppression. However, unlike adaptive T-cell immunity, PMNs are more efficiently activated, have superior antitumor effects, and, most importantly, are not subject to tolerance, anergy, or exhaustion. It has already been shown that extended control of tumor growth after repeated administration of shIDO-ST (data not shown) demonstrates long-term and continuous effectiveness of the treatment.

Further investigation into the translational efficacy of shIDO-ST can be realistically evaluated using a variety of human IDO-expressing tumor lines (Uyttenhove et al. 2003 in xenogeneic mouse models. Moreover, previous clinical use of VNP20009 (Toso et al. 2002) makes translation of shIDO-ST more practical. The ability to overcome systemic off-target effects (Pawelek et al. 1997), accessibility to residual tumor (Challacombe et al. 2006), and its independence from adaptive immunity, which is prone to immunosuppression and escape by numerous mechanisms (Maeurer et al. 1996; Igney et al. 2002; Paschen et al. 2003), makes shIDO-ST a superior alternative to current immunotherapeutics being tested in the clinic. In sum, an alternative therapeutic strategy that highlights newly described roles for IDO and *Salmonella* in innate immunity and tumor regression has been developed and characterized as described herein. The capacity for ST to colonize any solid tumor increases the potential of shIDO-ST as a therapy to control a variety of cancers via targeted PMN cytotoxicity.

Example 4

Mechanisms of shIDO-ST Anti-Tumor Efficacy and Escape from Tumor Regression

The Examples above present two approaches for eliciting tumor regression using ST delivery: vaccine+shRNA or shRNA alone. This Example focuses on mechanistically associating knockdown of IDO expression with durable tumor regression. Since it was observed that the therapeutic efficacy of shIDO-ST was unaltered by T cell depletion, additional myeloid and lymphocyte subsets were evaluated, which uncovered that PMN populate tumors during regression. However, factors that trigger PMN trafficking beyond microbial infection should be identified (Bennouna et al. 2003; Breitbach et al. 2007), to account for the striking PMN intratumoral infiltration only when shIDO is combined with ST. In addition, questions regarding the mechanism for PMN expansion (e.g., intratumoral proliferation or trafficking from lymphoid organs) and PMN's depletion impact on tumor growth (Medina-Echeverz et al. 2011) will be addressed.

Figure 32:
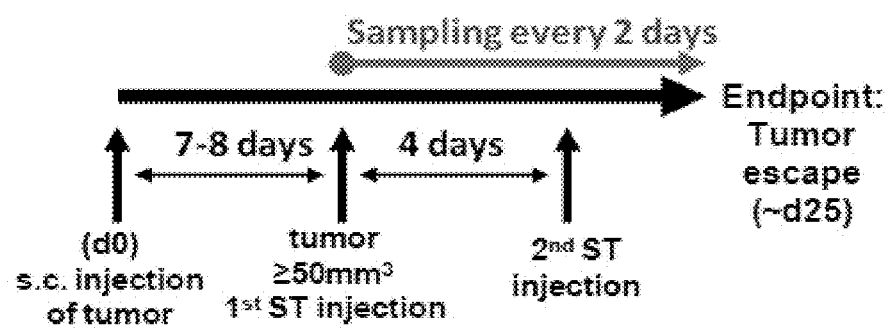
FIG. 32 shows a time course for sampling during proposed experiments according to some embodiments.

Time course of shIDO-ST treatment related events relevant for tumor growth inhibition. As shown in the Examples above, cross-sectional time points of shIDO-ST treatment of B6 mice with s.c. B16 melanomas have been evaluated. However, it is important to accurately describe the order of physiologic events that take place after shIDO-ST i.v. administration with respect to PMN migration, ST colonization, and intratumoral cell death. Therefore, a longitudinal study of events that occur immediately after the first and second administration of ST (i.v.) in B6 mice may be performed. The study as shown in FIG. 32 includes an injection of tumor cells at day 0, followed by a first ST injection when the tumor is greater or equal to 50 mm$^3$ (after about 7-8 days). A second ST injection will be administered 4 days following the first injection, with individual mice groups harvested every other day starting from the first injection, until the endpoint of tumor escape on ~d25. Approximately 6 mice/group for each ST type may be evaluated simultaneously at each time point. The time course study may be repeated. Both shIDO-ST and shScr-ST strains may be evaluated simultaneously, since ST has antitumor properties separate from the molecular activity of shRNA (Luo et al. 2001; Rosenberg et al. 2002). This approach will yield a comprehensive time map to evaluate physiologic events after ST inoculation and will allow us to concentrate on individual time points of interest in the following examples.

In an alternative method, the timecourse may be modified by extending sampling starting before the 1st injection and then proceed with sampling daily from the first ST injection onward.

Measurement of shIDO knockdown of IDO in B6 mice. In the initial studies described in Example 3 in which IDO knockdown in ST-treated B16 tumor-bearing mice, only a single time point was evaluated. To study the long-term effect of shRNA on IDO expression, a longitudinal study may be performed to link IDO knockdown with tumor regression, ST colonization, and PMN infiltration. This may be accomplished by using the same time course described above (FIG. 32) to measure IDO decline and its correlation with other parameters measured in the Examples above. Dual monitoring of IDO and GAPDH expression will be employed using RT-qPCR to normalize changes in IDO mRNA. All measurements will be conducted at least twice using triplicates and several organs will be evaluated, including TDLN, spleen, liver, and s.c. tumor. Since IDO expression occurs in TDLN and spleen when tumor is present (Munn et al. 2004; Friberg et al. 2002; Sharma et al. 2007), the kinetics of IDO mRNA expression and knockdown may be evaluated after systemic ST infection. Measuring IDO in tumor will be important, especially in IDO-KO mice.

Linkage of shIDO knockdown with tumor regression may be aided by detecting PMN chemokines & cytokines using RT-qPCR, e.g. those cited below. Changes in the intratumoral levels of these factors may provide further insight in the chemotaxis and proliferation of PMN in the tumor microenvironment.

Infiltration of s.c. melanoma tumors with myeloid and t cell subsets in B6 mice and timecourse. The observations described in above highlight tumor regression caused by shIDO-ST through a T cell independent mechanism, which is substantially different from other IDOi that have been published in the last decade, but is a unique feature of the system and VNP20009 described herein. In addition, the observation that substantial PMN infiltration of s.c. tumors extended for several days during therapy was made. Moreover, the Gr-1 mAb85 that may be used (RB6-8C5) is comprised of 2 components, Ly6G, which marks PMN exclusively, and Ly6C, which detects other subsets including MDSC86. Comparing results in FIG. 27 demonstrates congruence of Gr-1 and Ly6G staining, implicating PMN. The longitudinal time course in described above (FIG. 32) may be used to consecutively evaluate mice with tumors for PMN accumulation using Ly6G mAb. In addition, spleen and TDLN may be examined for evidence of PMN expansion or contraction. Ly6C and Ly6G mAb may be utilized to detect expansions of both MDSC and PMN subsets during time frame when shIDO-ST causes tumor regression. CFSE staining may also be utilized to assess if intratumoral PMN expand by duplication or trafficking from other lymphoid organs by isolating Ly6G+ cells (1A8 mAb, Bio-Express) (Daley et al. 2008) using magnetic separation methods (Medina-Echeverz et al. 2011), followed by labeling with CFSE and reintroduction using tail vein injection (Zhu et al. 2009). CFSE levels may be quantified to determine if such levels are maintained or diluted in s.c. tumor, spleen, and TDLN. In addition, the observations shown in FIG. 23 establish that depletion of CD8, CD4, and NK subsets does not impede shIDO-ST effect, confirming earlier work with VNP20009. These studies may be expanded to include earlier time points immediately following the second shIDO-ST injection at 11 days post-tumor inoculation and every 3 days until tumor escape. The proposed experiments are designed to confirm that T and NK cells are dispensable in this system, and to verify the strikingly different mechanism of shIDO-ST versus chemical IDOi or other *Salmonella* approaches (Lee et al. 2011) to promote tumor regression.

To supplement this example, Ly6G+ cells may be magnetically purified and an adoptive transfer into tumor bearing animals may be conducted either with or without prior ST treatment. If a non-specific ST is introduced, it will act to traffic adoptively transferred PMN to the tumor, alternatively a single infection of shIDO-ST may be required to traffic adoptively transferred PMN and accelerate tumor destruction. ST treatment and tumor infiltration may be required to precede PMN migration and successful infiltration of tumors.

Colonization of ST in s.c. B16 melanoma. A significant finding that is illustrated in the Examples above is the specific colonization of s.c. melanomas by shIDO-ST in contrast to undetectable levels by shScr-ST. This result was confirmed at a single x-sectional time point (data not shown). ST may also be investigated in s.c. tumor, spleen, and liver to establish timing and correlation of ST levels and tumor regression. Two time points will be examined between ST injections and every 3 days post-second injection for ST levels in tumors until escape. Organs in at least 6 mice may be evaluated at each time point using in vitro techniques that were previously described (Manuel et al. 2011). Homogenizing the tumor allows counting of individual ST, but reveals nothing about their morphologic location. Therefore, organ sectioning will be employed followed by specific staining for ST in tumor and peripheral organ samples at each time point. Ultrastructure of tumors is examined to locate colonization by ST in healthy vascularized or necrotic areas that support ST growth. Earlier work showed that ST accumulates in necrotic spaces (Westphal et al. 2008; Forbes et al. 2003), but the unusually large concentration of shIDO-ST suggests localization may be altered, possibly because of diminished IDO and increased PMN influx. Pathology Core services may be utilized for obtaining frozen sections, and stain ST with LPS Ab and counter-stain nuclei with DAPI. Examining several different ST (Scr, Stat3) will confirm specificity of shIDO, since ST preferentially localizes in tumors (Clairmont et al. 2000; Pawelek et al. 2003; Rosenberg et al. 2002). The effect of PMN on ST colonization may be examined by depleting with either Gr-1 (RB6-8C5) that eliminates both MDSC and PMN or exclusively PMN-depleting Ly6G-specific (1A8) mAb. PMN depletion will not likely change intratumoral ST levels, because ST precedes and attracts PMN influx, however ST localization may be altered. Similarly, the effect of Gr-1 and/or Ly6G mAb cell depletion in tumor control may be investigated using shScr-ST or shStat3-ST.

Insight into PMN activation properties before & after ST infection may be observed by measuring levels of chemokines/cytokines expressed by PMN after 1-3 days of in vitro culture. PMN post-ST treatment will likely be more activated than naïve circulating PMN before ST treatment. Cytokines/chemokines cited below and PMN activation factors (CXCR1/2/4, CXCL1-10, CCR1-6) may also be measured (Mantovani et al. 2010; Wright et al. 2010; Yamashiro et al. 2001; Lazennec & Richmond 2010).

Time course of cell death in CD45+ and CD45− cell types in ST-treated tumors. Cell death was examined after two i.v. injections of shIDO-ST at a single time point 1 week after the second injection. Remarkably, it was discovered that there was extensive cell death in the CD45+ lymphocyte subset as well as in the CD45− subset that includes B16 tumor cells. This result is in contrast to what was observed using the shStat3+Max treatment in which there was massive cell death in the CD45− subset without evidence of CD45+ lymphocyte cell death. Insensitivity of shIDO-ST therapy to T cell depletion is likely consistent with the large amount of CD45+ cell death. A time course to assess viability and persistence of both CD45+/− subsets before and after shIDO and shStat3 ST injections may be conducted. Further, it will be confirmed that the majority of the CD45− population is Annexin V+B16 melanoma tumor cells detectable using HMB45 mAb (Abcam). This may be done using a triple stain of CD45, Annexin V, and HMB45. Similarly, the composition of the lymphocyte population that is Annexin V+ will be further characterized. This will be done by using mAb to surface markers that distinguish members of lymphocyte and myeloid subsets. These include CD4, CD8, and CD56 to detect lymphocytes and CD11b, Ly6G, Ly6C, F4/80 and CD83 for non-T cells. Cell death kinetics may be synchronous or asynchronous for both CD45+/− subsets based on ST and PMN infiltration. Evaluating the contribution of PMN to intratumoral cell death will be approached by conducting a Gr-1 or 1A8 depletion study as described above. Depleting PMN will likely reverse levels of cell death as seen in the Examples above, with concomitant tumor outgrowth. Cell death in the spleen may also be examined, since ST accumulation has been observed at early times after administration, though never as extensive as in the tumor.

These studies may be augmented by conducting TUNEL apoptosis assays (Chen et al. 2003; Buonocore et al. 2008)) and measuring Caspases (Scheel-Toellner et al. 2004; Srikanth et al. 2010) associated with apoptosis if Annexin V data is equivocal.

Figure 8:
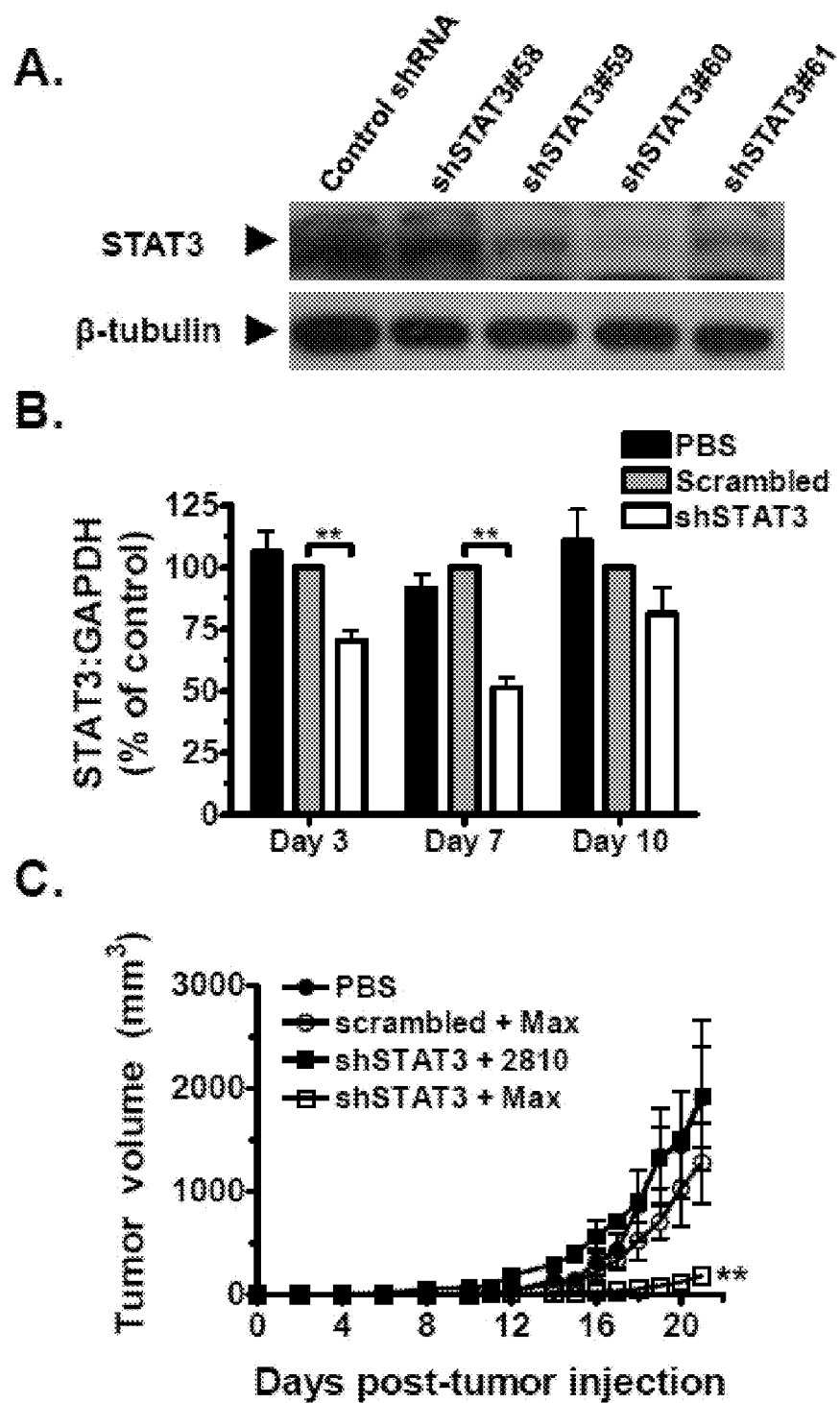
FIG. 8 shows the targeted silencing of STAT3 using YS1646-shSTAT3 resulting in significant suppression of tumor growth when combined with 3342Max. (A), western blot of STAT3 protein expression from B16F10 lysates after stable transfection of shRNA constructs (#58-61) with potential for silencing STAT3. β-tubulin is used as a loading control. (B), silencing of STAT3 expression in B16F10 tumor following intravenous (i.v.) injection of YS1646-shSTAT3. Mice bearing palpable B16F10 tumors were i.v. injected with $10^7$ cfu of YS1646-shSTAT3 twice, 4 days apart. Mice (n=3) were sacrificed on d3, d7, or d10 after first injection and tumor lysates were subjected to RNA extraction for qPCR analysis of STAT3 transcripts. STAT3 levels were normalized to the housekeeping gene GAPDH. (C), YS1646-shSTAT3 enhances anti-tumor effects of 3342Max in B16F10 model. B16F10 cells injected s.c. into C57BL/6 mice were allowed to reach a tumor volume of ~50 mm3 and then were treated with either YS1646-shSTAT3 or -scrambled by i.v. injection. Four days following this treatment, mice were then vaccinated with either MVP728-2810, -3342Max, or PBS.

Coordination of ST and endogenous myeloid cell homing with tumor regression and cell death. To gain insight into the mechanism of extensive intratumoral cell death and its linkage to PMN, intratumoral PMN levels may be quantitated during ST therapy. These studies require separate cohorts of mice that are inoculated with B16 melanoma and i.v. treated with shIDO-ST or shScr-ST control. Six animals at each time point may be used for each ST construct using a time course that initiates after the first ST administration, and consecutively harvests treated animals every two days until there is tumor escape in the shIDO-ST group (FIG. 32). Tumors may be excised and processed for flow cytometry as described above. In addition, it may be determined if an increase in PMN levels is dependent on IDO silencing when ST are localized in the tumor. IDO silencing is measured as described above. Mechanisms to explain effect of PMN on tumor cell viability may be evaluated by conducting in vitro cytotoxicity assays as previously described (Fridlender et al. 2009; Beauvillain et al. 2007; Tomihara et al. 2010). Infiltration of PMN immediately preceding intratumoral cell death, may explain the regression for an approximately 3 week period (FIG. 8). Using the same tumors in which were proposed to quantitate PMN and ST levels, PMN may be harvested using mAb-coated magnetic methods and co-cultured with Cr51-labeled B16 cells using a previously described method (Manuel et al. 2011). Relevant controls will include EL4 (H2b) tumor cells, and PMN effectors from shScr or shStat3 expressing ST from animals previously inoculated with B16 or naïve. Establishing that shIDO-ST infection precedes intratumoral infiltration of PMN may result from the timecourse, but require Gr-1 or 1A8 in vivo cell depletions to confirm PMN requirement for tumor regression independent of ST colonization.

Direct killing of tumor cells by PMN is likely, however, chemokines and cytokines secreted by PMN may be a cause of tumor cell death. This may be addressed using Transwell chambers (Chen et al. 2003; Rodriguez et al. 2009) in which activated or naïve PMN are in the top chamber and B16 cells on bottom, and Annexin V may be measured after 1-3 days of culture. Chemokines & cytokines will be identified from PMN cultures using Luminex™ technology. Coupled with in vitro cytotoxicity, this will provide insight into the mechanism of tumor cell killing by PMN.

Differences in mechanism of IDO inhibition by chemical IDOi (1-MT and menadione) and shIDO-ST in B6 mice. A clear difference of shIDO-ST versus other chemical IDOi is insensitivity to T and NK cell depletion. This profound difference is likely related to the strong PMN infiltration that was shown in FIG. 27a and discussed above. Two previously studied IDOi may be used to study this difference. The best studied is 1-MT (Uyttenhove et al. 2003; Cady et al. 1991), while the lesser known menadione (Kumar et al. 2008) also has strong IDOi activity. It will be determined whether providing 1-MT (oral) or menadione (i.v.) following the 1st injection of shIDO-ST changes tumor growth kinetics after the 2nd dose of shIDO-ST is given. Single depleting mAb have been investigated for their effect on shIDO-ST activity, but multiple depletions have not been investigated. Multiple cell type depletions may be conducted simultaneously including combined CD4 and CD8 or CD8 and NK subsets to confirm shIDO-ST effectiveness and chemical IDOi ineffectiveness to inactivate IDO when T cells are depleted. A time course as described above (FIG. 32) may be conducted to examine when IDO function is most profoundly depressed by IDOi, and if depletion of lymphoid subsets (CD4, CD8, or NK) alters therapeutic activity of combined shIDO-ST and chemical IDOi treatments. Further, it may be determined whether PMN depletion effects tumor growth using combined anti-IDO treatments.

Detection of changes in Trp catabolism after shIDO-ST treatment that correlate with control of tumor growth. A characteristic of IDO activity is the conversion of both D and L forms of Trp to the metabolite Kyn and other toxic metabolites to T lymphocytes (Lob et al. 2009). The IDO enzyme is inducible in lymphocytes and in other cell types outside the liver where an additional enzyme (Trp-dioxygenase) is responsible for L-Trp metabolism (Katz et al. 2008). Several Trp metabolites are known to be immuno-suppressive and equally important is that Trp starvation is thought to blunt T cell proliferation and function. One of the striking changes that shIDO-ST brings is the massive cell death of lymphocytes in growing melanomas. However, prior to shIDO-ST treatment, tumor growth accelerates and it is known from prior studies that T cell function is severely blunted (Munn et al. 2005; Uyttenhove et al. 2003). Therefore, it is likely that differences in Trp and its metabolites can be quantitated before and after shIDO-ST addition. These studies have been conducted preliminarily by cell extraction and HPLC fractionation of perchloric acid (PCA) extracted tissue, followed by neutralization and separation on an HPLC C18 column (Hyersil ODS, Thermo-Scientific, Waltham). The time course of Trp and Kyn metabolism may be investigated by conducting extractions of tumors using the time course described above, modified by additionally examining mice at day 0 and day 7 before application of shIDO-ST or control shRNA-ST. These studies are conducted using B6 mice which express endogenous IDO, besides the B16 tumor which also expresses IDO. Extracts before and after ST addition may be examined to correlate changes in tumor regression, PMN infiltration, and cell death based on the intratumoral Trp/Kyn ratio. Trp/Kyn ratios may also be measured in peripheral blood, spleen, and TDLN. Changes in Trp metabolism are likely if shIDO-ST is effective. The chemical measurement is specific, since only IDO produces Kyn as a metabolite in organs other than liver (Macchiarulo et al. 2009); therefore, measurement of Kyn levels will likely reflect levels of IDO intratumorally and the activity of shIDO-ST to limit IDO function.

Assessment of shIDO-ST infection related events in peripheral organs. ST infiltration is desirable in tumors, though not in peripheral organs which could lead to immune-pathology. To determine whether shIDO-ST causes systemic pathology in contrast to shScr-ST and shStat3-ST, whose effect caused minimal intratumoral cell death, a limited toxicology study may be conducted to assess off-target effects of shIDO-ST that could lead to possible adverse reactions in important peripheral organs such as lungs, spleen, and liver. Internal organs from mice that receive different ST, either 0, 1 or 2 doses with or without s.c. tumors may be harvested and evaluated for ST colonization of peripheral organs, cell death, and PMN infiltration at a single timepoint, 1 week following application. Cytokines and chemokines associated with PMN activation (Fridlender et al. 2009; Challacombe et al. 2006; Cassatella 1999; Mantovani et al. 2010; Wright et al. 2010; Wang et al. 2009; Di Carlo et al. 2001) (IP10, MCP-1, MIP-1a, IL1β, IL6, IL8, IL10, TNFα, TRAIL, Rantes, & CXCL1) by RT-qPCR and GCN-2 (Munn et al. 200540) associated with ST infection (Wick 2004) and Trp depletion (Muller et al. 2008). Comparison of animals with and without tumor also provides insight into the role of intratumoral infection and homing by shIDO-ST, and whether it contributes to pathology that is independent of any off-target effect in peripheral organs. Two ST strains may be compared, shIDO and shScr, and shStat3-ST may be added as an additional gene-specific ST to confirm results with shScr.

Analysis of environmental cues preceding tumor progression. In therapeutic evaluations of shIDO-ST tumor escape was observed at ~25 d after initial tumor challenge. Quantitative changes may be identified in the 3 component system comprised of tumor cells, shIDO-ST and PMN when tumors progress. Necrotic tumors may starve ST for nutrients, causing migration to other tissues thereby redirecting PMN attack. The time frame following the second i.v. ST administration may be investigated through tumor escape. Groups of animals (n=6) that are administered either shIDO-ST or shScr-ST may be evaluated for intratumoral cell composition and ST concentration every 3 days for approximately 3 weeks following the second ST injection. As escape occurs, s.c. tumors are harvested and molecular changes are investigated using an RT-qPCR approach. Annexin V and Caspase 3 may decrease, Stat3 phosphorylation, IL-18 (Cho et al. 2000), and FasL (Chen et al. 2003) may increase and variable levels of cytokines/chemokines are likely to be variable. Morphological ST localization may be investigated by IHC and intratumoral levels of ST may be quantitated during tumor regression.

Example 5

Evaluation of shIDO-ST in Tumor Models and an Increase in Durability of Regression The striking data above reflects the strong activity of a single shRNA delivered by ST. Here, the treatment may be broadened to identify synergistic or additive immune elements. To do so, contributions of host and intratumoral expressed IDO may be differentiated using IDO-KO, GCN2-KO or other suitable mouse models. KO mice for IDO, GCN2 (Munn et al. 2005), and Rag-1 are all commercially available (JAX, Bar Harbor). The GCN2-KO mouse addresses a metabolic signaling system that is activated during Trp starvation and is required for chemical IDOi function (Sharma et al. 2009). Rag1-KO mice have no adaptive immunity, because of complete ablation of adaptive B and T cells, thereby testing if shIDO-ST activity is absolutely T and B cell independent (Hou et al. 2007). Therapeutic efficacy of shIDO-ST exceeds the 2-component model of vaccine and shRNA described in Example 2. Yet, tumors may still escape, so the shIDO-ST approach may be improved to extend regression duration or cause rejection. To extend efficacy knockdown of IDO2 may be evaluated, a molecule related to IDO or the strong immunosuppressive molecule, TGFβ. These additional shRNA will be inserted into YS1646 making them of clinical interest, based on prior clinical use of GMP grade YS1646 referred to as VNP20009 (Toso et al. 2002; Nemunaitis et al. 2003; Heimann & Rosenberg 2003).

Further, shRNA and T cell dependent chemical IDOi may be combined, which may extend efficacy by establishing long term immunity. Rag1-KO mice may be applied similar to how B6 mice were utilized in the Examples above. While it is essential to establish a molecular and physiologic mechanism for the efficacy of shIDO-ST in a single tumor model, by extending breadth using other solid tumor models that produce IDO, generality and greater mechanistic understanding may result. Data related to Pan02 (FIG. 15), 4T1, and EL4 models show that these models may be good candidates for generalizing the shIDO-ST therapeutic approach to other responsive tumor types.

Evaluation of the impact of multiple shIDO-ST treatments and dose escalation in B6, IDO-KO, and Rag1-KO mice. In preliminary therapeutic data, a single approach of providing two doses of shIDO-ST in a tight concentration range varying from $10^6$-$10^7$ cfu/dose was used. Using different mouse models and tumors, varying doses and ST concentration may provide an extended therapeutic benefit. Therefore, adding an additional dose of shIDO-ST 4 d beyond the 2nd dose in B6 mice may be investigated. Further, escalation of ST by doubling the dose until a toxic level is reached will be evaluated, demonstrated by a 30% weight loss and/or diminished vitality (fur ruffling, slow movement, etc.) in B6 mice. The optimal dose number and levels using IDO-KO and Rag1-KO mice after B6 studies will be investigated.

Preliminary studies using IDO-KO mice have been performed, however, a more systematic evaluation may be necessary to extend durability of tumor regression. The method that may be used to evaluate the success of additional injections and dose escalation is measurement of tumor growth curves starting with tumor size ~50 mm³ when initiating therapy of B16 melanoma. Comparisons of different levels and amounts of shIDO-ST will be controlled using the standard of $2.5 \times 10^6$ cfu which obviates the need for an additional control ST or shRNA. The dose modifications may be adapted by including additional shRNA as described above, once potential synergy or additive affects are first established by empirical observation. The goal of this study is to extend the durability and efficacy of shIDO-ST alone, or as mixtures with additional shRNA, then to extend to other tumors as described below.

Using IDO-KO mice, studies using GCN2-KO mice may be repeated to investigate if shIDO-ST inhibition of IDO is independent of host adaptive immunity. shIDO-ST will likely be functional to suppress B16 growth but chemical IDOi will be incapacitated in the GCN2-KO mouse.

Administration of shIDO2 and TGF/β to extend the period of regression exerted by shIDO. The discovery of IDO2 (Metz et al. 2007), a second form of the IDO enzyme, may mean that both IDO enzymes may need to be inactivated for complete inhibition of IDO metabolism. The approach to constructing an ST expressing shIDO2 follows the same process as shIDO utilizing commercially available plasmids which target the IDO2 mRNA. An shRNA sequence causing >70% knockdown of IDO2 may be identified by conducting in vitro evaluations using co-transfection of IDO2 cDNA and shIDO2 expression plasmids in HEK293T cells. The chosen shIDO2 plasmid will be electroporated into YS1646 and evaluated as described above. Studies of IDO2 have been primarily conducted in humans (Witkiewicz et al. 2009), therefore, the role of IDO2 in mice is incompletely understood. Initially, the therapeutic efficacy of shIDO2-ST may be evaluated alone, using B6, IDO-KO, and Rag1-KO mice. This is to assess shIDO2 as a single agent therapeutic and sensitivity to T cell depletion similar to other chemical IDOi, or alternatively like shIDO. Then, mixtures of shIDO and shIDO2 or consecutive administration of each may be tested as a second or third injection following the format described above. Because the mechanism of IDO and IDO2 in causing tumor regression is unknown, mixtures of both shRNA, and separately shIDO2 following shIDO and the reverse may be administered, using tumor regression as the primary outcome. An additional approach is to silence a soluble mediator of immunosuppression, TGFβ. This molecule is known to be secreted by tumors and MDSC with the effect of inhibiting T cell responses (Marigo et al. 2008). Knockdown of TGFβ may work in cooperation with shIDO and/or shIDO2, or may have properties that are superior to either IDO enzyme for immunosuppression (Belladonna et al. 2008). Evaluation of shTGFβ should be approached similarly to the approach for shIDO2 by first administering a single dose of the knockdown therapeutic.

Following confirmation of effect, mixtures of shTGFβ, given as a primary injection may be evaluated, followed by shIDO or vice versa. The construction of shTGFβ and assessment of knockdown efficiency will be conducted as was proposed with shIDO2 by using commercial plasmids with constructed knockdown cassettes and co-transfection of full-length TGFβ in HEK293T cells. The most efficient shTGFβ plasmid (>70% knockdown) may be electroporated into YS1646, and in vivo experiments will be conducted.

Combination strategies using chemical IDOi to enhance durability and long-term immunity. Because a combination of shStat3 with SVN causes protective immunity, another agent that is T cell dependent may establish long-term immunity to sustain tumor regression in the shIDO model. Combining shStat3 or SVN was previously investigated with shIDO-ST, but neither ST gave additive or synergistic effect (data not shown). However, anti-tumor effects of chemical IDOi combined with shIDO-ST or with other ST described above may be evaluated. The T cell-dependent chemical IDOi that are most well known are 1-MT12 and menadione (Kumar et al. 2008). One approach that may be evaluated is to therapeutically treat tumors (~50 mm$^3$) with shIDO-ST or combinations of shRNA-ST controlled using shScr-ST, followed by treatment with chemical IDOi during tumor regression phase (days 15-25). Treatment with chemical IDOi may depress IDO expression and invigorate T cell immunity. Alternating chemical and ST-based IDOi may overcome ST immune resistance. As controls, the IDO-KO and Rag-1-KO mice may be used, since chemical IDOi are non-functional in those KO animals and will provide a contrast to the immunocompetent B6 mouse model. Improvement of outcomes by chemical IDOi compared to its excipient as a control exceeding shIDO-ST alone will be measured as increased durability of tumor regression. Mouse groups of (N=6) should be sufficient to obtain statistical significance if there is additive or synergistic effect of combining treatments.

Investigation of shIDO-ST related physiologic changes to s.c. melanoma in IDO-KO and Rag1-KO mice. Conduct Aims 1.3-1.9 in IDO-KO and Rag1-KO mice. The studies described in Example 4 are performed in B6 mice since they represent a straightforward milieu, yet, valuable results in IDO-KO mice have been seen, and T cell depletion studies should be definitive by using Rag1-KO mice. Consequently, previous examples me be reinvestigated using IDO-KO and Rag1-KO mouse models. The justification for separate trials is the density of studies in Example 4 and complexity of conducting parallel studies using multiple animal models with as many as 3 separate shRNA groups (shIDO, Scr, shIDO2 or TGFβ). For this study, two unique animal models may be evaluated with one experimental and one control ST group. (1) The IDO-KO model eliminates all cellular sources of IDO expression, leaving only tumor-based IDO expression. (2) Rag1-KO mice are important since mAb-based T cell depletion is not absolute; therefore, Rag1-KO mice will confirm prior results. Select time points in the time course may be evaluated as follows: 2 days and 4 days after the first ST treatment and 4, 8, 12, and 16 days after the second ST treatment. The purpose of re-examining results using both KO models is the absence of IDO or T cells that will confirm less exact approaches in B6 mice.

Validation of shIDO-ST Therapy in an unrelated melanoma model: JBRH (Syngeneic to B6 mice). Experiments in the well-studied B16 melanoma model may have greater translational impact if an independently derived melanoma responded to shIDO-ST therapy. The melanoma line JBRH was derived at MSKCC, and has been used extensively to compare to B16 (Cote et al. 2011; Belavance et al. 2011). The therapeutic effectiveness of shIDO-ST to control growth of the non-immunogenic JBRH melanoma will be evaluated in B6 mice. The main goals of this study are to evaluate shIDO-ST in an unrelated melanoma, examine mechanisms of tumor killing involving PMN, T cell depletion, and shIDO-ST colonization. In the case of minimal IDO expression, JBRH cells may be retrovirally transduced with IDO, and the therapeutic quality of shIDO-ST may be evaluated in IDO-transduced JBRH cells. The goal is to generalize the excellent therapeutic index found for B16 to an additional well-studied melanoma model. Obtaining qualified results in two models will establish the generality of the approach and encourage efforts towards clinical translation.

Identification of solid tumor models that respond to shIDO-ST treatment. A survey of mouse tumors that express IDO and may be conducted and 1 or 2 may be selected for further characterization. One model that may be used is Pan02 (Ishizaki et al. 2010), as this model has been shown to respond to shIDO-ST treatment (FIG. 15). Additionally, the model of EL4 lymphoma may also be used, which also expresses IDO and has been shown to have responsiveness in the SVN-ST model described above. Many other models including LLC, colon cancer CT26, prostate cancer (Tramp), breast cancer (4T1), kidney cancer (Renca) are valuable to evaluate. All models will be evaluated for IDO expression and simple preliminary characterization for responsiveness to shIDO-ST in a therapeutic model comparing shIDO-ST, shScr-ST, and PBS control. Each tumor model may be used after titration to assess cell numbers required to develop progressive tumor masses in 10-14 days, similar to B16. Subsequently, N=6 animals will be used in a therapy model similar to FIG. 7. The two models that exhibit the best tumor response will be more thoroughly studied. The selected models may then be evaluated using the approaches described above. The requirements for an evaluable model include forming a solid tumor colonizable by ST, control by shIDO-ST, and intratumoral IDO expression. Other requirements may be better understood after conducting the survey study in a minimal therapy model that will establish the most responsive tumors to shIDO-ST therapy.

Example 6 shRNA Suppression of Arginase-1: Effect on Tumor Growth Alone and in Combination with SVN Vaccines In line with the approach carried out in the Examples above with respect to the shIDO system (see FIG. 12), studies to investigate the effect of silencing the Arginase-1 protein were conducted by co-transfection experiments as shown in FIG. 34A in HEK293 cells. In brief, as shown in FIG. 34A, all treatments received 0.5 μg of an Arginase-1 expression plasmid which was functional as shown in the lane in which a co-transfected sh-scrambled plasmid was included. In five additional lanes are shown the results of co-transfection with commercially obtained sh-Arginase-1 (shArg1) expression plasmids described above (SEQ ID NO:10-14), demonstrating various degrees of silencing of the Arginase-1 protein. The most complete silencing of the Arginase-1 protein was shown with shArg1-5 (SEQ ID NO:10), which was then selected for experiments shown in FIGS. 34-41. A gel loading control in which the beta-tubulin protein was detected in each lane is also shown in FIG. 34A. Details concerning the plasmids, transfection approach, and antibody detection reagents can be found above in the description of FIG. 34. To evaluate the therapeutic efficacy of targeting and silencing Arginase-1 in vivo with the Arginase-1 specific shRNA plasmid delivered by the clinically tested ST strain VNP20009 (shArg1), longitudinal measurements of subcutaneous B16F10 tumor growth were performed and compared to mice treated with the control sh-scramble RNA (shSCB).

Figure 34C:
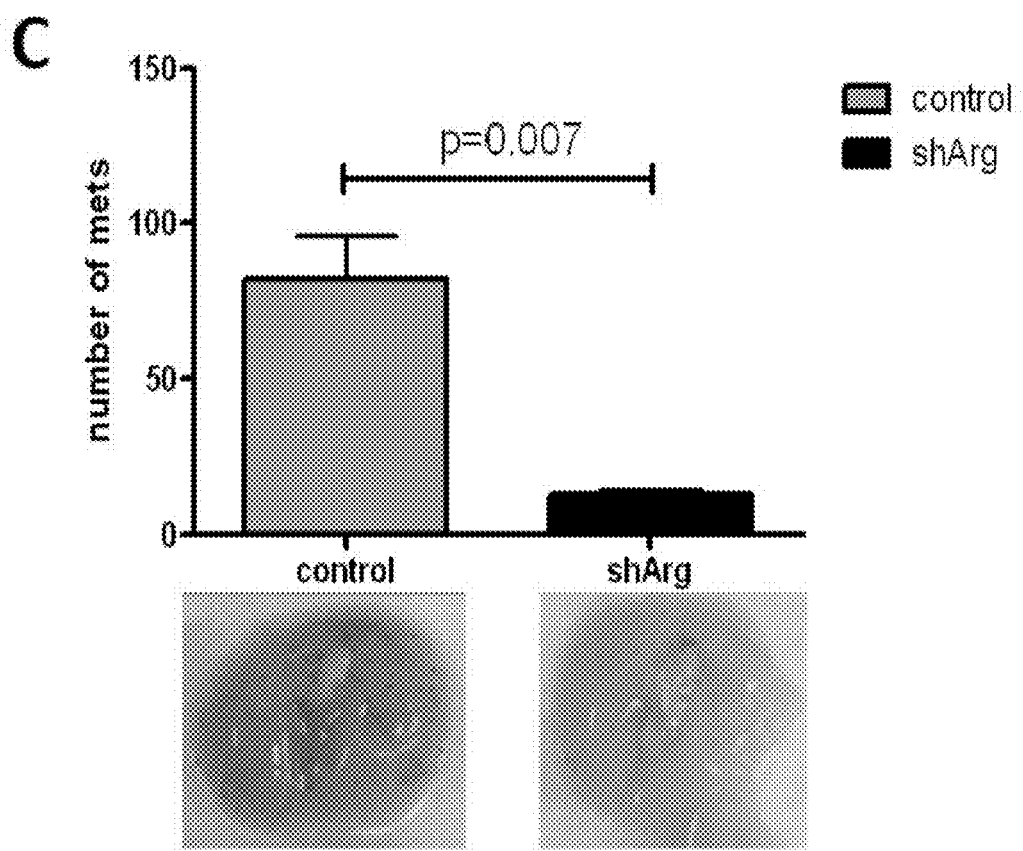
FIG. 34 shows targeted silencing of Arginase-1 using YS1646-shArg1 (shArg1) delays tumor growth when combined with MVP728-3342Max or alone. (A) ShRNA-expressing plasmids designed to silence Arginase I (Sigma, shArg1-5 through shArg1-9) were co-transfected into COS-1 cells with an Arg1-expressing plasmid at a ratio of 5:1 shRNA:Arg1. Western blot analysis of Arg1 expression was detected using Arg1-specific antibody (Santa Cruz Biotechnology, Santa Cruz, Calif.). β-tubulin is used as a loading control. Arg1-5 and Arg1-7 showed significant silencing of Arg1. Arg1-5 was selected for transformation into YS1646 to generate YS1646-shArg1. (B) Mice (n=4) bearing palpable subcutaneous (>50 mm$^3$) melanoma B16F10 (B16) tumors were treated with an initial intravenous injection of shArg1 ($5\times10^6$ cfu) followed by immunization with MVP728-3342Max or PBS (oral gavage; $1\times10^7$ cfu) and boosted subsequently with shArg1 on day 18 (shArg1 shown as sh ARG or sh Arg in Figure). Tumor volume was monitored over time. (C) For the metastasis model, C57BL6 mice (n=4) were challenged with B16 melanoma cells ($5\times10^5$) i.v. and treated with PBS (control) or shArg1 on day 1 and 7 (shArg1 shown as shArg in Figure). Lungs were removed on day 10 and metastatic plaques counted. Statistical significance based on Student t-test analysis where p<0.05.

Initial experiments assessed whether a synergistic effect could be shown by combining shArg1 treatment with the 3342Max vaccine (Salmonella strain that contains a plasmid that expresses the TAA survivin). FIG. 34B shows that shArg1 alone was as effective as the combination treatment with 3342Max vaccine. Systemic administration of shArg significantly suppressed tumor growth in comparison to control shSCB treatment. This therapeutic effect was also translated to a metastasis model, where mice treated with shArg1 had significantly fewer metastatic plaques in their lungs following intravenous challenge with B16F10 (B16) tumor cells (FIG. 34C).

Immunization with 3342Max had no therapeutic benefit in comparison to shArg1 alone (FIG. 34B), therefore, subsequent experiments focused on the anti-tumor effects of the monotherapy (i.e., single modality treatment) with shArg1. To identify the key effectors mediating the anti-tumor activity observed in FIG. 34, mice were depleted of distinct populations of leukocytes in vivo by the continuous administration of depleting antibodies. FIG. 35A demonstrates that administration of the various depleting antibodies significantly reduced the number of the target populations (CD4 T, CD8 T, MDSC and NK cells).

Treatment with shArg1 in the absence of CD4 or CD8 T cells was observed to be significantly less effective than animals treated with PBS (FIG. 35B). Thus, both CD4 and CD8 T cells are involved in the suppression of tumor growth following shArg1 treatment. In contrast, depletion of NK cells had no effect on tumor control by shArg1 treatment.

Myeloid derived suppressor cells (MDSC) were also shown to be involved in the therapeutic effects mediated by treatment with shArg1, as depletion of these cells with anti-GR1 antibody also significantly enhanced tumor growth and shortened survival (FIG. 35C). In summary, in vivo silencing of Arginase-1 can effectively attenuate tumor growth and its mechanism of action involves cell populations from both innate (MDSC) and adaptive (CD4$^+$ and CD8$^+$ T cells) immune systems.

MDSC were originally identified in tumor-bearing mice as cells that co-express CD11b and GR1; however currently, two main MDSC populations have been characterized: monocytic MDSC and granulocytic MDSC. In tumor-bearing mice, the granulocytic subset is the prevalent population of MDSC and these suppress antigen-specific CD8 T cells predominantly by producing ROS. However, on a per cell basis, the monocytic subset is more immunosuppressive and in human studies, the number of monocytic MDSC correlates directly with T cell suppression and poor clinical outcome (Dolcetti et al. 2010; Youn et al. 2008; Movahedi et al. 2008; Mandruzzato et al. 2009). Despite the differences in their immunosuppressive capabilities, both subsets of MDSC overexpress Arginase-1 and iNOS (Youn et al. 2012; Brandau et al. 2011; Lu et al. 2011; Bronte et al. 2005; Nagaraj et al. 2007; Molon et al. 2011).

Figure 36A:
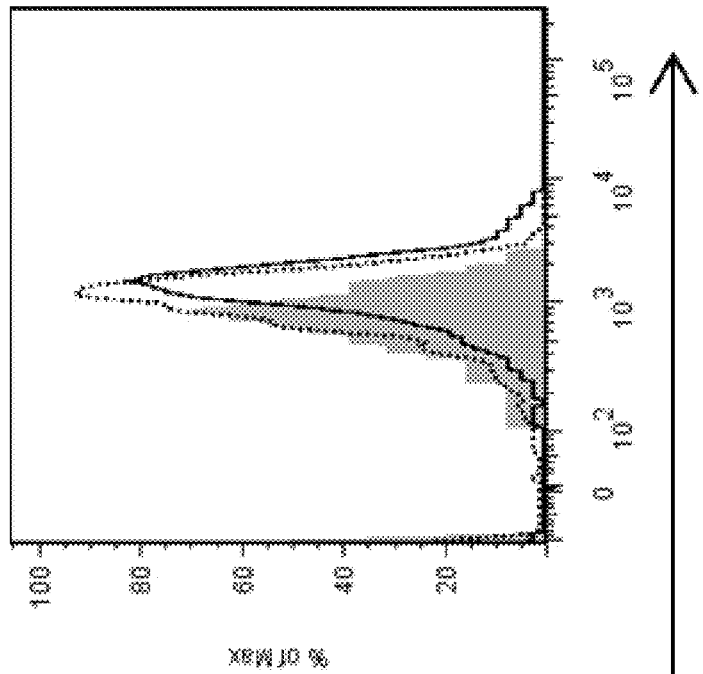
FIG. 36 shows in vivo inhibition of Arginase-1 in MDSC. B16 tumor bearing mice were treated with shArg1 or shSCB on day 11 and 15 as shown in FIG. 36A (shArg1 shown as shARG in Figure), and their spleens removed on day 16 for flow cytometry analysis. Splenocytes were surface stained for MDSC (surface markers CD11b and GR1) and dendritic cells (DC) (surface marker CD11c) and the intracellular expression of Arginase-1 measured following anti-Arginase I staining. FACS histograms show Arginase expression levels on MDSC and DC; control staining (solid grey), shSCB treated group (traced line) and shArg1 treated group (solid line) (FIG. 36B).
Figure 36B:
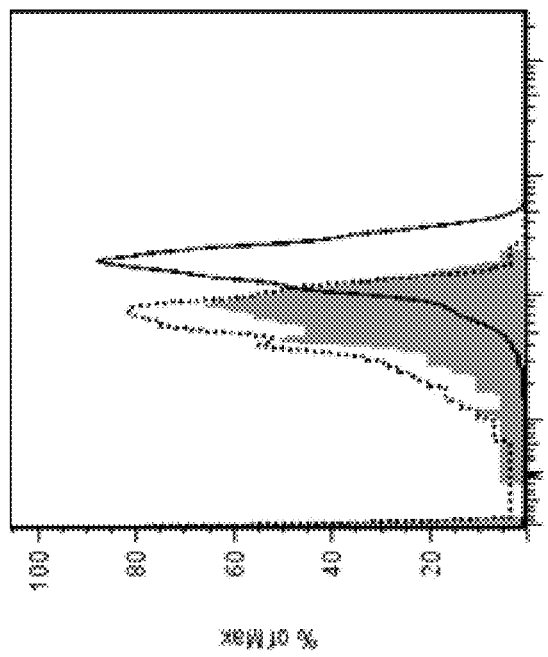

Therefore, the ability of shArg1 to effectively silence Arginase-1 within the MDSC population in vivo was evaluated by flow cytometry. Tumor bearing mice were treated with two injections of shArg1 (day 11 and 15) and on day 16 splenic MDSC (CD11b Gr1$^+$) and DC (CD11c$^+$) were examined for intracellular Arginase 1 expression levels (FIG. 36A). Systemic administration of shArg1 was shown to inhibit the expression of Arginase 1 at the protein level within the MDSC population compared to shSCB (FIG. 36B). No effect was detected in the DC population. These data support the findings observed in the in vivo depletion experiments which suggested that MDSC are important mediators of the therapeutic effects induced by the shArg1 monotherapy.

Figure 37A:
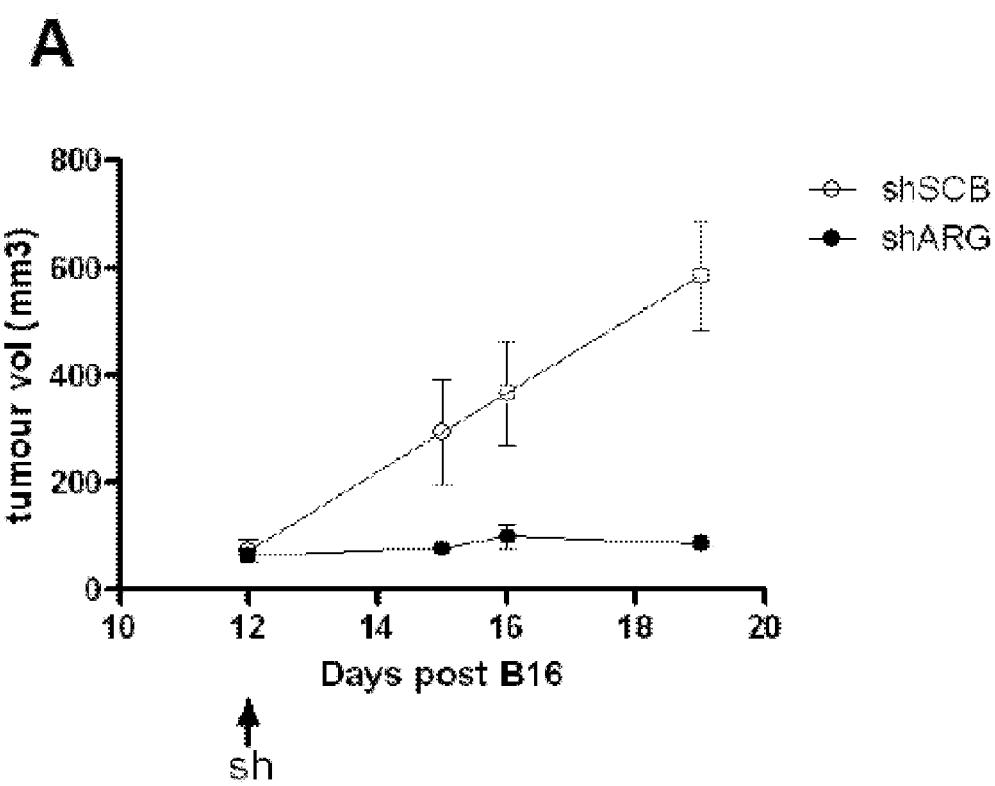
FIG. 37 shows in vivo targeted inhibition of Arginase-1 modifies the splenic and tumor microenvironment. (A) Tumor bearing mice treated with shArg1 or shSCB on day 12 were sacrificed on day 19 and the frequency of various populations of leukocytes within the spleen (B/D) and tumor (C/D) examined by flow cytometry phenotyping (shArg1 shown as shARG in Figure). (E) Both treatment groups (shArg1 and shSCB) had comparable number of CD4 T cells within the spleen, but the proportion of CD4 Foxp3$^+$Tregs was higher in the control group. Populations were defined as MDSC (CD11bGr1$^+$), macrophages (F4/80$^+$), natural killer cells (NK; DX5), NK T cells (CD3 NK1.1$^+$) DC (CD11c$^+$), CD4 T cells (CD3 CD4$^+$), CD8 T cells (CD3 CD8$^+$) and T regulatory cells (Tregs; CD4 Foxp3$^+$).

Further investigation of the effects of shArg1 treatment within the lymphoid organs and tumor microenvironment revealed that by silencing Arginase 1 there was a change in the frequency of different subsets of cells from lymphoid and myeloid lineages. Phenotypic flow cytometric analyses on splenocytes and tumors isolated from mice treated with a single injection of shArg1 suggest that in the spleen there is an increase in the number of MDSC following shArg1 treatment compared to shSCB. However, this does not reflect the tumor microenvironment, as this population was substantially lower within the tumors (FIG. 37A/B/C). These data suggest that shArg1 not only inhibits the expression of Arginase 1 within the MDSC population, but by doing so, it also affects their accumulation within the tumors, likely by making the microenvironment less immunosuppressive and favorable for their growth and/or recruitment. The number of macrophages (F4/80$^+$) was also elevated in both spleen and tumors of shArg1 treated mice and a decrease in the number of DC (CD11c$^+$) was observed in the spleen of these mice compared to the shSCB treated group.

Notably, when the frequency of the T cells was assessed there was no change in the number of CD4 T cells within the spleen of shArg1 treated group. However, a significantly higher number of tumor infiltrating CD4 T cells were detected (FIG. 37D). The number of CD8 T cells in the tumor was also elevated in the treated group compared to the shSCB control group, in contrast to a reduced frequency seen in the spleen. It is possible that CD8 T cells at this time point (day 19) had migrated out of the spleen towards the lymphoid organs draining the tumor or into the tumor itself (FIG. 37D). Although the number of CD4 T cells within the spleen was comparable between both treatment groups, the proportion of CD4 Foxp3$^+$ Tregs was higher in the control group (FIG. 37E). This bias towards a more immunosuppressive T cell activity was also seen within the tumor microenvironment where the ratio of Treg to T effector cells was higher in the shSCB control group. No difference was observed in the draining lymph node.

MDSC have been reported to mediate their immunosuppressive effects via an array of mechanisms involving both innate and adaptive immune cells. One of the reported mechanisms involves the activation and expansion of Tregs. MDSC have been demonstrated to promote the expansion of natural Tregs and the conversion of naïve CD4 T cells into induced Tregs, which explains the higher frequency of Tregs in the shSCB treated group that also has a higher number of MDSC within the tumor environment. The mechanism by which these cells enhance the expansion of Tregs and their suppressive function remains to be clarified but direct cell-cell contact via CD40-CD40L (Pan et al. 2010), secretion of suppressive cytokines such as IL-10, TGF-B (Huang et al. 2006) and also the expression of Arginase-1 (Serafini et al. 2008) are likely to be involved.

The depletion of essential nutrients like L-Arginine through the Arginase-1 dependent consumption by MDSC (Rodriguez et al. 2004) causes the downregulation of the CD3 ζ-chain of the T cell receptor which interferes with normal cell survival and differentiation signaling within these cells resulting in T cell cycle arrest. This supports the concept that MDSC directly inhibits T cell function. Thus, the expression levels of CD3 ζ-chain on splenic T cells and tumor infiltrating T cells was assessed by flow cytometry. The expression of the CD3 ζ-chain on splenic CD4 and CD8 T cells was unaltered (FIG. 38A). Similarly, tumor infiltrating CD4 T cells showed equivalent levels of CD3 ζ-chain (FIG. 38B). By contrast, tumor infiltrating CD8 T cells from the shSCB control group expressed approximately 50% less CD3 ζ-chain than their shArg1 counterparts. This suggested that the overexpression of Arginase-1 within the microenvironment has a direct effect on the expression of a functional T cell receptor on the CD8 T cell population, which may be responsible for the less effective anti-tumor responses (FIG. 38B).

MDSC can skew the local environment towards being more immunosuppressive by directly altering the activity of other cells of the innate system including macrophages and DC leading to a diminished inflammatory response or the secretion of cytokines that promote the expansion of MDSC as has been previously demonstrated (Sinha et al. 2007; Ostrand-Rosenberg et al. 2009; Bunt et al. 2009). MDSC secretion of IL-10 has been shown to impair TLR-induced IL12 by DC and consequently reduce DC mediated activation of T cells (Hu et al. 2011).

The ability of mature antigen presenting cells such as DC to activate naïve tumor specific T cells is thought to be important for the mounting of an effective and sustained anti-tumor response. Upon DC activation, the upregulation of co-stimulatory molecules, such as CD40 as well as MHC-II, is accompanied by an increased ability of these cells to prime T cells and activation of T cells in the absence of such co-stimulatory molecules can render T cells anergic. By utilising the expression of MHC-II molecules as a surrogate marker for DC activation status, splenic DC from mice treated with shArg1 were shown to express similar levels of MHC-I and CD1d molecules. However, MHC-II levels were markedly higher in the shArg1 treated group suggesting that the suppression of Arginase-1 has an effect on the maturation and activation status of DC in the spleen (FIG. 39A). When DC within the tumors were analyzed, the upregulation of MHCII and also CD1d was apparent reinforcing the hypothesis that by removing the suppressive activity of Arginase-1 within the tumor environment can lead to the enhancement of DC activation (FIG. 39B). As a result, more robust priming and effective maintenance of anti-tumor T cells within the tumor microenvironment is established. This is reflected in the higher numbers of tumor infiltrating CD4 and CD8 T cells and tumor control. The increased expression of the non-polymorphic MHC-I like CD1d molecule by tumoral DC also indicates the possible involvement of NKT cells in this setting, as these cells recognize tumor glycolipids presented by DC on CD1d molecules and have been shown to have anti-tumor activity and are currently being targeted in the clinic (Terabe et al. 2007).

An alternative mechanism employed by MDSC to non-specifically diminish the anti-tumor effects of a variety of effector cells present in the local tumor environment is the generation of oxidative stress, which is caused by the production of ROS and reactive nitrogen species. Peroxynitrite and hydrogen peroxide are generated by the combined and cooperative action of Arginase-1, iNOS and NADPH oxidase all expressed by MDSC. These cells have been shown to generate large amounts of reactive species, which interfere and block T cell function at different levels. Such interference includes loss of CD3 ζ-chain expression (Schmielau et al. 2001) and alterations in IL-2 receptor signaling (Mazzoni et al. 2002) due to the nitration/nitrosylatrion of amino acids like cysteine, methionine, tryptophan and tyrosine resulting in the desensitization of the T cell receptor which is required for T cell proliferation and survival. In addition, recent data demonstrate that the nitration of chemokines (e.g. CCL2) has a profound impact in the migration of T cells to the tumor environment, in addition to an enhanced recruitment of MDSC to this site (Molon et al. 2011).

Figure 40A:
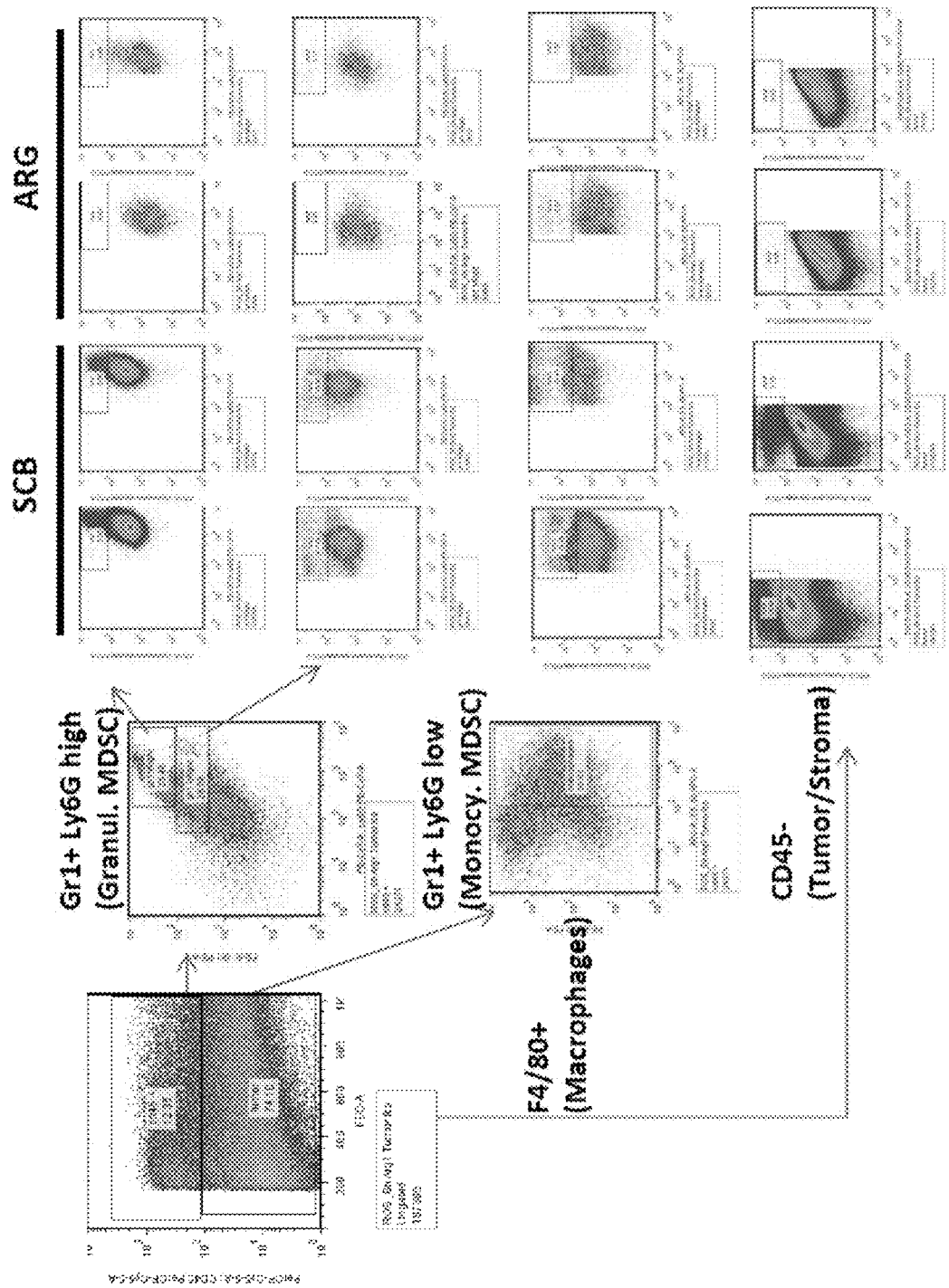
FIG. 40 shows in vivo treatment with shArg1 (shown as ARG or shARG in Figure) reduces the number of myeloid cells generating reactive oxygen species (ROS). Splenocytes and tumors from mice challenged with B16 (day 0) and treated with shArg1 or shSCB (day 12) were isolated on day 19 and stained for surface markers (CD11b Ly6G$^+$ granulocytic MDSC; CD11b Ly6G$^-$ monocytic MDSC; F4/80$^+$ macrophages; CD45$^-$ tumor/stroma cells) and the membrane permeable non-fluorescent substrate 2',7'-dichlorofluorescin diacetate (DCFH-DA). DCFH-DA is converted to the fluorescent form DCF by reactive oxygen species (ROS), which is detectable by flow cytometry. (A) Live cells were first gated on CD45$^+$ leukocytic cells and subsequently into the three distinct myeloid phenotypes or the CD45$^-$ tumor/stroma population. Percentage of ROS positive cells in the tumor (B) and spleen (C) are shown. Statistical significance based on Student t-test analysis where p<0.05.

It was shown that all three myeloid subsets, including macrophages (the tissue resident cells derived from circulating monocytes), and both granulocytic and monocytic MDSC express significantly less ROS within the tumor of mice treated with shArg1 (FIG. 40A/B). Surprisingly, CD45⁻ tumor/stromal cells also generate significantly less ROS when Arginase-1 is inhibited, indicating that by targeting this enzyme in vivo, the balance and activity of various populations within the tumor microenvironment can be altered, thereby facilitating the expansion of existing tumor specific T cells within the tumors. These results are consistent with a model in which Arginase-1 lowers the L-Arginine concentration in the microenvironment, thus inducing iNOS to produce $O_2^-$ in addition to NO, the exclusive product of iNOS at higher L-Arginine concentrations. NO reacts with $O_2^-$, giving rise to peroxynitrite (ONOO⁻), a highly reactive oxidizing agent that nitrates tyrosines on proteins. Peroxynitrites can induce apoptosis in T lymphocytes by inhibiting activation-induced protein tyrosine phosphorylation (Brito et al. 1999) or by nitrating a component of the mitochondrial permeability transition pore, which causes release of death-promoting factors, such as cytochrome C (Aulak et al. 2001; Bronte et al. 2003). Furthermore, this change in microenvironment was not observed in the spleen, as these subsets of myeloid cells showed no differences in ROS production (FIG. 40C). This suggests that by delivering the shArg1 using a ST vector, the immune response can be activated locally where it is needed, preventing potential systemic tissue damage and autoimmunity.

Example 7 shRNA Suppression of iNOS

As shown in the Examples above, the data suggests that the production of ROS and possibly reactive nitrogen species (RNS) produced by MDSC and tumor cells may be involved in the maintenance of an immunosuppressive microenvironment. Since the production of RNS and ROS can be generated by the action of iNOS alone or in combination with Arginase-1, the potential therapeutic effects of silencing iNOS with an ST-shRNA was investigated with studies similar to those described above using commercially obtained shiNOS expression plasmids (SEQ ID NOs 15-19). To choose an shRNA that effectively silences iNOS, co-transfection experiments using 5:1 shRNA:iNOS plasmid ratios were done in COS-1 cells for 48 hours and lysates were analyzed by western blot for the expression of iNOS (FIG. 41A). ShiNOS-45 (SEQ ID NO:17) showed the most effective silencing of iNOS and was chosen for transformation of YS1646 to generate YS1646-shiNOS (abbreviated to shiNOS). FIG. 41(B-D) further shows that treatment of mice bearing melanoma cells (B16) expressing the TAA Wilms' tumor-1 (WT-1) with shiNOS can delay tumor growth. The therapeutic effects of shiNOS in combination with an ST-vaccine against WT-1 were not statistically significant, although there was a clear delay in tumor progression. However, when shiNOS treatment was combined with an MVA based vaccine against WT-1 a significant difference was observed, and shiNOS treatment was just as effective as shArg1 alone. Although shiNOS treatment with the vaccines delayed tumor growth, no synergistic action was seen when combining shiNOS and shArg1 together with the MVA-WT- 1. Vaccination with MVA-WT-1 alone showed no therapeutic effect. This suggests that the therapeutic effects of shArg1 may be mediated via the action of iNOS and its role in the generation of ROS/RNS.

Studies have reported that Arginase-1 activation limits L-Arginine as a substrate for iNOS and thereby negatively regulates its activity (Munder et al. 1999). However, in the current model, MDSC from shSCB treated mice had higher levels of ROS than the shArg1 group. Both enzymes have been reported to metabolize L-Arginine at similar rates (Fligger et al. 1999), but depletion of cytosolic L-Arginine in MDSC by Arginase-1 has an important effect on iNOS, where under these conditions Arginase-1 induces the switch in iNOS activity shifting its function from the production of mostly NO to peroxynitrites (Bronte et al. 1003; Xia et al. 1997; Xia et al. 1998).

The results shown in FIGS. 34-41 suggest that shArg1 treatment is inhibiting the production of reactive species by modulating iNOS activity; therefore, when iNOS was directly inhibited, anti-tumor effects were enhanced and tumor progression could be controlled (FIG. 41). Furthermore, simultaneous inhibition of both enzymes had no additional synergistic benefit, which reinforces the suggestion that iNOS may be generating peroxynitrite and oxidative stress downstream of Arginase-1 rather than via parallel pathways (FIG. 41D). These reactive species can have multiple inhibitory effects on T cells, which would lead to the anti-tumor effects induced by shArg1 or shiNOS therapy in addition to the other suppressive mechanisms related to L-Arginine availability within the tumor microenvironment.

REFERENCES

The references, patents and published patent applications listed below, and all references cited in the specification above are hereby incorporated by reference in their entirety, as if fully set forth herein.

Altieri, D. C. and Marchisio, P. C. Survivin apoptosis: an interloper between cell death and cell proliferation in cancer. Lab Invest, 79: 1327-1333, 1999.

Altieri, D. C. Validating survivin as a cancer therapeutic target. Nat Rev Cancer, 3: 46-54, 2003.

Anderson, M. J., Shafer-Weaver, K., Greenberg, N. M., and Hurwitz, A. A. Tolerization of tumor-specific T cells despite efficient initial priming in a primary murine model of prostate cancer. J Immunol, 178: 1268-1276, 2007.

Angelakopoulos H, Hohmann E L. Pilot study of phoP/phoQ-deleted *Salmonella enterica* serovar typhimurium expressing *Helicobacter pylori* urease in adult volunteers. Infect Immun. 2000; 68:2135-2141.

Aoki, Y., Feldman, G. M., and Tosato, G. Inhibition of STAT3 signaling induces apoptosis and decreases survivin expression in primary effusion lymphoma. Blood, 101: 1535-1542, 2003.

Arrach N, Zhao M, Porwollik S, Hoffman R M, McClelland M. *Salmonella* promoters preferentially activated inside tumors. Cancer Res. 2008; 68:4827-4832.

Aulak, K. S., et al. Proteomic method identifies proteins nitrated in vivo during inflammatory challenge. *Proc Natl Acad Sci USA* 98, 12056-12061 (2001).

Avogadri F, Martinoli C, Petrovska L et al. Cancer immunotherapy based on killing of *Salmonella*-infected tumor cells. Cancer Res. 2005; 65:3920-3927.

Baban B, Chandler P R, Sharma M D et al. IDO activates regulatory T cells and blocks their conversion into Th17-like T cells. J Immunol. 2009; 183:2475-2483.

Banerjee T, DuHadaway J B, Gaspari P et al. A key in vivo antitumor mechanism of action of natural product-based brassinins is inhibition of indoleamine 2,3-dioxygenase. Oncogene. 2008; 27:2851-2857.

Basu G D, Tinder T L, Bradley J M et al. Cyclooxygenase-2 inhibitor enhances the efficacy of a breast cancer vaccine: role of IDO. J Immunol. 2006; 177:2391-2402.

Baud, D., Ponci, F., Bobst, M., De Grandi, P., and Nardelli-Haefliger, D. Improved efficiency of a *Salmonella*-based vaccine against human papillomavirus type 16 virus-like particles achieved by using a codon-optimized version of L1. J Virol, 78: 12901-12909, 2004.

Beauvillain C, Delneste Y, Scotet M et al. Neutrophils efficiently cross-prime naive T cells in vivo. Blood. 2007; 110:2965-2973.

Belladonna M L, Volpi C, Bianchi R et al. Cutting edge: Autocrine TGF-beta sustains default tolerogenesis by IDO-competent dendritic cells. J Immunol. 2008; 181: 5194-5198.

Bellavance E C, Kohlhapp F J, Zloza A et al. Development of Tumor-Infiltrating CD8+ T Cell Memory Precursor Effector Cells and Antimelanoma Memory Responses Are the Result of Vaccination and TGF-{beta} Blockade during the Perioperative Period of Tumor Resection. J Immunol. 2011; 186:3309-3316.

Bennouna S, Bliss S K, Curiel T J, Denkers E Y. Cross-talk in the innate immune system: neutrophils instruct recruitment and activation of dendritic cells during microbial infection. J Immunol. 2003; 171:6052-6058.

Bereta M, Hayhurst A, Gajda M et al. Improving tumor targeting and therapeutic potential of *Salmonella* VNP20009 by displaying cell surface CEA-specific antibodies. Vaccine. 2007; 25:4183-4192.

Berghella, A. M., Pellegrini, P., Del Beato, T., Adorno, D., and Casciani, C. U. IL-10 and sIL-2R serum levels as possible peripheral blood prognostic markers in the passage from adenoma to colorectal cancer. Cancer Biother Radiopharm, 12: 265-272, 1997.

Bermudes D, Zheng L M, King I C. Live bacteria as anticancer agents and tumor-selective protein delivery vectors. Curr Opin Drug Discov Devel. 2002; 5:194-199.

Brandau, S., et al. Myeloid-derived suppressor cells in the peripheral blood of cancer patients contain a subset of immature neutrophils with impaired migratory properties. *J Leukoc Biol* 89, 311-317 (2011).

Breitbach C J, Paterson J M, Lemay C G et al. Targeted inflammation during oncolytic virus therapy severely compromises tumor blood flow. Mol Ther. 2007; 15:1686-1693.

Brito, C., et al. Peroxynitrite inhibits T lymphocyte activation and proliferation by promoting impairment of tyrosine phosphorylation and peroxynitrite-driven apoptotic death. *J Immunol* 162, 3356-3366 (1999).

Bronte, V., Serafini, P., De Santo, C., Mango, I., Tosello V., Mazzoni, A., Segal, D., Staib, C., Lowel M., Sutter G., Colombo M., & Zanovello P. IL-4-induced arginase 1 suppresses alloreactive T cells in tumor-bearing mice. *J Immunol* 170, 270-278 (2003).

Bronte, V., Serafini, P., Mazzoni, A., Segal, D. M. & Zanovello, P. L-arginine metabolism in myeloid cells controls T-lymphocyte functions. *Trends Immunol* 24, 302-306 (2003).

Bronte, V. & Zanovello, P. Regulation of immune responses by L-arginine metabolism. *Nat Rev Immunol* 5, 641-654 (2005).

Bunt, S. K., Clements, V. K., Hanson, E. M., Sinha, P. & Ostrand-Rosenberg, S. Inflammation enhances myeloidderived suppressor cell cross-talk by signaling through Toll-like receptor 4. *J Leukoc Biol* 85, 996-1004 (2009).

Buonocore S, Haddou N O, Moore F et al. Neutrophil-dependent tumor rejection and priming of tumoricidal CD8+ T cell response induced by dendritic cells overexpressing CD95L. J Leukoc Biol. 2008; 84:713-720.

Byrne, S. N. and Halliday, G. M. High levels of Fas ligand and MHC class II in the absence of CD80 or CD86 expression and a decreased CD4+ T cell Infiltration, enables murine skin tumours to progress. Cancer Immunol Immunother, 52: 396-402, 2003.

Cady S G, Sono M. 1-Methyl-DL-tryptophan, beta-(3-benzofuranyl)-DL-alanine (the oxygen analog of tryptophan), and beta-[3-benzo(b)thienyl]-DL-alanine (the sulfur analog of tryptophan) are competitive inhibitors for indoleamine 2,3-dioxygenase. Arch Biochem Biophys. 1991; 291:326-333.

Cassatella M A. Neutrophil-derived proteins: selling cytokines by the pound. Adv Immunol. 1999; 73:369-509.

Catic, A., Dietrich, G., Gentschev, I., Goebel, W., Kaufmann, S. H., and Hess, J.

Challacombe J M, Suhrbier A, Parsons P G et al. Neutrophils are a key component of the antitumor efficacy of topical chemotherapy with ingenol-3-angelate. J Immunol. 2006; 177:8123-8132.

Challacombe, J. M. et al. Neutrophils are a key component of the antitumor efficacy of topical chemotherapy with ingenol-3-angelate. *J Immunol* 177, 8123-8132 (2006).

Chen, G., Wei, D. P., Jia, L. J., Tang, B., Shu, L., Zhang, K., Xu, Y., Gao, J., Huang, X. F., Jiang, W. H., Hu, Q. G., Huang, Y., Wu, Q., Sun, Z. H., Zhang, J. F., and Hua, Z. C. Oral delivery of tumor-targeting *Salmonella* exhibits promising therapeutic efficacy and low toxicity. Cancer Sci, 100: 2437-2443, 2009.

Chen, Y. L., Chen, S. H., Wang, J. Y. & Yang, B. C. Fas ligand on tumor cells mediates inactivation of neutrophils. *J Immunol* 171, 1183-1191 (2003).

Cho D, Song H, Kim Y M et al. Endogenous interleukin-18 modulates immune escape of murine melanoma cells by regulating the expression of Fas ligand and reactive oxygen intermediates. Cancer Res. 2000; 60:2703-2709.

Ciorba M A, Bettonville E E, McDonald K G et al. Induction of IDO-1 by Immunostimulatory DNA Limits Severity of Experimental Colitis. J Immunol. 2010; 184:3907-3916.

Clairmont, C., Lee, K. C., Pike, J., Ittensohn, M., Low, K. B., Pawelek, J., Bermudes, D., Brecher, S. M., Margitich, D., Turnier, J., Li, Z., Luo, X., King, I., and Zheng, L. M. Biodistribution and genetic stability of the novel antitumor agent VNP20009, a genetically modified strain of *Salmonella typhimurium*. J Infect Dis, 181: 1996-2002, 2000.

Cote A L, Zhang P, O'Sullivan J A et al. Stimulation of the glucocorticoid-induced TNF receptor family-related receptor on CD8 T cells induces protective and high-avidity T cell responses to tumor-specific antigens. J Immunol. 2011; 186:275-283.

Dai, S. and Zhou, D. Secretion and function of *Salmonella* SPI-2 effector SseF require its chaperone, SscB. J Bacteriol, 186: 5078-5086, 2004.

Daley J M, Thomay A A, Connolly M D, Reichner J S, Albina J E. Use of Ly6G-specific monoclonal antibody to deplete neutrophils in mice. J Leukoc Biol. 2008; 83:64-70.

Dallegri, F. & Ottonello, L. Neutrophil-mediated cytotoxicity against tumour cells: state of art. *Arch Immunol Ther Exp (Warsz)* 40, 39-42 (1992).

De Vita, F., Orditura, M., Galizia, G., Romano, C., Roscigno, A., Lieto, E., and Catalano, G. Serum interleukin-10 levels as a prognostic factor in advanced non-small cell lung cancer patients. Chest, 117: 365-373, 2000.

Deepak, P. and Acharya, A. Anti-tumor immunity and mechanism of immunosuppression mediated by tumor cells: role of tumor-derived soluble factors and cytokines. Int Rev Immunol, 29: 421-458, 2010.

Deiwick, J., Nikolaus, T., Erdogan, S., and Hensel, M. Environmental regulation of *Salmonella* pathogenicity island 2 gene expression. Mol Microbiol, 31: 1759-1773, 1999.

Di Carlo, E. et al. Neutrophils in anti-cancer immunological strategies: old players in new games. *J Hematother Stem Cell Res* 10, 739-748 (2001b).

Di Carlo, E. et al. The intriguing role of polymorphonuclear neutrophils in antitumor reactions. *Blood* 97, 339-345 (2001a).

Dolcetti, L., et al. Hierarchy of immunosuppressive strength among myeloid-derived suppressor cell subsets is determined by GM-CSF. *Eur J Immunol* 40, 22-35 (2010).

Drake C G, Jaffee E, Pardoll D M. Mechanisms of immune evasion by tumors. Adv Immunol. 2006; 90:51-81.

Echchannaoui H, Bianchi M, Baud D et al. Intravaginal immunization of mice with recombinant *Salmonella enterica* serovar Typhimurium expressing human papillomavirus type 16 antigens as a potential route of vaccination against cervical cancer. Infect Immun. 2008; 76:1940-1951.

Evans, D. T., Chen, L. M., Gillis, J., Lin, K. C., Harty, B., Mazzara, G. P., Donis, R. O., Mansfield, K. G., Lifson, J. D., Desrosiers, R. C., Galan, J. E., and Johnson, R. P. Mucosal priming of simian immunodeficiency virus-specific cytotoxic T-lymphocyte responses in rhesus macaques by the *Salmonella* type III secretion antigen delivery system. J Virol, 77:2400-2409, 2003.

Fallarino F, Grohmann U, Hwang K W et al. Modulation of tryptophan catabolism by regulatory T cells. Nat Immunol. 2003; 4:1206-1212.

Fleming, T. J., Fleming, M. L. & Malek, T. R. Selective expression of Ly-6G on myeloid lineage cells in mouse bone marrow. RB6-8C5 mAb to granulocyte differentiation antigen (Gr-1) detects members of the Ly-6 family. *J Immunol* 151, 2399-2408 (1993).

Fligger, J., Blum, J. & Jungi, T. W. Induction of intracellular arginase activity does not diminish the capacity of macrophages to produce nitric oxide in vitro. *Immunobiology* 200, 169-186 (1999).

Forbes N S, Munn L L, Fukumura D, Jain R K. Sparse initial entrapment of systemically injected *Salmonella typhimurium* leads to heterogeneous accumulation within tumors. Cancer Res. 2003; 63:5188-5193.

Friberg M, Jennings R, Alsarraj M et al. Indoleamine 2,3-dioxygenase contributes to tumor cell evasion of T cell-mediated rejection. Int J Cancer. 2002; 101:151-155.

Fridlender Z G, Sun J, Kim S et al. Polarization of tumor-associated neutrophil phenotype by TGF-beta: "N1" versus "N2" TAN. Cancer Cell. 2009; 16:183-194.

Frumento, G., Rotondo, R., Tonetti, M., Damonte, G., Benatti, U., and Ferrara, G. B. Tryptophan-derived catabolites are responsible for inhibition of T and natural killer cell proliferation induced by indoleamine 2,3-dioxygenase. J Exp Med, 196: 459-468, 2002.

Gajewski, T. F., Meng, Y., and Harlin, H. Immune suppression in the tumor microenvironment. J Immunother, 29: 233-240, 2006.

Gaspari P, Banerjee T, Malachowski W P et al. Structure-activity study of brassinin derivatives as indoleamine 2,3-dioxygenase inhibitors. J Med Chem. 2006; 49:684-692.

Grohmann U, Orabona C, Fallarino F et al. CTLA-4-Ig regulates tryptophan catabolism in vivo. Nat Immunol. 2002; 3:1097-1101.

Gunn B M, Wanda S Y, Burshell D, Wang C, Curtiss R, III. Construction of Recombinant Attenuated *Salmonella enterica* Serovar Typhimurium Vaccine Vector Strains for Safety in Newborn and Infant Mice. Clin Vaccine Immunol. 2010; 17:354-362.

Haraga, A., Ohlson, M. B., and Miller, S. I. Salmonellae interplay with host cells. Nat Rev Microbiol, 6: 53-66, 2008.

Harding H P, Zhang Y, Zeng H et al. An integrated stress response regulates amino acid metabolism and resistance to oxidative stress. Mol Cell. 2003; 11:619-633.

Heimann D M, Rosenberg S A. Continuous intravenous administration of live genetically modified *salmonella typhimurium* in patients with metastatic melanoma. J Immunother. 2003; 26:179-180.

Hernandez-Ilizaliturri, F. J. et al. Neutrophils contribute to the biological antitumor activity of rituximab in a non-Hodgkin's lymphoma severe combined immunodeficiency mouse model. Clin Cancer Res 9, 5866-5873 (2003).

Hodi F S, O'Day S J, McDermott D F et al. Improved Survival with Ipilimumab in Patients with Metastatic Melanoma. N Engl J Med. 2010.

Hoshi M, Saito K, Hara A et al. The absence of IDO upregulates type I IFN production, resulting in suppression of viral replication in the retrovirus-infected mouse. J Immunol. 2010; 185:3305-3312.

Hou D Y, Muller A J, Sharma M D et al. Inhibition of indoleamine 2,3-dioxygenase in dendritic cells by stereoisomers of 1-methyl-tryptophan correlates with antitumor responses. Cancer Res. 2007; 67:792-801.

Hu, C. E., Gan, J., Zhang, R. D., Cheng, Y. R. & Huang, G. J. Up-regulated myeloid-derived suppressor cell contributes to hepatocellular carcinoma development by impairing dendritic cell function. Scand J Gastroenterol 46, 156-164 (2011).

Huang, B., et al. Gr-1+CD115+ immature myeloid suppressor cells mediate the development of tumor-induced T regulatory cells and T-cell anergy in tumor-bearing host. Cancer Res 66, 1123-1131 (2006).

Husseiny M I, Wartha F, Hensel M. Recombinant vaccines based on translocated effector proteins of *Salmonella* Pathogenicity Island 2. Vaccine. 2007; 25:185-193.

Hwu, P., Du, M. X., Lapointe, R., Do, M., Taylor, M. W., and Young, H. A. Indoleamine 2,3-dioxygenase production by human dendritic cells results in the inhibition of T cell proliferation. J Immunol, 164: 3596-3599, 2000.

Igney, F. H. & Krammer, P. H. Immune escape of tumors: apoptosis resistance and tumor counterattack. J Leukoc Biol 71, 907-920 (2002).

Introduction of protein or DNA delivered via recombinant *Salmonella typhimurium* into the major histocompatibility complex class I presentation pathway of macrophages. Microbes Infect, 1: 113-121, 1999.

Ishizaki, H., Manuel, E. R., Song, G. Y., Srivastava, T., Sun, S., Diamond, D. J., and Ellenhorn, J. D. Modified vaccinia Ankara expressing survivin combined with gemcitabine generates specific antitumor effects in a murine pancreatic carcinoma model. Cancer Immunol Immunother. 2010 DOI: 10.1007/s00262-010-0923-0.

Kallberg E, Wikstrom P, Bergh A, Ivars F, Leanderson T. Indoleamine 2,3-dioxygenase (IDO) activity influence tumor growth in the TRAMP prostate cancer model. Prostate. 2010; 70:1461-1470.

Katz J B, Muller A J, Prendergast G C. Indoleamine 2,3-dioxygenase in T-cell tolerance and tumoral immune escape. Immunol Rev. 2008; 222:206-221.

Kemp T J, Ludwig A T, Earel J K et al. Neutrophil stimulation with *Mycobacterium bovis bacillus* Calmette-Guerin (BCG) results in the release of functional soluble TRAIL/Apo-2L. Blood. 2005; 106:3474-3482.

King, I., Itterson, M., and Bermudes, D. Tumor-targeted *Salmonella typhimurium* overexpressing cytosine deaminase: a novel, tumor-selective therapy. Methods Mol Biol, 542: 649-659, 2009.

Kirby, A. C., Yrlid, U. & Wick, M. J. The innate immune response differs in primary and secondary *Salmonella* infection. J Immunol 169, 4450-4459 (2002).

Klebanoff C A, Acquavella N, Yu Z, Restifo N P. Therapeutic cancer vaccines: are we there yet? Immunol Rev. 2011; 239:27-44.

Koblish H K, Hansbury M J, Bowman K J et al. Hydroxyamidine inhibitors of indoleamine-2,3-dioxygenase potently suppress systemic tryptophan catabolism and the growth of IDOexpressing tumors. Mol Cancer Ther. 2010; 9:489-498.

Kortylewski, M. and Yu, H. Role of Stat3 in suppressing anti-tumor immunity. Curr Opin Immunol, 20: 228-233, 2008.

Kortylewski, M., Kujawski, M., Wang, T., Wei, S., Zhang, S., Pilon-Thomas, S., Niu, G., Kay, H., Mule, J., Kerr, W. G., Jove, R., Pardoll, D., and Yu, H. Inhibiting Stat3 signaling in the hematopoietic system elicits multicomponent antitumor immunity. Nat Med, 11: 1314-1321, 2005.

Kortylewski, M., Swiderski, P., Herrmann, A., Wang, L., Kowolik, C., Kujawski, M., Lee, H., Scuto, A., Liu, Y., Yang, C., Deng, J., Soifer, H. S., Raubitschek, A., Forman, S., Rossi, J. J., Pardoll, D. M., Jove, R., and Yu, H. In vivo delivery of siRNA to immune cells by conjugation to a TLR9 agonist enhances antitumor immune responses. Nat Biotechnol, 27:925-932, 2009a.

Kortylewski, M., Xin, H., Kujawski, M., Lee, H., Liu, Y., Harris, T., Drake, C., Pardoll, D., and Yu, H. Regulation of the IL-23 and IL-12 balance by Stat3 signaling in the tumor microenvironment. Cancer Cell, 15: 114-123, 2009b.

Kousis P C, Henderson B W, Maier P G, Gollnick S O. Photodynamic therapy enhancement of antitumor immunity is regulated by neutrophils. Cancer Res. 2007; 67:10501-10510.

Kraman, M., Bambrough, P. J., Arnold, J. N., Roberts, E. W., Magiera, L., Jones, J. O., Gopinathan, A., Tuveson, D. A., and Fearon, D. T. Suppression of antitumor immunity by stromal cells expressing fibroblast activation protein-alpha. Science, 330: 827-830, 2010.

Kumar, S. et al. Indoleamine 2,3-dioxygenase is the anti-cancer target for a novel series of potent naphthoquinone-based inhibitors. J Med Chem 51, 1706-1718 (2008).

Lazennec G, Richmond A. Chemokines and chemokine receptors: new insights into cancer related inflammation. Trends Mol Med. 2010; 16:133-144.

Lechner et al. Inducible nitric oxide synthase (iNOS) in tumor biology: The two sides of the same coin. Semin Cancer Biol. 15(4):277-89 (2005)

Lee C H, Hsieh J L, Wu C L, Hsu P Y, Shiau A L. T cell augments the antitumor activity of tumortargeting *Salmonella*. Appl Microbiol Biotechnol. 2011; 90:1381-1388.

Lee, H., Pal, S. K., Reckamp, K., Figlin, R. A., and Yu, H. STAT3: A Target to Enhance Antitumor Immune Response. Curr Top Microbiol Immunol., 2010

Liu X, Shin N, Koblish H K et al. Selective inhibition of IDO1 effectively regulates mediators of antitumor immunity. Blood. 2010; 115:3520-3530.

Lob, S., Konigsrainer, A., Rammensee, H. G., Opelz, G. & Terness, P. Inhibitors of indoleamine-2,3-dioxygenase for cancer therapy: can we see the wood for the trees? *Nat Rev Cancer* 9, 445-452 (2009).

Low K B, Ittensohn M, Le T et al. Lipid A mutant *Salmonella* with suppressed virulence and TNFalpha induction retain tumor-targeting in vivo. Nat Biotechnol. 1999; 17:37-41.

Low, K. B. et al. Construction of VNP20009: a novel, genetically stable antibioticsensitive strain of tumor-targeting *Salmonella* for parenteral administration in humans. *Methods Mol Med* 90, 47-60 (2004).

Lu, T., et al. Tumor-infiltrating myeloid cells induce tumor cell resistance to cytotoxic T cells in mice. *J Clin Invest* 121, 4015-4029 (2011).

Luo Y, Markowitz D, Xiang R, Zhou H, Reisfeld R A. FLK-1-based minigene vaccines induce T cell-mediated suppression of angiogenesis and tumor protective immunity in syngeneic BALB/c mice. Vaccine. 2007; 25:1409-1415.

Luo Y, Zhou H, Mizutani M et al. A DNA vaccine targeting Fos-related antigen 1 enhanced by IL-18 induces long-lived T-cell memory against tumor recurrence. Cancer Res. 2005; 65:3419-3427.

Luo, X., Li, Z., Lin, S., Le, T., Ittensohn, M., Bermudes, D., Runyab, J. D., Shen, S. Y., Chen, J., King, I. C., and Zheng, L. M. Antitumor effect of VNP20009, an attenuated *Salmonella*, in murine tumor models. Oncol Res, 12: 501-508, 2001.

Macchiarulo A, Camaioni E, Nuti R, Pellicciari R. Highlights at the gate of tryptophan catabolism: a review on the mechanisms of activation and regulation of indoleamine 2,3-dioxygenase (IDO), a novel target in cancer disease. Amino Acids. 2009; 37:219-229.

Maeurer, M. J. et al. Tumor escape from immune recognition: lethal recurrent melanoma in a patient associated with downregulation of the peptide transporter protein TAP-1 and loss of expression of the immunodominant MART-1/Melan-A antigen. *J Clin Invest* 98, 1633-1641 (1996).

Mandruzzato, S., et al. IL4Ralpha+ myeloid-derived suppressor cell expansion in cancer patients. *J Immunol* 182, 6562-6568 (2009).

Mantovani A, Savino B, Locati M et al. The chemokine system in cancer biology and therapy. Cytokine Growth Factor Rev. 2010; 21:27-39.

Manuel E R, Blache C A, Paquette R et al. Enhancement of Cancer Vaccine Therapy by Systemic Delivery of a Tumor Targeting *Salmonella*-based STAT3 shRNA Suppresses the Growth of Established Melanoma Tumors. Cancer Res. 2011; 71:4183-4191.

Marigo I, Dolcetti L, Serafini P, Zanovello P, Bronte V. Tumor-induced tolerance and immune suppression by myeloid derived suppressor cells. Immunol Rev. 2008; 222:162-179.

Mazzoni, A., et al. Myeloid suppressor lines inhibit T cell responses by an NO-dependent mechanism. *J Immunol* 168, 689-695 (2002).

Medina-Echeverz J, Fioravanti J, Zabala M et al. Successful colon cancer eradication after chemoimmunotherapy is associated with profound phenotypic change of intratumoral myeloid cells. J Immunol. 2011; 186:807-815.

Mellor A. L.& Munn D. H. Creating immune privilege: active local suppression that benefits friends, but protects foes. Nature Reviews Immunology 8, 74-80 (2008).

Mellor A L, Baban B, Chandler P R et al. Cutting edge: CpG oligonucleotides induce splenic CD19+ dendritic cells to acquire potent indoleamine 2,3-dioxygenase-dependent T cell regulatory functions via IFN Type 1 signaling. J Immunol. 2005; 175:5601-5605.

Mellor A L, Munn D H. IDO expression by dendritic cells: tolerance and tryptophan catabolism. Nat Rev Immunol. 2004; 4:762-774.

Mellor A L, Sivakumar J, Chandler P et al. Prevention of T cell-driven complement activation and inflammation by tryptophan catabolism during pregnancy. Nat Immunol. 2001; 2:64-68.

Metz R, DuHadaway J B, Kamasani U et al. Novel tryptophan catabolic enzyme IDO2 is the preferred biochemical target of the antitumor indoleamine 2,3-dioxygenase inhibitory compound D-1-methyl-tryptophan. Cancer Res. 2007; 67:7082-7087.

Molon, B., et al. Chemokine nitration prevents intratumoral infiltration of antigen-specific T cells. *J Exp Med* 208, 1949-1962 (2011).

Movahedi, K., et al. Identification of discrete tumor-induced myeloid-derived suppressor cell subpopulations with distinct T cell-suppressive activity. *Blood* 111, 4233-4244 (2008).

Muller A J, DuHadaway J B, Donover P S, Sutanto-Ward E, Prendergast G C. Inhibition of indoleamine 2,3-dioxygenase, an immunoregulatory target of the cancer suppression gene Bin1, potentiates cancer chemotherapy. Nat Med. 2005; 11:312-319.

Muller A J, DuHadaway J B, Jailer D et al. Immunotherapeutic suppression of indoleamine 2,3-dioxygenase and tumor growth with ethyl pyruvate. Cancer Res. 2010; 70:1845-1853.

Muller A J, Sharma M D, Chandler P R et al. Chronic inflammation that facilitates tumor progression creates local immune suppression by inducing indoleamine 2,3 dioxygenase. Proc Natl Acad Sci USA. 2008; 105:17073-17078.

Munder, M., et al. Th1/Th2-regulated expression of arginase isoforms in murine macrophages and dendritic cells. *J Immunol* 163, 3771-3777 (1999).

Munn D. H. & Mellor A. L. Idoleamine 2,3-dioxygenase and tumor-induced tolerance. J Clin Invest 117:1147-1154 (2007).

Munn D H, Sharma M D, Baban B et al. GCN2 kinase in T cells mediates proliferative arrest and anergy induction in response to indoleamine 2,3-dioxygenase. Immunity. 2005; 22:633-642.

Munn D H, Sharma M D, Hou D et al. Expression of indoleamine 2,3-dioxygenase by plasmacytoid dendritic cells in tumor-draining lymph nodes. J Clin Invest. 2004; 114:280-290.

Munn D H, Zhou M, Attwood J T et al. Prevention of allogeneic fetal rejection by tryptophan catabolism. Science. 1998; 281:1191-1193.

Nagaraj, S., et al. Altered recognition of antigen is a mechanism of CD8+ T cell tolerance in cancer. *Nat Med* 13, 828-835 (2007).

Nemunaitis J, Cunningham C, Senzer N et al. Pilot trial of genetically modified, attenuated *Salmonella* expressing the *E. coli* cytosine deaminase gene in refractory cancer patients. Cancer Gene Ther. 2003; 10:737-744.

Nishikawa H, Sato E, Briones G et al. In vivo antigen delivery by a *Salmonella typhimurium* type III secretion system for therapeutic cancer vaccines. J Clin Invest. 2006; 116:1946-1954.

Norian, L. A., Rodriguez, P. C., O'Mara, L. A., Zabaleta, J., Ochoa, A. C., Cella, M., and Allen, P. M. Tumor-infiltrating regulatory dendritic cells inhibit CD8+ T cell function via Larginine metabolism. Cancer Res, 69: 3086-3094, 2009.

Ostrand-Rosenberg, S. & Sinha, P. Myeloid-derived suppressor cells: linking inflammation and cancer. *J Immunol* 182, 4499-4506 (2009).

Pan, P. Y., et al. Immune stimulatory receptor CD40 is required for T-cell suppression and T regulatory cell activation mediated by myeloid-derived suppressor cells in cancer. *Cancer Res* 70, 99-108 (2010).

Paschen, A. et al. Complete loss of HLA class I antigen expression on melanoma cells: a result of successive mutational events. *Int J Cancer* 103, 759-767 (2003).

Pascolo, S., Bervas, N., Ure, J. M., Smith, A. G., Lemonnier, F. A., and Perarnau, B. HLAA2.1-restricted education and cytolytic activity of CD8(+) T lymphocytes from beta2 microglobulin (beta2m) HLA-A2.1 monochain transgenic H-2 Db beta2m double knockout mice. J Exp Med, 185: 2043-2051, 1997.

Pawelek, J. M., Low, K. B. & Bermudes, D. Bacteria as tumour-targeting vectors. *Lancet Oncol* 4, 548-556 (2003).

Pawelek, J. M., Low, K. B. & Bermudes, D. Tumor-targeted *Salmonella* as a novel anticancer vector. *Cancer Res* 57, 4537-4544 (1997).

Pensa, S. et al., STAT1 and STAT3 in Tumorigenesis: Two Sides of the Same Coin? in JAK-STAT Pathway in Disease 100, 106 (Anastasis Stephanou, ed., Landes Bioscience 2009).

Polak, M. E., Borthwick, N. J., Jager, M. J., and Cree, I. A. Melanoma vaccines: The problems of local immunosuppression. Hum Immunol, 70: 331-339, 2009.

Prendergast G C. Immune escape as a fundamental trait of cancer: focus on IDO. Oncogene. 2008; 27:3889-3900.

Rodriguez P C, Ernstoff M S, Hernandez C et al. Arginase I-producing myeloid-derived suppressor cells in renal cell carcinoma are a subpopulation of activated granulocytes. Cancer Res. 2009; 69:1553-1560.

Rodriguez, P. C., Quiceno, D. G., Zabaleta, J., Arginase I production in the tumor microenvironment by mature myeloid cells inhibits T-cell receptor expression and antigen-specific T-cell responses. Cancer Res 64, 5839-5849 (2004).

Rodriguez, P. C., Zea, A. H., and Ochoa, A. C. Mechanisms of tumor evasion from the immune response. Cancer Chemother Biol Response Modif, 21: 351-364, 2003.

Rosenberg S A, Restifo N P, Yang J C, Morgan R A, Dudley M E. Adoptive cell transfer: a clinical path to effective cancer immunotherapy. Nat Rev Cancer. 2008; 8:299-308.

Rosenberg, S. A., Spiess, P. J., and Kleiner, D. E. Antitumor effects in mice of the intravenous injection of attenuated *Salmonella typhimurium*. J Immunother, 25: 218-225, 2002.

Rothe, G. & Valet, G. Flow cytometric analysis of respiratory burst activity in phagocytes with hydroethidine and 2',7'-dichlorofluorescin. *J Leukoc Biol* 47, 440-448 (1990).

Russmann H, Shams H, Poblete F et al. Delivery of epitopes by the *Salmonella* type III secretion system for vaccine development. Science. 1998; 281:565-568.

Ryan, B. M., O'Donovan, N., and Duffy, M. J. Survivin: a new target for anti-cancer therapy. Cancer Treat Rev, 35: 553-562, 2009.

Sakaguchi S, Wing K, Onishi Y, Prieto-Martin P, Yamaguchi T. Regulatory T cells: how do they suppress immune responses? International Immunology, 21(10):1105-1111, 2009.

Scheel-Toellner D, Wang K, Assi L K et al. Clustering of death receptors in lipid rafts initiates neutrophil spontaneous apoptosis. Biochem Soc Trans. 2004; 32:679-681.

Schmielau, J. & Finn, O. J. Activated granulocytes and granulocyte-derived hydrogen peroxide are the underlying mechanism of suppression of t-cell function in advanced cancer patients. *Cancer Res* 61, 4756-4760 (2001).

Serafini, P., Mgebroff, S., Noonan, K. & Borrello, I. Myeloid-derived suppressor cells promote cross-tolerance in B-cell lymphoma by expanding regulatory T cells. *Cancer Res* 68, 5439-5449 (2008).

Sharma M D, Baban B, Chandler P et al. Plasmacytoid dendritic cells from mouse tumor-draining lymph nodes directly activate mature Tregs via indoleamine 2,3-dioxygenase. J Clin Invest. 2007; 117:2570-2582.

Sharma M D, Hou D Y, Liu Y et al. Indoleamine 2,3-dioxygenase controls conversion of Foxp3+ Tregs to TH17-like cells in tumor-draining lymph nodes. Blood. 2009; 113:6102-6111.

Simons M P, Nauseef W M, Griffith T S. Neutrophils and TRAIL: insights into BCG immunotherapy for bladder cancer. Immunol Res. 2007; 39:79-93.

Simons M P, O'Donnell M A, Griffith T S. Role of neutrophils in BCG immunotherapy for bladder cancer. Urol Oncol. 2008; 26:341-345.

Sinha, P., Clements, V. K., Bunt, S. K., Albelda, S. M. & Ostrand-Rosenberg, S. Cross-talk between myeloid-derived suppressor cells and macrophages subverts tumor immunity toward a type 2 response. *J Immunol* 179, 977-983 (2007).

Soliman H, Mediavilla-Varela M, Antonia S. Indoleamine 2,3-dioxygenase: is it an immune suppressor? Cancer J. 2010; 16:354-359.

Sorensen R B, Berge-Hansen L, Junker N et al. The immune system strikes back: cellular immune responses against indoleamine 2,3-dioxygenase. PLoS ONE. 2009; 4:e6910.

Sorensen R B, Hadrup S R, Svane I M et al. Indoleamine 2,3-dioxygenase specific, cytotoxic T cells as immune regulators. Blood. 2011; 117:2200-2210.

Sorensen R B, Kollgaard T, Andersen R S et al. Spontaneous Cytotoxic T-Cell Reactivity against Indoleamine 2,3-Dioxygenase-2. Cancer Res. 2011; 71:2038-2044.

Srikanth C V, Wall D M, Maldonado-Contreras A et al. *Salmonella* pathogenesis and processing of secreted effectors by caspase-3. Science. 2010; 330:390-393.

Stockmeyer, B. et al. Polymorphonuclear granulocytes induce antibodydependent apoptosis in human breast cancer cells. *J Immunol* 171, 5124-5129 (2003).

Suttmann H, Riemensberger J, Bentien G et al. Neutrophil granulocytes are required for effective *Bacillus* Calmette-Guerin immunotherapy of bladder cancer and orchestrate local immune responses. Cancer Res. 2006; 66:8250-8257.

Tepper R I, Coffman R L, Leder P. An eosinophil-dependent mechanism for the antitumor effect of interleukin-4. Science. 1992; 257:548-551.

Terabe, M. & Berzofsky, J. A. NKT cells in immunoregulation of tumor immunity: a new immunoregulatory axis. Trends Immunol 28, 491-496 (2007).

Theys, J., Barbe, S., Landuyt, W., Nuyts, S., Van Mellaert, L., Wouters, B., Anne, J., and Lambin, P. Tumor-specific gene delivery using genetically engineered bacteria. Curr Gene Ther, 3: 207-221, 2003.

Tomihara K, Guo M, Shin T et al. Antigen-specific immunity and cross-priming by epithelial ovarian carcinoma-induced CD11b(+)Gr-1(+) cells. J Immunol. 2010; 184: 6151-6160.

Toso, J. F. et al. Phase I study of the intravenous administration of attenuated Salmonella typhimurium to patients with metastatic melanoma. J Clin Oncol 20, 142-152 (2002).

Tran, J., Rak, J., Sheehan, C., Saibil, S. D., LaCasse, E., Korneluk, R. G., and Kerbel, R. S. Marked induction of the IAP family antiapoptotic proteins survivin and XIAP by VEGF in vascular endothelial cells. Biochem Biophys Res Commun, 264: 781-788, 1999.

Tsunetsugu-Yokota, Y., Ishige, M., and Murakami, M. Oral attenuated Salmonella enterica serovar Typhimurium vaccine expressing codon-optimized HIV type 1 Gag enhanced intestinal immunity in mice. AIDS Res Hum Retroviruses, 23: 278-286, 2007.

Uyttenhove, C., Pilotte, L., Theate, I., Stroobant, V., Colau, D., Parmentier, N., Boon, T., and Van den Eynde, B. J. Evidence for a tumoral immune resistance mechanism based on tryptophan degradation by indoleamine 2,3-dioxygenase. Nat Med, 9: 1269-1274, 2003.

Van der Sluijs, K., Singh, R., Dijkhuis, A., Snoek, M., and Lutter, R. Indoleamine 2,3-dioxygenase activity induces neutrophil apoptosis. Critical Care 15, 208 (2011).

Vitiello A, Marchesini D, Furze J, Sherman L A, Chesnut R W. Analysis of the HLA-restricted influenza-specific cytotoxic T lymphocyte response in transgenic mice carrying a chimeric human-mouse class I major histocompatibility complex. J Exp Med. 1991; 173:1007-1015.

Wang L C, Thomsen L, Sutherland R et al. Neutrophil influx and chemokine production during the early phases of the antitumor response to the vascular disrupting agent DMXAA (ASA404). Neoplasia. 2009; 11:793-803.

Wang, J. & Yi, J. Cancer cell killing via ROS: to increase or decrease, that is the question. Cancer Biol Ther 7, 1875-1884 (2008).

Wang, T., Niu, G., Kortylewski, M., Burdelya, L., Shain, K., Zhang, S., Bhattacharya, R., Gabrilovich, D., Heller, R., Coppola, D., Dalton, W., Jove, R., Pardoll, D., and Yu, H. Regulation of the innate and adaptive immune responses by Stat-3 signaling in tumor cells. Nat Med, 10: 48-54, 2004.

Westphal K, Leschner S, Jablonska J, Loessner H, Weiss S. Containment of tumor-colonizing bacteria by host neutrophils. Cancer Res. 2008; 68:2952-2960.

Whiteside, T. L. The tumor microenvironment and its role in promoting tumor growth.
Oncogene, 27: 5904-5912, 2008.

Wick M J. Living in the danger zone: innate immunity to Salmonella. Curr Opin Microbiol. 2004; 7:51-57.

Witkiewicz A K, Costantino C L, Metz R et al. Genotyping and expression analysis of IDO2 in human pancreatic cancer: a novel, active target. J Am Coll Surg. 2009; 208:781-787.

Wright H L, Moots R J, Bucknall R C, Edwards S W. Neutrophil function in inflammation and inflammatory diseases. Rheumatology (Oxford). 2010; 49:1618-1631.

Xia, Y., Roman, L. J., Masters, B. S. & Zweier, J. L. Inducible nitric-oxide synthase generates superoxide from the reductase domain. J Biol Chem 273, 22635-22639 (1998).

Xia, Y. & Zweier, J. L. Superoxide and peroxynitrite generation from inducible nitric oxide synthase in macrophages. Proc Natl Acad Sci USA 94, 6954-6958 (1997).

Xiang R, Luo Y, Niethammer A G, Reisfeld R A. Oral DNA vaccines target the tumor vasculature and microenvironment and suppress tumor growth and metastasis. Immunol Rev. 2008; 222:117-128.

Xiang, R., Mizutani, N., Luo, Y., Chiodoni, C., Zhou, H., Mizutani, M., Ba, Y., Becker, J. C., and Reisfeld, R. A. A DNA vaccine targeting survivin combines apoptosis with suppression of angiogenesis in lung tumor eradication. Cancer Res, 65: 553-561, 2005.

Xiang R, Primus F J, Ruehlmann J M et al. A dual-function DNA vaccine encoding carcinoembryonic antigen and CD40 ligand trimer induces T cell-mediated protective immunity against colon cancer in carcinoembryonic antigen-transgenic mice. J Immunol. 2001; 167:4560-4565.

Xiong, G., Husseiny, M. I., Song, L., Erdreich-Epstein, A., Shackleford, G. M., Seeger, R. C., Jackel, D., Hensel, M., and Metelitsa, L. S. Novel cancer vaccine based on genes of Salmonella pathogenicity island 2. Int J Cancer, 126: 2622-2634, 2009.

Xu, D. Q., Zhang, L., Kopecko, D. J., Gao, L., Shao, Y., Guo, B., and Zhao, L. Bacterial delivery of siRNAs: a new approach to solid tumor therapy. Methods Mol Biol, 487: 161-187, 2009.

Yamashiro S, Kamohara H, Wang J M et al. Phenotypic and functional change of cytokineactivated neutrophils: inflammatory neutrophils are heterogeneous and enhance adaptive immune responses. J Leukoc Biol. 2001; 69:698-704.

Yang L, Pang Y, Moses H L. TGF-beta and immune cells: an important regulatory axis in the tumor microenvironment and progression. Trends Immunol. 2010; 31:220-227.

Yen M C, Lin C C, Chen Y L et al. A novel cancer therapy by skin delivery of indoleamine 2,3-dioxygenase siRNA. Clin Cancer Res. 2009; 15:641-649.

Yin, K., Liu, Q., Zhu, S., and Yan, G. Adenovirus-mediated siRNA inhibited survivin gene expression induces tumor cell apoptosis in nude mice. Biosci Trends, 2: 231-234, 2008.

Youn, J. I., Collazo, M., Shalova, I. N., Biswas, S. K. & Gabrilovich, D. I. Characterization of the nature of granulocytic myeloid-derived suppressor cells in tumor-bearing mice. J Leukoc Biol 91, 167-181 (2012).

Youn, J. I., Nagaraj, S., Collazo, M. & Gabrilovich, D. I. Subsets of myeloid-derived suppressor cells in tumor-bearing mice. J Immunol 181, 5791-5802 (2008).

Yu, H., Kortylewski, M., and Pardoll, D. Crosstalk between cancer and immune cells: role of STAT3 in the tumour microenvironment. Nat Rev Immunol, 7: 41-51, 2007.

Zhang, L., Gao, L., Zhao, L., Guo, B., Ji, K., Tian, Y., Wang, J., Yu, H., Hu, J., Kalvakolanu, D. V., Kopecko, D. J., Zhao, X., and Xu, D. Q. Intratumoral delivery and suppression of prostate tumor growth by attenuated Salmonella enterica serovar typhimurium carrying plasmid-based small interfering RNAs. Cancer Res, 67: 5859-5864, 2007.

Zhang, Y., Chen, Z. D., Du, C. J., Xu, G., and Luo, W. siRNA targeting survivin inhibits growth and induces apoptosis in human renal clear cell carcinoma 786-O cells. Pathol Res Pract, 205: 823-827, 2009.

Zhao M, Yang M, Li X M et al. Tumor-targeting bacterial therapy with amino acid auxotrophs of GFP-expressing *Salmonella typhimurium*. Proc Natl Acad Sci USA. 2005; 102:755-760.

Zhao M, Yang M, Ma H et al. Targeted therapy with a *Salmonella typhimurium* leucine-arginine auxotroph cures orthotopic human breast tumors in nude mice. Cancer Res. 2006; 66:7647-7652.

Zheng, X., Koropatnick, J., Li, M., Zhang, X., Ling, F., Ren, X., Hao, X., Sun, H., Vladau, C., Franek, J. A., Feng, B., Urquhart, B. L., Zhong, R., Freeman, D. J., Garcia, B., and Min, W. P. Reinstalling antitumor immunity by inhibiting tumor-derived immunosuppressive molecule IDO through RNA interference. J Immunol, 177: 5639-5646, 2006.

Zhou, H., Luo, Y., Kaplan, C. D., Kruger, J. A., Lee, S. H., Xiang, R., and Reisfeld, R. A. A DNA-based cancer vaccine enhances lymphocyte cross talk by engaging the NKG2D receptor. Blood, 107: 3251-3257, 2006.

Zhu G, Augustine M M, Azuma T et al. B7-H4-deficient mice display augmented neutrophilmediated innate immunity. Blood. 2009; 113:1759-1767.

Zivkovic, M. et al. Oxidative burst and anticancer activities of rat neutrophils. *Biofactors* 24, 305-312 (2005).

What is claimed is:

1. A single modality cancer immunotherapy regimen comprising a therapeutic composition, the composition comprising a *Salmonella* strain selected from the group consisting of YS1646 (ATCC #202165), RE88, SL7207, x8429, x8431 and x8468 comprising a plasmid that expresses an shRNA molecule that suppresses the expression of an immunosuppressive target IDO1 and suppresses tumor growth.

2. The composition of claim 1, wherein the *Salmonella* strain is an attenuated *Salmonella typhimurium* strain.

3. The composition of claim 1 wherein the cancer treatment of claim 1, wherein the shRNA is selected from any one of SEQ ID NO:5-9.

4. A method of treating cancer comprising administering a therapeutically effective amount of a therapeutic composition, the composition comprising an anti-immunosuppressant vector that disrupts tumor-derived immune suppression and suppresses tumor growth, wherein the anti-immunosuppressant vactor comprises an attenuated Salmonella typhimurium strain selected from the group consisting of YS1646 (ATCC #202165), RE88, SL7207, x8429, x8431, and x8468 comprising a plasmid that expresses an shRNA molecule that suppresses the expression of an immunosuppressive target IDO1 and suppresses tumor growth.

5. The method of claim 4, wherein the *Salmonella* strain is administered intravenously.

6. The method of claim 4, wherein the shRNA molecule is any one of SEQ ID NOs:5-9.

7. A method of suppressing tumor growth comprising intravenously administering to a subject a *Salmonella* strain selected from the group consisting of YS1646 (ATCC #202165), RE88, SL7207, x8429, x8431, and x8468 comprising a plasmid that expresses an shRNA molecule that suppresses the expression of an immunosuppressive target IDO1 and suppresses tumor growth.

8. The method of claim 7, wherein the *Salmonella* strain is an attenuated *Salmonella typhimurium* strain.

9. The method of claim 7, wherein the shRNA molecule is any one of SEQ ID NOs:5-9.

* * * * *

UNITED STATES PATENT AND TRADEMARK OFFICE
CERTIFICATE OF CORRECTION

PATENT NO. : 9,453,227 B2  
APPLICATION NO. : 14/065284  
DATED : September 27, 2016  
INVENTOR(S) : Don J. Diamond et al.

Page 1 of 1

It is certified that error appears in the above-identified patent and that said Letters Patent is hereby corrected as shown below:

On the Title Page

In item (72) for Inventors, delete "Fernanda V. V. Castro, Monrovia, CA (US)."

Signed and Sealed this
Eighteenth Day of September, 2018

Andrei Iancu
*Director of the United States Patent and Trademark Office*

SEQUENCE LISTING

```
<160> NUMBER OF SEQ ID NOS: 40

<210> SEQ ID NO 1
<211> LENGTH: 29
<212> TYPE: DNA
<213> ORGANISM: Artificial Sequence
<220> FEATURE:
<223> OTHER INFORMATION: Synthetic: shSTAT3#58

<400> SEQUENCE: 1
agttcctggc accttggatt gagagtcaa                                          29

<210> SEQ ID NO 2
<211> LENGTH: 29
<212> TYPE: DNA
<213> ORGANISM: Artificial Sequence
<220> FEATURE:
<223> OTHER INFORMATION: Synthetic: shSTAT3#59

<400> SEQUENCE: 2
actggataac ttcattagca gaatctcaa                                          29

<210> SEQ ID NO 3
<211> LENGTH: 29
<212> TYPE: DNA
<213> ORGANISM: Artificial Sequence
<220> FEATURE:
<223> OTHER INFORMATION: Synthetic: shSTAT3#60

<400> SEQUENCE: 3
catcaatcct gtggtataac atgctgacc                                          29

<210> SEQ ID NO 4
<211> LENGTH: 29
<212> TYPE: DNA
<213> ORGANISM: Artificial Sequence
<220> FEATURE:
<223> OTHER INFORMATION: Synthetic: shSTAT3#61

<400> SEQUENCE: 4
acctgaagac caagttcatc tgtgtgaca                                          29

<210> SEQ ID NO 5
<211> LENGTH: 19
<212> TYPE: DNA
<213> ORGANISM: Artificial Sequence
<220> FEATURE:
<223> OTHER INFORMATION: Synthetic: shIDO1-8

<400> SEQUENCE: 5
cctcgcaata gtagatact                                                     19
```

```
<210> SEQ ID NO 6
<211> LENGTH: 19
<212> TYPE: DNA
<213> ORGANISM: Artificial Sequence
<220> FEATURE:
<223> OTHER INFORMATION: Synthetic: shIDO1-9

<400> SEQUENCE: 6
cgtctctcta ttggtggaa                                                19

<210> SEQ ID NO 7
<211> LENGTH: 19
<212> TYPE: DNA
<213> ORGANISM: Artificial Sequence
<220> FEATURE:
<223> OTHER INFORMATION: Synthetic: shIDO1-10

<400> SEQUENCE: 7
gcaaagaatc tcctgcaga                                                19

<210> SEQ ID NO 8
<211> LENGTH: 19
<212> TYPE: DNA
<213> ORGANISM: Artificial Sequence
<220> FEATURE:
<223> OTHER INFORMATION: Synthetic: shIDO1-11

<400> SEQUENCE: 8
gcccatgaca tacgagaac                                                19

<210> SEQ ID NO 9
<211> LENGTH: 19
<212> TYPE: DNA
<213> ORGANISM: Artificial Sequence
<220> FEATURE:
<223> OTHER INFORMATION: Synthetic: shIDO1-12

<400> SEQUENCE: 9
ccagtccgtg agtttgtca                                                19

<210> SEQ ID NO 10
<211> LENGTH: 19
<212> TYPE: DNA
<213> ORGANISM: Artificial Sequence
<220> FEATURE:
<223> OTHER INFORMATION: Synthetic: shArg1-5

<400> SEQUENCE: 10
gcagttcctt tctggtatg                                                19

<210> SEQ ID NO 11
<211> LENGTH: 18
<212> TYPE: DNA
<213> ORGANISM: Artificial Sequence
<220> FEATURE:
<223> OTHER INFORMATION: Synthetic: shArg1-6

<400> SEQUENCE: 11
gcctttgttg atgtccct                                                 18

<210> SEQ ID NO 12
<211> LENGTH: 19
<212> TYPE: DNA
<213> ORGANISM: Artificial Sequence
<220> FEATURE:
<223> OTHER INFORMATION: Synthetic: shArg1-7
```

```
<400> SEQUENCE: 12
ccagggactg actaccttta                                                    19

<210> SEQ ID NO 13
<211> LENGTH: 19
<212> TYPE: DNA
<213> ORGANISM: Artificial Sequence
<220> FEATURE:
<223> OTHER INFORMATION: Synthetic: shArg1-8

<400> SEQUENCE: 13
gccaaagaca tcgtgtaca                                                     19

<210> SEQ ID NO 14
<211> LENGTH: 18
<212> TYPE: DNA
<213> ORGANISM: Artificial Sequence
<220> FEATURE:
<223> OTHER INFORMATION: Synthetic: shArg1-9

<400> SEQUENCE: 14
tctctacatc acagaaga                                                      18

<210> SEQ ID NO 15
<211> LENGTH: 21
<212> TYPE: DNA
<213> ORGANISM: Artificial Sequence
<220> FEATURE:
<223> OTHER INFORMATION: Synthetic: shiNOS-43

<400> SEQUENCE: 15
gtattgtact attgtggact a                                                  21

<210> SEQ ID NO 16
<211> LENGTH: 21
<212> TYPE: DNA
<213> ORGANISM: Artificial Sequence
<220> FEATURE:
<223> OTHER INFORMATION: Synthetic: shiNOS-44

<400> SEQUENCE: 16
ccagtattat ggctccttta a                                                  21

<210> SEQ ID NO 17
<211> LENGTH: 21
<212> TYPE: DNA
<213> ORGANISM: Artificial Sequence
<220> FEATURE:
<223> OTHER INFORMATION: Synthetic: shiNOS-45

<400> SEQUENCE: 17
gccacagcaa tataggctca t                                                  21

<210> SEQ ID NO 18
<211> LENGTH: 21
<212> TYPE: DNA
<213> ORGANISM: Artificial Sequence
<220> FEATURE:
<223> OTHER INFORMATION: Synthetic: shiNOS-46

<400> SEQUENCE: 18
cctatctcca ttctactact a                                                  21

<210> SEQ ID NO 19
```

```
<211> LENGTH: 21
<212> TYPE: DNA
<213> ORGANISM: Artificial Sequence
<220> FEATURE:
<223> OTHER INFORMATION: Synthetic: shiNOS-47

<400> SEQUENCE: 19
gctgtaacaa aggaaataga a                                              21

<210> SEQ ID NO 20
<211> LENGTH: 27
<212> TYPE: DNA
<213> ORGANISM: Artificial Sequence
<220> FEATURE:
<223> OTHER INFORMATION: Synthetic: STAT3 Forward

<400> SEQUENCE: 20
catgggctat aagatcatgg atgcgac                                        27

<210> SEQ ID NO 21
<211> LENGTH: 27
<212> TYPE: DNA
<213> ORGANISM: Artificial Sequence
<220> FEATURE:
<223> OTHER INFORMATION: Synthetic: STAT3 Reverse

<400> SEQUENCE: 21
agggctcagc accttcaccg ttatttc                                        27

<210> SEQ ID NO 22
<211> LENGTH: 23
<212> TYPE: DNA
<213> ORGANISM: Artificial Sequence
<220> FEATURE:
<223> OTHER INFORMATION: Synthetic: GAPDH Forward

<400> SEQUENCE: 22
caaggtcatc catgacaact ttg                                            23

<210> SEQ ID NO 23
<211> LENGTH: 22
<212> TYPE: DNA
<213> ORGANISM: Artificial Sequence
<220> FEATURE:
<223> OTHER INFORMATION: Synthetic: GAPDH Reverse

<400> SEQUENCE: 23
gtccaccacc ctgttgctgt ag                                             22

<210> SEQ ID NO 24
<211> LENGTH: 21
<212> TYPE: DNA
<213> ORGANISM: Artificial Sequence
<220> FEATURE:
<223> OTHER INFORMATION: Synthetic: shRNA sense sequence

<400> SEQUENCE: 24
cgtctctcta ttggtggaaa t                                              21

<210> SEQ ID NO 25
<211> LENGTH: 24
<212> TYPE: DNA
<213> ORGANISM: Artificial Sequence
<220> FEATURE:
<223> OTHER INFORMATION: Synthetic: Forward IDO primer

<400> SEQUENCE: 25
```

```
ggaaccgagg ggatgacgat gttc                                          24
```

<210> SEQ ID NO 26
<211> LENGTH: 26
<212> TYPE: DNA
<213> ORGANISM: Artificial Sequence
<220> FEATURE:
<223> OTHER INFORMATION: Synthetic: Reverse IDO primer

<400> SEQUENCE: 26

```
agactggtag ctatgtcgtg cagtgc                                        26
```

<210> SEQ ID NO 27
<211> LENGTH: 23
<212> TYPE: DNA
<213> ORGANISM: Artificial Sequence
<220> FEATURE:
<223> OTHER INFORMATION: Synthetic: Forward GAPDH primer

<400> SEQUENCE: 27

```
caaggtcatc catgacaact ttg                                           23
```

<210> SEQ ID NO 28
<211> LENGTH: 22
<212> TYPE: DNA
<213> ORGANISM: Artificial Sequence
<220> FEATURE:
<223> OTHER INFORMATION: Synthetic: Reverse GAPDH primer

<400> SEQUENCE: 28

```
gtccaccacc ctgttgctgt ag                                            22
```

<210> SEQ ID NO 29
<211> LENGTH: 465
<212> TYPE: DNA
<213> ORGANISM: Artificial Sequence
<220> FEATURE:
<223> OTHER INFORMATION: Synthetic: Nucleotide sequence for codon-
      optimized SVN (CO-SVN)

<400> SEQUENCE: 29

```
gatatcggcg cgccgaccct gccgccggcg tggcagccgt tcctgaaaga ccaccgtatc    60
tctaccttca aaaactggcc gttcctggaa ggctgcgcgt gcaccccgga acgtatggcg   120
gaagcgggct tcatccactg cccgaccgaa aacgaaccgg acctggcgca gtgcttcttc   180
tgcttcaaag aactggaagg ctgggaaccg acgacgacc cgatcgaaga acacaaaaaa   240
cactcttctg gctgcgcgtt cctgtctgtt aaaaaacagt tcgaagaact gaccctgggc   300
gaattcctga actggaccg tgaacgtgcg aaaaacaaaa tcgcgaaaga accaacaac   360 aaaaaaaag aattcgaaga aaccgcgaaa aaagttcgtc gtgcgatcga acagctggcg   420
gcgatggact acccgtacga cgttccggac tacgcgtaat ctaga                  465
```

<210> SEQ ID NO 30
<211> LENGTH: 150
<212> TYPE: PRT
<213> ORGANISM: Artificial Sequence
<220> FEATURE:
<223> OTHER INFORMATION: Synthetic: Amino acid sequence for codon-
      optimized SVN (CO-SVN)

<400> SEQUENCE: 30

Gly Ala Pro Thr Leu Pro Pro Ala Trp Gln Pro Phe Leu Lys Asp His
1               5                   10                  15

Arg Ile Ser Thr Phe Lys Asn Trp Pro Phe Leu Glu Gly Cys Ala Cys
            20                  25                  30

Thr Pro Glu Arg Met Ala Glu Ala Gly Phe Ile His Cys Pro Thr Glu
        35                  40                  45

Asn Glu Pro Asp Leu Ala Gln Cys Phe Phe Cys Phe Lys Glu Leu Glu
    50                  55                  60

Gly Trp Glu Pro Asp Asp Asp Pro Ile Glu Glu His Lys Lys His Ser
65                  70                  75                  80

Ser Gly Cys Ala Phe Leu Ser Val Lys Lys Gln Phe Glu Glu Leu Thr
                85                  90                  95

Leu Gly Glu Phe Leu Lys Leu Asp Arg Glu Arg Ala Lys Asn Lys Ile
            100                 105                 110

Ala Lys Glu Thr Asn Asn Lys Lys Glu Phe Glu Glu Thr Ala Lys
        115                 120                 125

Lys Val Arg Arg Ala Ile Glu Gln Leu Ala Ala Met Asp Tyr Pro Tyr
130                 135                 140

Asp Val Pro Asp Tyr Ala
145                 150

<210> SEQ ID NO 31
<211> LENGTH: 465
<212> TYPE: DNA
<213> ORGANISM: Artificial Sequence
<220> FEATURE:
<223> OTHER INFORMATION: Synthetic: Nucleotide sequence for minimally
      codon-optimized SVN

<400> SEQUENCE: 31
gatatcggtg ccccgacgtt gccgcctgcc tggcagccgt ttctcaagga ccaccgcatc      60
tctacattca agaactggcc gttcttggag ggctgcgcct gcaccccgga gcggatggcc     120
gaggctggct tcatccactg cccgactgag aacgagccag acttggccca gtgtttcttc     180
tgcttcaagg agctggaagg ctgggagcca gatgacgacc cgatcgagga acataaaaag     240
cattcgtccg gttgcgcttt cctttctgtc aagaagcagt ttgaagaatt aacccttggt     300
gaatttttga actggaccg tgaacgtgcc aagaacaaaa ttgcaaagga accaacaat     360 aagaagaaag aatttgagga aactgcgaag aaagtgcgcc gtgccatcga gcagctggct     420
gctatggatt acccgtacga cgttccggac tacgcgtaat ctaga                    465

<210> SEQ ID NO 32
<211> LENGTH: 150
<212> TYPE: PRT
<213> ORGANISM: Artificial Sequence
<220> FEATURE:
<223> OTHER INFORMATION: Synthetic: Amino acid sequenc for minimally
      codon-optimized SVN

<400> SEQUENCE: 32

Gly Ala Pro Thr Leu Pro Pro Ala Trp Gln Pro Phe Leu Lys Asp His
1               5                   10                  15

Arg Ile Ser Thr Phe Lys Asn Trp Pro Phe

```
                65                  70                  75                  80
Ser Gly Cys Ala Phe Leu Ser Val Lys Lys Gln Phe Glu Glu Leu Thr
                    85                  90                  95

Leu Gly Glu Phe Leu Lys Leu Asp Arg Glu Arg Ala Lys Asn Lys Ile
                100                 105                 110

Ala Lys Glu Thr Asn Asn Lys Lys Lys Glu Phe Glu Thr Ala Lys
            115                 120                 125

Lys Val Arg Arg Ala Ile Glu Gln Leu Ala Ala Met Asp Tyr Pro Tyr
        130                 135                 140

Asp Val Pro Asp Tyr Ala
145                 150

<210> SEQ ID NO 33
<211> LENGTH: 465
<212> TYPE: DNA
<213> ORGANISM: Artificial Sequence
<220> FEATURE:
<223> OTHER INFORMATION: Synthetic: Nucleotide sequence for non-codon
      optimized eukaryotic SVN

<400> SEQUENCE: 33
gatatcggtg ccccgacgtt gcccctgcc tggcagccct ttctcaagga ccaccgcatc        60
tctacattca agaactggcc cttcttggag gctgcgcct gcaccccgga gcggatggcc       120
gaggctggct catccactg ccccactgag aacgagccag acttggccca gtgtttcttc       180
tgcttcaagg agctggaagg ctgggagcca gatgacgacc ccatagagga cataaaaag       240 cattcgtccg gttgcgcttt cctttctgtc aagaagcagt ttgaagaatt aacccttggt       300 gaattttga actggacag agaaagagcc aagaacaaaa ttgcaaagga accaacaat         360 aagaagaaag aatttgagga aactgcgaag aaagtgcgcc gtgccatcga gcagctggct      420
gctatggatt acccatacga cgtcccagac tacgcttaat ctaga                      465

<210> SEQ ID NO 34
<211> LENGTH: 150
<212> TYPE: PRT
<213> ORGANISM: Artificial Sequence
<220> FEATURE:
<223> OTHER INFORMATION: Synthetic: Amino acid sequence for non-codon
      optimized eukaryotic SVN

<400> SEQUENCE: 34

Gly Ala Pro Thr Leu Pro Pro Ala Trp Gln Pro Phe Leu Lys Asp His
1               5                   10                  15

Arg Ile Ser Thr Phe Lys Asn Trp Pro Phe Leu Glu Gly Cys Ala Cys
            20                  25                  30

Thr Pro Glu Arg Met Ala Glu Ala Gly Phe Ile His Cys Pro Thr Glu
        35                  40                  45

Asn Glu Pro Asp Leu Ala Gln Cys Phe Phe Cys Phe Lys Glu Leu Glu
    50                  55                  60

Gly Trp Glu Pro Asp Asp Asp Pro Ile Glu Glu His Lys Lys His Ser
65                  70                  75                  80

Ser Gly Cys Ala Phe Leu Ser Val Lys Lys Gln Phe Glu Glu Leu Thr
                    85                  90                  95

Leu Gly Glu Phe Leu Lys Leu Asp Arg Glu Arg Ala Lys Asn Lys Ile
                100                 105                 110

Ala Lys Glu Thr Asn Asn Lys Lys Lys Glu Phe Glu Glu Thr Ala Lys
            115                 120                 125
```

Lys Val Arg Arg Ala Ile Glu Gln Leu Ala Ala Met Asp Tyr Pro Tyr
    130                 135                 140

Asp Val Pro Asp Tyr Ala
145                 150

<210> SEQ ID NO 35
<211> LENGTH: 48
<212> TYPE: DNA
<213> ORGANISM: Artificial Sequence
<220> FEATURE:
<223> OTHER INFORMATION: Synthetic: shIDO#8

<400> SEQUENCE: 35
cctcgcaata gtagatactt actcgagtaa gtatctacta ttgcgagg        48

<210> SEQ ID NO 36
<211> LENGTH: 48
<212> TYPE: DNA
<213> ORGANISM: Artificial Sequence
<220> FEATURE:
<223> OTHER INFORMATION: Synthetic: shIDO#9

<400> SEQUENCE: 36
cgtctctcta ttggtggaaa tctcgagatt tccaccaata gagagacg        48

<210> SEQ ID NO 37
<211> LENGTH: 48
<212> TYPE: DNA
<213> ORGANISM: Artificial Sequence
<220> FEATURE:
<223> OTHER INFORMATION: Synthetic: shIDO#10

<400> SEQUENCE: 37
gcaaagaatc tcctgcagaa tctcgagatt ctgcaggaga ttctttgc        48

<210> SEQ ID NO 38
<211> LENGTH: 48
<212> TYPE: DNA
<213> ORGANISM: Artificial Sequence
<220> FEATURE:
<223> OTHER INFORMATION: Synthetic: shIDO#11

<400> SEQUENCE: 38
gcccatgaca tacgagaaca tctcgagatg ttctcgtatg tcatgggc        48

<210> SEQ ID NO 39
<211> LENGTH: 48
<212> TYPE: DNA
<213> ORGANISM: Artificial Sequence
<220> FEATURE:
<223> OTHER INFORMATION: Synthetic: shIDO#12

<400> SEQUENCE: 39
ccagtccgtg agtttgtcat tctcgagaat gacaaactca cggactgg        48

<210> SEQ ID NO 40
<211> LENGTH: 48
<212> TYPE: DNA
<213> ORGANISM: Artificial Sequence
<220> FEATURE:
<223> OTHER INFORMATION: Synthetic: scrambled shRNA

<400> SEQUENCE: 40
cgtgatcttc accgacaaga tctcgagatc ttgtcggtga agatcacg        48